(12) United States Patent
Park et al.

(10) Patent No.: US 9,193,989 B2
(45) Date of Patent: Nov. 24, 2015

(54) PRPK-TPRKB MODULATORS AND USES THEREOF

(75) Inventors: Eun Sun Park, Arlington, MA (US); Henry E. Pelish, Newton, MA (US); Astrid S. Clarke, Andover, MA (US); Grace L. Williams, Waltham, MA (US); Maria Paola Castaldi, Brookline, MA (US); Alexander Arefolov, Newton, MA (US); Jennifer E. Ring, Lowell, MA (US); Matthew D. Shair, Lexington, MA (US); Randall W. King, Newton, MA (US)

(73) Assignee: TAIHO PHARMACEUTICAL CO., LTD., Tokyo (JP)

(*) Notice: Subject to any disclaimer, the term of this patent is extended or adjusted under 35 U.S.C. 154(b) by 546 days.

(21) Appl. No.: 13/163,192

(22) Filed: Jun. 17, 2011

(65) Prior Publication Data
US 2011/0319277 A1    Dec. 29, 2011

Related U.S. Application Data

(60) Provisional application No. 61/356,554, filed on Jun. 18, 2010.

(51) Int. Cl.
C12Q 1/48    (2006.01)

(52) U.S. Cl.
CPC ............ *C12Q 1/485* (2013.01); *G01N 2500/02* (2013.01)

(58) Field of Classification Search
USPC .................................................. 435/7.4, 15
See application file for complete search history.

(56) References Cited

U.S. PATENT DOCUMENTS

| | | |
|---|---|---|
| 2006/0211728 A1 | 9/2006 | Greig et al. |
| 2007/0134261 A1 | 6/2007 | Hancock et al. |
| 2007/0208057 A1 | 9/2007 | Zeldis |

OTHER PUBLICATIONS

International Search Report, PCT/US11/40918, published on Dec. 22, 2011 under WO2011/160042, mailed on Apr. 9, 2012.
Written Opinion, PCT/US11/40918, published on Dec. 22, 2011 under WO2011/160042, mailed on Apr. 9, 2012.
Abe et al., "A Small Ras-like protein Ray/Rab1c modulates the p53-regulating activity of PRPK," Biochemical and Biophysical Research Communications, 2006, 244:377-385, Abstract, p. 377, col. 1, p. 379, col. 2, Fig. 3A, p. 382, col. 1.
Haslett et al., "Thalidomide Stimulates T Cell Responses and Interleukin 12 Production in HIV-Infected Patients," AIDS Research and Human Retroviruses, 1999, 15(13):1169-1179; Abstract.
Miyoshi et al., "Identification of CGI-121, a novel PRPK (p53-related protein kinase)-binding protein," Biochemical and Biophysical Research Communications 2003, 303(2):399-405; Abstract, p. 402, Fig. 3, p. 404, col. 1.
Manning et al., "The Protein Kinase Complement of the Human Genome," Science 2002, 298:1912-1934; p. 1913, col. 1, p. 1915, last col.
Mao et al., "Atomic structure of the KEOPS complex: an ancient protein kinase-containing molecular machine," Mol Cell. Oct. 24, 2008; 32(2): 259-275. Abstract.
Abe et al., "Cloning and characterization of a p53-related protein kinase expressed in interleukin-2-activated cytotoxic T-cells, epithelial tumor cell lines, and the testes," The Journal of the Biological Chemistry 2001, 276(47):44003-44011; Abstract.
Kuprash et al., "Ablation of TNF or lymphotoxin signaling and the frequency of spontaneous tumors in p53-deficient mice," Cancer Letters 2008, 268:70-75; Abstract.
Farina et al., "Investigating the KEOPS/EKC complex function in *C. elegans*," International Worm Meeting 2007. [Retrieved from the internet Jan. 8, 2012: <http://www.citeulike.org/user/thegoose2/article/3333461>].
Downey et al., "A Genome-Wide Screen Identifies the Evolutionarily Conserved KEOPS Complex as a Telomere Regulator," Cell 2006, 124(6):1155-1168.
Facchin et al., "Functional homology between yeast piD261/Bud32 and human PRPK: both phosphorylate p53 and PRPK partially complements piD261/Bud32 deficiency," FEBS Lett. 2003, 549(1-3):63-66.
Vandermeeren et al. "Subcellular forms and biochemical events triggered in human cells by HCV polyprotein expression from a viral vector," Virology Journal 2008, 5:102.
Szilard et al., "Characterization of the Mammalian KEOPS Complex Fifth Canadian Symposium on Telomeres and Telomerase," Poster 14. [Retrieved from the internet Jan. 8, 2012: <http://www.telomerecanada.info/pdf/Programme%20Cdn%20Telo%202006.pdf>]; p. 60.
Peterson et al., "A Chemosensitization Screen Identifies TP53RK, a Kinase that Restrains Apoptosis after Mitotic Stress," Cancer Res Aug. 1, 2010, 70:6325.
Gerald Schmid, et al., "Advantage of a baculovirus expression system for protein-protein inter-action studies. Involvement of post-translational phosphorylation in the interaction between wt p53 protein and poly(ADP-ribose) polymerase-1", Acta Biochimca Polonica, XP-002693258, vol. 52, No. 3, 2005, pp. 713-719.
Adalberto Costessi, et al., "The Human EKC/KEOPS Complex is Recruited to Cullin2 Ubiquitin Ligases by the Human Tumour Antigen PRAME", PLoS One, vol. 7, No. 8, E42822, Aug. 2012, XP002693259, pp. 1-13.
International Search Report and Written Opinion issued Mar. 21, 2013 in PCT/JP2012/083169 filed on Dec. 14, 2012.
Kotoshiba et al., Molecular Dissection of the Interaction between p27 and Kip1 Ubiquitylation-promoting Complex, the Ubiquitin Ligase That Regulates Proteolysis of p27 in G1 Phase; JBC, vol. 280, No. 18, pp. 17694-17700, 2005.
Office Action issued May 8, 2015 in related U.S. Appl. No. 14/365,021, 15 pp.

*Primary Examiner* — Antonio Galisteo Gonzalez
(74) *Attorney, Agent, or Firm* — Oblon, McClelland, Maier & Neustadt, L.L.P.

(57) ABSTRACT

The present invention provides methods of identifying an agent that modulates PRPK, TPRKB, OSGEP, LAGE3 and its homologs, PRPK/TPRKB complex, and/or KEOPS complex. The present invention also provides compositions of such agents and methods of treating a disease, disorder, or condition associated with PRPK, TPRKB, OSGEP, LAGE3 and its homologs family (CT antigens), PRPK/TPRKB complex, and/or KEOPS complex using such an agent or composition.

13 Claims, 9 Drawing Sheets

| Designation | Structure | Jeko-1 growth inhibition IC$_{50}$ μM | NCI-H929 growth inhibition IC$_{50}$ μM | Jurkat IL-2 production EC$_{50}$ μM |
|---|---|---|---|---|
| lenalidomide | 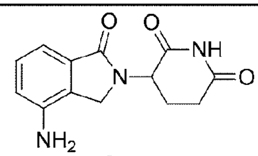 | 0.2 | 0.2 | 0.06 |
| pomalidomide | 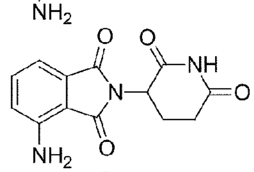 | 0.1 | 0.1 | 0.08 |
| thalidomide | 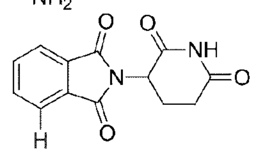 | inactive | inactive | inactive |
| CMPD 29 | 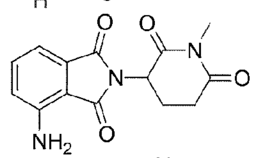 | 1.5 | 1.8 | 0.7 |
| CMPD 30 | 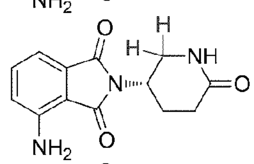 | inactive | inactive | inactive |
| CMPD 31 | 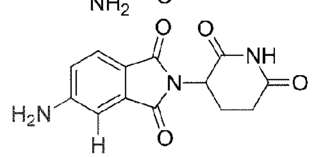 | inactive | inactive | inactive |

Figure 1

PRPK-TPRKB MODULATORS AND USES THEREOF

CROSS-REFERENCE TO RELATED APPLICATIONS

The present application claims the benefit of U.S. provisional patent application No. 61/356,554, filed Jun. 18, 2010, the entire contents of which are incorporated herein by reference.

BACKGROUND OF THE INVENTION

Revlimid® (lenalidomide) is an FDA-approved small molecule drug developed and marketed by Celgene for the treatment of multiple myeloma (MM) in combination with dexamethasone and for the treatment of myelodysplastic syndromes in patients with a specific 5q chromosomal deletion. The cellular target and mechanism of action of Revlimid® are unknown in the art. In 2009, sales of Revlimid® reached USD $ 1.7 billion and sales in 2010 are expected to exceed USD $2.0 billion, making Revlimid® one of the most successful oncology products introduced into commerce in the past five years. Based on this demonstrated commercial success and the absence of any FDA-approved competitive therapeutic drugs with a similar mechanism of action, the potential economic value of the demonstrated anti-cancer target(s) of Revlimid® (lenalidomide) is considerable.

Revlimid® belongs to a class of compounds referred to as immunomodulatory drugs (IMiDs) that include the analogs thalidomide (FDA-approved for MM and leprosy) and pomalidomide (Actimid™, under development by Celgene). Thomson Pharma has projected that annual Revlimid® drug sales could reach USD $3.8 billion by 2013. Because of thalidomide's well-known teratogenic effects, Revlimid® is sold under an FDA-mandated risk mitigation program with a 'Black Box Warning' describing the risks of birth defects. Recently, the protein target responsible for the teratogenicity of thalidomide was published as Cereblon (CRBN) (Ito et al, Science 327:1345-1350 (2010)); however, the anticancer target(s) of IMiD's are still unknown.

SUMMARY OF THE INVENTION

The present invention encompasses the recognition that compounds such as lenalidomide, pomalidomide, and thalidomide interact with a PRPK/TPRKB complex in order to affect their activities. The present invention further encompasses the recognition that PRPK/TPRKB interacts with OSGEP and LAGE3 and its homologs to form a human KEOPS complex. The inventors have surprisingly discovered that modulation of a PRPK/TPRKB complex, a KEOPS complex, or any subunit thereof is useful in treating a variety of diseases, disorders, or conditions.

The present invention provides methods of identifying an agent that interacts with (e.g., modulates) a PRPK/TPRKB complex comprising providing a system comprising PRPK and TPRKB, providing one or more test agents, contacting the one or more test agents with the system, and detecting an interaction between at least one of the test agents and at least one of PRPK and TPRKB. In some embodiments, the present invention provides methods of identifying an agent that interacts with (e.g., modulates) a KEOPS complex comprising providing a system comprising PRPK (also known as TP53RK), TPRKB, OSGEP, and LAGE3 and its homologs, providing one or more test agents, contacting the one or more test agents with the system, and detecting an interaction between at least one of the test agents and at least one of PRPK, TPRKB, OSGEP, and LAGE3 and its homologs. In some embodiments, the present invention provides methods of identifying an agent that interacts with (e.g., modulates) PRPK, TPRKB, OSGEP, or LAGE3 and its homologs comprising providing a system comprising PRPK, TPRKB, OSGEP, or LAGE3 and its homologs, providing one or more test agents, contacting the one or more test agents with the system, and detecting an interaction between at least one of the test agents and PRPK, TPRKB, OSGEP, or LAGE3 and its homologs. In some embodiments, any such method of identifying an agent comprises providing a plurality of test agents. In some embodiments, two or more test agent members of such a plurality share at least one common structural element or moiety. In some embodiments, two or more test agent members of such a plurality share a core structure element.

In some embodiments, PRPK, TPRKB, OSGEP, LAGE3 and its homologs, PRPK/TPRKB complex or KEOPS complex as described herein is human PRPK, human TPRKB, human OSGEP, human LAGE3 and its homologs, human PRPK/TPRKB, or human KEOPS complex.

In some embodiments, a test agent modulates PRPK, TPRKB, OSGEP, LAGE3 and its homologs, PRPK/TPRKB complex and/or KEOPS complex but does not modulate CRBN.

The present invention also provides modulators of a PRPK/TPRKB complex and/or modulators of a KEOPS complex and/or any subunit or component thereof. In some embodiments, a modulator according to the present invention is an agent discovered to modulate a PRPK/TPRKB complex and/or or modulators of a KEOPS complex and/or any subunit or component thereof using the methods described herein. In some embodiments, a modulator according to the present invention has a structure of formula I:

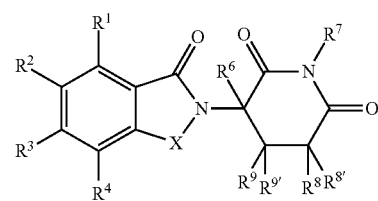

wherein X, $R^1$, $R^2$, $R^3$, $R^4$, $R^5$, $R^6$, $R^7$, $R^8$, $R^{8'}$, $R^9$, and $R^{9'}$ are as defined and described herein. In some embodiments, a modulator according to the present invention has a structure of formula II:

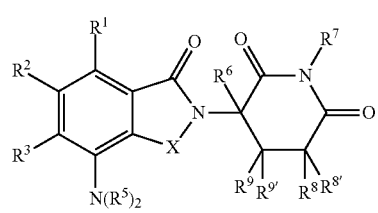

wherein X, $R^1$, $R^2$, $R^3$, $R^5$, $R^6$, $R^7$, $R^8$, $R^{8'}$, $R^9$, and $R^{9'}$ are as defined and described herein. In some embodiments, a modulator according to the present invention has a structure of formula III:

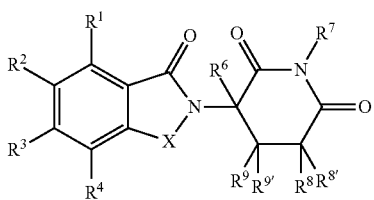

wherein X, $R^1$, $R^2$, $R^3$, $R^4$, $R^5$, $R^6$, $R^7$, $R^8$, $R^{8'}$, $R^9$, and $R^{9'}$ are as defined and described herein.

In some embodiments, the present invention provides methods of inhibiting cell proliferation comprising contacting a cell with an agent that modulates a PRPK/TPRKB complex and/or a KEOPS complex and/or any subunit or component thereof, and optionally further comprising a step of detecting a decrease in cell proliferation compared to a control. In some embodiments, the present invention provides methods of inhibiting B cell proliferation comprising contacting a B cell with an agent that modulates a PRPK/TPRKB complex and/or a KEOPS complex and/or any subunit or component thereof, and optionally further comprising a step of detecting a decrease in B cell proliferation compared to a control. In some embodiments, the present invention provides methods of inducing IL-2 production comprising contacting a cell with an agent that modulates a PRPK/TPRKB complex and/or a KEOPS complex and/or any subunit or component thereof, and optionally further comprising a step of detecting an increase in IL-2 production compared to a control. In some embodiments, the present invention provides methods of inhibiting or activating TNF-α production comprising contacting a cell with an agent that modulates a PRPK/TPRKB complex and/or a KEOPS complex and/or any subunit or component thereof, and optionally further comprising a step of detecting a decrease in TNF-α production compared to a control.

The present invention also provides methods and reagents, including compounds and/or compositions, useful in medicine. In some embodiments, the present invention provides methods of treating a disease, disorder, or condition associated with a PRPK/TPRKB complex and/or a KEOPS complex and/or any subunit or component thereof. In some embodiments, the present invention provides a method of treating inflammation, inflammatory disease or autoimmune disease comprising administering to a mammal in need of treatment an effective amount of at least one modulator of a PRPK/TPRKB complex and/or a KEOPS complex and/or any subunit or component thereof. In some embodiments, the present invention provides a method of treating an oncogenic or cancerous condition comprising administering to a mammal in need of treatment an effective amount of at least one modulator of a PRPK/TPRKB complex and/or a KEOPS complex and/or any subunit or component thereof.

This application refers to various patent publications, all of which are incorporated herein by reference.

BRIEF DESCRIPTION OF THE DRAWINGS

FIG. 1. Activities of exemplary test agents in growth inhibition and IL-2 production assays.

DEFINITIONS

Figure 2:
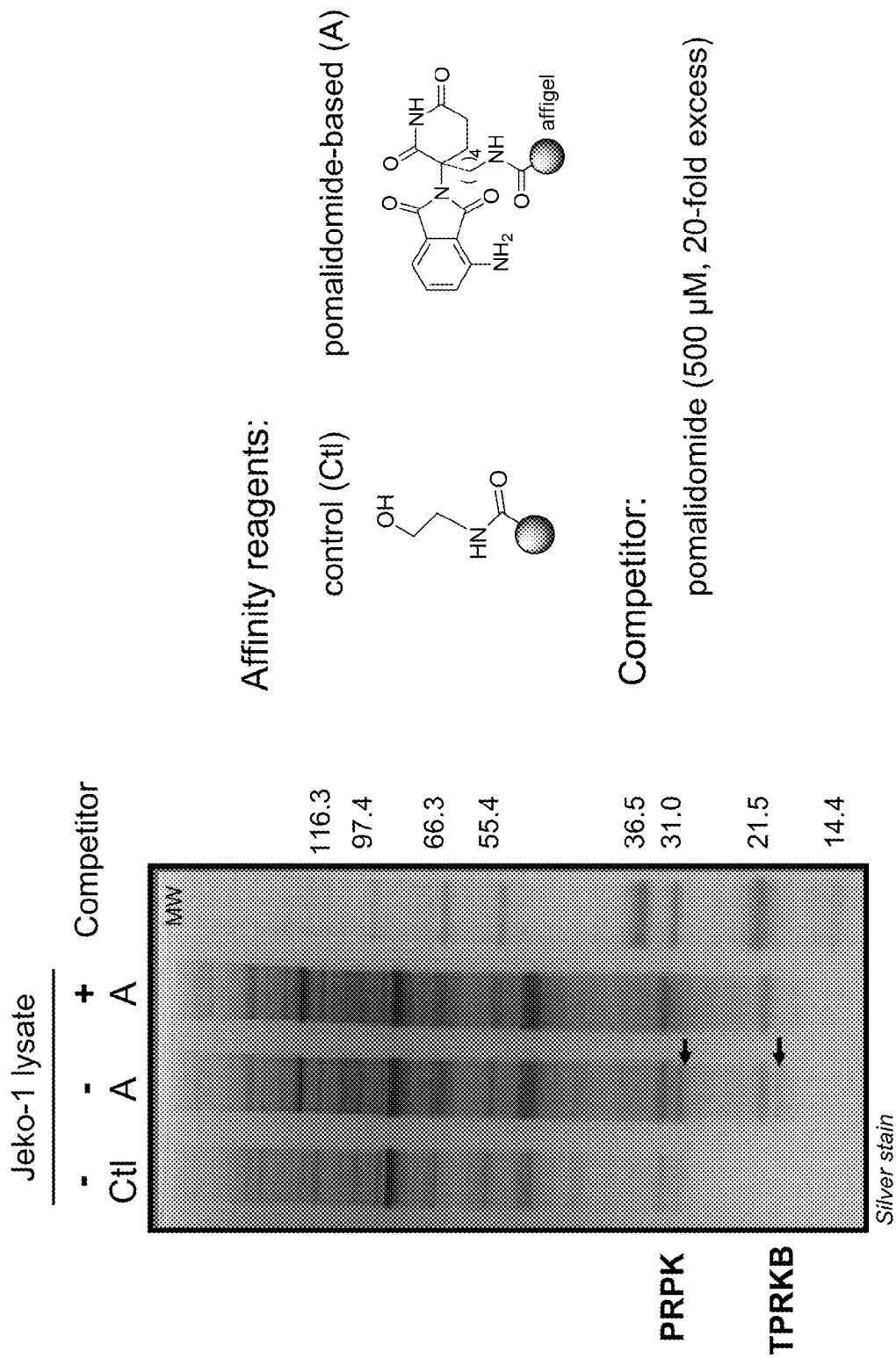
FIG. 2. PRPK and TPRKB captured with pomalidomide-based affinity reagent. PRPK and TPRKB were only captured from sensitive cell lines (Jurkat, Jeko-1, HS-Sultan); PRPK and TPRKB were not captured from HeLa S3 cells.

Amino acid: As used herein, the term "amino acid," in its broadest sense, refers to any compound and/or substance that can be incorporated into a polypeptide chain. In some embodiments, an amino acid has the general structure $H_2N$—$C(H)(R)$—$COOH$. In some embodiments, an amino acid is a naturally-occurring amino acid. In some embodiments, an amino acid is a synthetic or un-natural amino acid; in some embodiments, an amino acid is a D-amino acid (e.g., α,α-disubstituted amino acids, N-alkyl amino acids, lactic acid); in some embodiments, an amino acid is an L-amino acid. "Standard amino acid" refers to any of the twenty standard L-amino acids commonly found in naturally occurring peptides. "Nonstandard or unconventional amino acid" refers to any amino acid, other than the standard amino acids, regardless of whether it is prepared synthetically or obtained from a natural source. As used herein, "synthetic or un-natural amino acid" encompasses chemically modified amino acids, including but not limited to salts, amino acid derivatives (such as amides), and/or substitutions. Amino acids, including carboxy- and/or amino-terminal amino acids in peptides, can be modified by methylation, amidation, acetylation, and/or substitution with other chemical groups that can change the peptide's circulating half-life without adversely affecting its activity. Examples of unconventional or un-natural amino acids include, but are not limited to, citrulline, ornithine, norvaline, 4-(E)-butenyl-4(R)-methyl-N-methylthreonine (MeBmt), N-methyl-leucine (MeLeu), aminoisobutyric acid, statine, and N-methyl-alanine (MeAla) Amino acids may participate in a disulfide bond. The term "amino acid" is used interchangeably with "amino acid residue," and may refer to a free amino acid and/or to an amino acid residue of a peptide. It will be apparent from the context in which the term is used whether it refers to a free amino acid or a residue of a peptide.

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically-engineered animal, and/or a clone.

Antibody: As used herein, the term "antibody" refers to any immunoglobulin, whether natural or wholly or partially synthetically produced. All derivatives thereof which maintain specific binding ability are also included in the term. The term also covers any protein having a binding domain which is homologous or largely homologous to an immunoglobulin binding domain. Such proteins may be derived from natural sources, or partly or wholly synthetically produced. An antibody may be monoclonal or polyclonal. An antibody may be a member of any immunoglobulin class, including any of the human classes: IgG, IgM, IgA, IgD, and IgE. As used herein, the terms "antibody fragment" or "characteristic portion of an antibody" are used interchangeably and refer to any derivative of an antibody which is less than full-length. In general, an antibody fragment retains at least a significant portion of the full-length antibody's specific binding ability. Examples of antibody fragments include, but are not limited to, Fab, Fab', F(ab')2, scFv, Fv, dsFv diabody, and Fd fragments. An antibody fragment may be produced by any means. For example, an antibody fragment may be enzymatically or chemically produced by fragmentation of an intact antibody and/or it may be recombinantly produced from a gene encoding the partial antibody sequence. Alternatively or additionally, an antibody fragment may be wholly or partially synthetically produced. An antibody fragment may optionally comprise a single chain antibody fragment. Alternatively or additionally, an antibody fragment may comprise multiple chains which are linked together, for example, by disulfide linkages. An antibody fragment may optionally comprise a multimolecular complex. A functional antibody fragment typically comprises at least about 50 amino acids and more typically comprises at least about 200 amino acids.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Biologically active: As used herein, the phrase "biologically active" refers to a characteristic of any substance that has activity in a biological system and/or organism. For instance, a substance that, when administered to an organism, has a biological effect on that organism, is considered to be biologically active. In particular embodiments, where a protein or polypeptide is biologically active, a portion of that protein or polypeptide that shares at least one biological activity of the protein or polypeptide is typically referred to as a "biologically active" portion.

Biological target: As used herein, the term "biological target" refers to any target that may be utilized in the systems, methods, assays, and/or compositions described herein. A "biological target" may refer to one or more of the following: (1) a PRPK protein, a nucleic acid encoding PRPK, and/or homolog, portion, variant, mutant, and/or derivative thereof; (2) a TPRKB protein, a nucleic acid encoding TPRKB, and/or homolog, portion, variant, mutant, and/or derivative thereof; (3) a OSGEP protein, a nucleic acid encoding OSGEP, and/or homolog, portion, variant, mutant, and/or derivative thereof; (4) a LAGE3 and its homologs protein, a nucleic acid encoding LAGE3 and its homologs, and/or homolog, portion, variant, mutant, and/or derivative thereof; and/or (5) a complex of any two or more of PRPK, TPRKB, OSGEP, and/or LAGE3 and its homologs.

Characteristic portion: As used herein, the phrase a "characteristic portion" of a substance, in the broadest sense, is one that shares some degree of sequence and/or structural identity and/or at least one functional characteristic with the relevant intact substance. For example, a "characteristic portion" of a protein or polypeptide is one that contains a continuous stretch of amino acids, or a collection of continuous stretches of amino acids, that together are characteristic of a protein or polypeptide. In some embodiments, each such continuous stretch generally will contain at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 29, 40, 41, 42, 43, 44, 45, 46, 47, 48, 49, 50 or more amino acids. In general, a characteristic portion is one that, in addition to the sequence identity specified above, shares at least one functional characteristic with the relevant intact protein. In some embodiments, the characteristic portion may be biologically active and/or may confer biological activity onto a polypeptide in which it is included.

Control: As used herein, the term "control" has its art-understood meaning of being a standard against which results are compared. Typically, controls are used to augment integrity in experiments by isolating variables in order to make a conclusion about such variables. In some embodiments, a control is a reaction or assay that is performed simultaneously with a test reaction or assay to provide a comparator. In one experiment, the "test" (i.e., the variable being tested) is applied. In the second experiment, the "control," the variable being tested is not applied. In some embodiments, a control is a historical control (i.e., of a test or assay performed previously, or an amount or result that is previously known). In some embodiments, a control is or comprises a printed or otherwise saved record. A control may be a positive control or a negative control.

Core structure element: As used herein, the term "core structure element" refers to a feature or collection of features of a molecule that represents specific characteristics responsible for biological activity or lack thereof. For example, test agents that contain an isoindolinone moiety can be said to share a core structure element. A core structure element may be, e.g., a ring system, or a core structure element may be, e.g., a linear structure that is similar in length and atom identity.

Engineered: In general, the term "engineered" refers to the aspect of having been manipulated by the hand of man. For example, a polynucleotide is considered to be "engineered" when two or more sequences, that are not linked together in that order in nature, are manipulated by the hand of man to be directly linked to one another in the engineered polynucleotide. For example, in some embodiments of the present invention, an engineered polynucleotide comprises a regulatory sequence that is found in nature in operative association with a first coding sequence but not in operative association with a second coding sequence, is linked by the hand of man so that it is operatively associated with the second coding sequence.

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, and/or 3' end formation); (3) translation of an RNA into a polypeptide or protein; (4) post-translational modification of a polypeptide or protein.

Heterologous: The term "heterologous", as used herein to refer to nucleic acids (e.g., nucleic acids including regulatory sequences and/or genes) or polypeptides, refers to a nucleic acid or polypeptide that is artificially introduced into a cell and/or does not naturally occur in the cell in which it is present. In some embodiments, a heterologous nucleic acid has a nucleotide sequence that is identical to that of a nucleic acid naturally present in the cell. In many embodiments a heterologous nucleic acid has a nucleotide sequence that is different from that of any nucleic acid that is naturally present in the cell. In some embodiments, a nucleic acid that is heterologous to a particular cell has a nucleic acid sequence that is identical to that of a nucleic acid that is naturally found in a source organism that is different from the cell into which the heterologous nucleic acid is introduced.

Host cell: As used herein, the "host cell" is a cell that is manipulated according to the present disclosure. A "modified host cell", as used herein, is any host cell which has been modified, engineered, or manipulated in accordance with the present disclosure as compared with an otherwise identical parental cell, and/or as compared with a particular reference cell (e.g., a wild type cell).

Introduce: The term "introduce", as used herein with reference to introduction of a nucleic acid into a cell or organism is intended to have its broadest meaning and to encompass introduction, for example by transformation methods (e.g., calcium-chloride-mediated transformation, electroporation, particle bombardment), and also introduction by other methods including transduction, conjugation, and mating. In some embodiments, a vector is utilized to introduce a nucleic acid into a cell or organism.

In vitro: As used herein, the term "in vitro" refers to events that occur in an artificial environment, e.g., in a test tube or reaction vessel, in cell culture, etc., rather than within a multi-cellular organism.

In vivo: As used herein, the term "in vivo" refers to events that occur within a multi-cellular organism such as a non-human animal.

Isolated: As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from at least about 10%, about 20%, about 30%, about 40%, about 50%, about 60%, about 70%, about 80%, about 90%, about 95%, about 98%, about 99%, substantially 100%, or 100% of the other components with which they were initially associated. In some embodiments, isolated agents are more than about 80%, about 85%, about 90%, about 91%, about 92%, about 93%, about 94%, about 95%, about 96%, about 97%, about 98%, about 99%, substantially 100%, or 100% pure. As used herein, a substance is "pure" if it is substantially free of other components. As used herein, the term "isolated cell" refers to a cell not contained in a multi-cellular organism.

Modified: The term "modified" may be used herein to refer to an entity (e.g., a cell or organism) that has been manipulated by the hand of man. For example, in some embodiments, a modification may be or comprise any chemical, physiological, genetic, or other modification that appropriately alters characteristics of a host organism as compared with an otherwise identical reference organism not subjected to the modification. In most embodiments, a modification will comprise a genetic modification. In some embodiments, a modification comprises at least one chemical, physiological, genetic, or other modification; in some embodiments a modification comprises more than one chemical, physiological, genetic, or other modification. In certain aspects where more than one modification is utilized, such modifications can comprise any combination of chemical, physiological, genetic, or other modification (e.g., one or more genetic, chemical and/or physiological modification(s)).

Modulator: As used herein, the term "modulator" typically refers to a compound that alters or elicits an activity. For example, the presence of a modulator may result in an increase or decrease in the magnitude of a certain activity compared to the magnitude of the activity in the absence of the modulator. In certain embodiments, a modulator is an inhibitor or antagonist, which decreases the magnitude of one or more activities. In certain embodiments, an inhibitor completely prevents one or more biological activities. In certain embodiments, a modulator is an activator or agonist, which increases the magnitude of at least one activity. In certain embodiments the presence of a modulator results in an activity that does not occur in the absence of the modulator. As used herein, the terms "inhibiting," "reducing," "preventing," or "antagonizing," or any variations of these terms as used herein, refer to a measurable decrease of a biological activity. In some embodiments, the decrease is a 10%, 15%, 20%, 30%, 40%, 50%, 60%, 70%, 80%, 90%, 95%, or 99% reduction in the biological activity relative to a control. As used herein, the terms "stimulating," "increasing," or "agonizing," or any variations of these terms as used herein, refer to a measurable increase of a biological activity. In some embodiments, the increase is a 10%, 15%, 20%, 30%, 40%, 50%, 60%, 70%, 80%, 90%, 95%, or 99% increase in the biological activity relative to a control. A modulator can also be a "silent modulator", wherein the modulator interacts with (e.g., binds to) the target of interest but does not elicit or alter an activity of the target.

Natural product: As used herein, the term "natural product" refers to a chemical compound or substance that is or can be produced by a living organism. In some embodiments, a natural product is not a biopolymer such as a polynucleotide, peptide or polypeptide, or oligosachamide. A compounds that is structurally identical to a natural product can be referred to as a "natural product" even if the compound itself is in fact prepared by the hand of man (e.g., by chemical synthesis).

Nucleic acid: As used herein, the term "nucleic acid," in its broadest sense, refers to any compound and/or substance that can be incorporated into an oligonucleotide chain. In some embodiments, "nucleic acid" encompasses RNA as well as single and/or double-stranded DNA and/or cDNA. Furthermore, the terms "nucleic acid," "DNA," "RNA," and/or similar terms include nucleic acid analogs, i.e. analogs having other than a phosphodiester backbone. For example, the so-called "peptide nucleic acids," which are known in the art and have peptide bonds instead of phosphodiester bonds in the backbone, are considered within the scope of the present invention. The term "nucleotide sequence encoding an amino acid sequence" includes all nucleotide sequences that are degenerate versions of each other and/or encode the same amino acid sequence. Nucleotide sequences that encode proteins and/or RNA may include introns.

Peptide: As used herein, the term "peptide" or "polypeptide" refers to a macromolecule which comprises a multiplicity of amino or imino acids (or their equivalents) in peptide linkage. In the polypeptide or peptide notation used herein, the left-hand direction is the amino-terminal direction and the right-hand direction is the carboxy-terminal direction, in accordance with standard usage and convention. Peptides may include moieties other than amino acids (e.g., may be glycoproteins, proteoglycans, etc.) and/or may be otherwise processed or modified. Peptides may contain L-amino acids, D-amino acids, or both and may contain any of a variety of amino acid modifications or analogs known in the art. Useful modifications include, e.g., terminal acetylation, amidation, etc. In some embodiments, peptides may comprise natural amino acids, non-natural amino acids, synthetic amino acids, and combinations thereof. In some embodiments, peptides may contain up to 25 amino acids. As used herein, peptides containing up to 25 amino acids are also referred to as short peptides. The term "peptide" or "polypeptide" is also used to refer to specific functional classes of polypeptides, such as, for example, desaturases, elongases, etc. Those of ordinary skill in the art will appreciate that the term "polypeptide" is intended to be sufficiently general as to encompass not only polypeptides having the complete sequence recited herein (or in a reference or database specifically mentioned herein), but also to encompass polypeptides that represent functional fragments (i.e., fragments retaining at least one activity) of such complete polypeptides. Moreover, those of ordinary skill in the art understand that protein sequences generally tolerate some substitution without destroying activity. Thus, any polypeptide that retains activity and shares at least about 30-40% overall sequence identity, often greater than about 50%, 60%, 70%, or 80%, and further usually including at least one region of much higher identity, often greater than 90% or even 95%, 96%, 97%, 98%, or 99% in one or more highly conserved regions, usually encompassing at least 3-4 and often up to 20 or more amino acids, with another polypeptide of the same class, is encompassed within the relevant term "polypeptide" as used herein. Other regions of similarity and/or identity can be determined by those of ordinary skill in the art by analysis of the sequences of various polypeptides described herein. As is known by those of ordinary skill in the art, a variety of strategies are known, and tools are available, for performing comparisons of amino acid or nucleotide sequences in order to assess degrees of identity and/or similarity. These strategies include, for example, manual alignment, computer assisted sequence alignment and combinations thereof. A number of algorithms (which are generally computer implemented) for performing sequence alignment are widely available, or can be produced by one of skill in the art. Representative algorithms include, e.g., the local homology algorithm of Smith and Waterman (Adv. Appl. Math., 1981, 2: 482); the homology alignment algorithm of Needleman and Wunsch (J. Mol. Biol., 1970, 48: 443); the search for similarity method of Pearson and Lipman (Proc. Natl. Acad. Sci. (USA), 1988, 85: 2444); and/or by computerized implementations of these algorithms (e.g., GAP, BESTFIT, FASTA, and TFASTA in the Wisconsin Genetics Software Package Release 7.0, Genetics Computer Group, 575 Science Dr., Madison, Wis.). Readily available computer programs incorporating such algorithms include, for example, BLASTN, BLASTP, Gapped BLAST, PILEUP, CLUSTALW, etc. When utilizing BLAST and Gapped BLAST programs, default parameters of the respective programs may be used. Alternatively, the practitioner may use non-default parameters depending on his or her experimental and/or other requirements (see for example, ncbi.nlm.nih gov).

Pure: As used herein, a substance and/or entity is "pure" if it is substantially free of other components. For example, a preparation that contains more than about 90% of a particular substance and/or entity is typically considered to be a pure preparation. In some embodiments, a substance and/or entity is at least 91%, 92%, 93%, 94%, 95%, 96%, 97%, 98%, or 99% pure.

Reference agent: The term "reference agent," as used herein, refers to a substance (e.g., a chemical compound, small molecule, natural product, protein, peptide, nucleic acid) that has a known activity in a particular assay. A reference agent may also be referred to as a "standard." A reference agent may be a positive standard, showing positive activity in a particular assay, or may be a negative standard, known to be inactive in a particular assay. A reference agent may be contemporaneous to an agent of interest or may be a historical standard. In certain embodiments, a test agent and a reference agent are evaluated under comparable assay conditions.

Small molecule: In general, a "small molecule" is understood in the art to be an organic molecule that is less than about 5 kilodaltons (Kd) in size. In some embodiments, the small molecule is less than about 4 Kd, about 3 Kd, about 2 Kd, or about 1 Kd. In some embodiments, the small molecule is less than about 800 daltons (D), about 600 D, about 500 D, about 400 D, about 300 D, about 200 D, or about 100 D. In some embodiments, a small molecule is less than about 2000 g/mol, less than about 1500 g/mol, less than about 1000 g/mol, less than about 800 g/mol, or less than about 500 g/mol. In some embodiments, small molecules are non-polymeric. In some embodiments, small molecules are not proteins, peptides, or amino acids. In some embodiments, small molecules are not nucleic acids or nucleotides. In some embodiments, small molecules are not saccharides or polysaccharides.

Source organism: A "source organism", as that term is used herein, is an organism that naturally contains or produces a polynucleotide, polypeptide, or other compound (e.g., a heterologous nucleic acid) that is to be introduced in accordance with the present invention into a recipient or host cell. In some embodiments, the particular source organism to be selected is not essential to the practice of the present disclosure. Relevant considerations may include, for example, how closely related the potential source and host organisms are in evolution, or how related the source organism is with other source organisms from which sequences of other relevant nucleic acids and/or polypeptides have been selected. Where a plurality of different heterologous nucleic acids are to be introduced into and/or expressed by a host cell, different sequences may be from different source organisms, or from the same source organism. To give but one example, in some cases, individual polypeptides may represent individual subunits of a complex protein activity and/or may be required to work in concert with other polypeptides in order to achieve the goals of the present disclosure. In some embodiments, it will often be desirable for such polypeptides to be from the same source organism, and/or to be sufficiently related to function appropriately when expressed together in a host cell. In some embodiments, such polypeptides may be from different, even unrelated source organisms. It will further be understood that, where a heterologous polypeptide is to be expressed in a host cell, it will often be desirable to utilize nucleic acid sequences encoding the polypeptide that have been adjusted to accommodate codon preferences of the host cell and/or to link the encoding sequences with regulatory elements active in the host cell. In certain embodiments, a gene sequence encoding a given polypeptide is optimized even when such a gene sequence is derived from the host cell itself (and thus is not heterologous). For example, a gene sequence encoding a polypeptide of interest may not be codon optimized for expression in a given host cell even though such a gene sequence is isolated from the host cell strain. In such embodiments, the gene sequence may be further optimized to account for codon preferences of the host cell. Those of ordinary skill in the art will be aware of host cell codon preferences and will be able to employ the methods and reagents described herein and/or known in the art to accommodate them.

Subject: As used herein, the term "subject" or "patient" refers to any organism to which agents or compositions in accordance with the invention may be administered, e.g., for experimental, diagnostic, prophylactic, and/or therapeutic purposes. Typical subjects include animals (e.g., mammals such as mice, rats, rabbits, non-human primates, and humans; insects; worms; etc.).

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Suffering from: An individual who is "suffering from" a disease, disorder, and/or condition has been diagnosed with or displays one or more symptoms of the disease, disorder, and/or condition.

Susceptible to: An individual who is "susceptible to" a disease, disorder, and/or condition has not been diagnosed with the disease, disorder, and/or condition. In some embodiments, an individual who is susceptible to a disease, disorder, and/or condition may not exhibit symptoms of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Therapeutic agent: As used herein, the phrase "therapeutic agent" refers to any agent that, when administered to a subject, has a therapeutic effect and/or elicits a desired biological and/or pharmacological effect. In some embodiments, a therapeutic agent of the invention refers to a peptide inhibitor or derivatives thereof according to the invention.

Therapeutic index: As used herein, the phrase "therapeutic index" refers to a quantitative measure of the selectivity of a drug when a therapeutic effect ("E") and a toxic effect ("T") are being compared. The therapeutic index can then be calculated as $ED_{50}/TD_{50}$, at some arbitrary level of response observed in a subject receiving the drug. The $ED_{50}$ is the dose required to generate the desired intensity of therapeutic effect in 50% of the subjects tested. The $TD_{50}$ is the dose required to generate the toxic effect in 50% of the subjects tested.

Treating: As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease.

Vector: As used herein, "vector" refers to a nucleic acid molecule capable of transporting another nucleic acid to which it has been linked. In some embodiment, vectors are capable of extra-chromosomal replication and/or expression of nucleic acids to which they are linked in a host cell such as a eukaryotic and/or prokaryotic cell. Vectors capable of directing the expression of operatively linked genes are referred to herein as "expression vectors."

Definitions of specific functional groups, chemical terms, and general terms used throughout the specification are described in more detail below. For purposes of this invention, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March March's Advanced Organic Chemistry, 5$^{th}$ Edition, John Wiley & Sons, Inc., New York, 2001; Larock, Comprehensive Organic Transformations, VCH Publishers, Inc., New York, 1989; Carruthers, Some Modem Methods of Organic Synthesis, 3$^{rd}$ Edition, Cambridge University Press, Cambridge, 1987.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention.

Where a particular enantiomer is preferred, it may, in some embodiments be provided substantially free of the corresponding enantiomer, and may also be referred to as "optically enriched." "Optically-enriched," as used herein, means that the compound is made up of a significantly greater proportion of one enantiomer. In certain embodiments the compound is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques et al., *Enantiomers, Racemates and Resolutions* (Wiley Interscience, New York, 1981); Wilen, et al., *Tetrahedron* 33:2725 (1977); Eliel, E. L. *Stereochemistry of Carbon Compounds* (McGraw-Hill, N.Y., 1962); Wilen, S. H. *Tables of Resolving Agents and Optical Resolutions* p. 268 (E. L. Eliel, Ed., Univ. of Notre Dame Press, Notre Dame, Ind. 1972).

Acyl—As used herein, the term "acyl," refers to a group having the general formula —C(=O)R$^{X1}$, —C(=O)OR$^{X1}$, —C(=O)—O—C(=O)R$^{X1}$, —C(=O)SR$^{X1}$, —C(=O)N(R$^{X1}$)$_2$, —C(=S)R$^{X1}$, —C(=S)N(R$^{X1}$)$_2$, and —C(=S)S(R$^{X1}$), —C(=NR$^{X1}$)R$^{X1}$, —C(=NR$^{X1}$)OR$^{X1}$, —C(=NR$^{X1}$)SR$^{X1}$, and —C(=NR$^{X1}$)N(R$^{X1}$)$_2$, wherein R$^{X1}$ is hydrogen; halogen; substituted or unsubstituted hydroxyl; substituted or unsubstituted thiol; substituted or unsubstituted amino; substituted or unsubstituted acyl; cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl, substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two $R^{X1}$ groups taken together form a 5- to 6-membered heterocyclic ring. Exemplary acyl groups include aldehydes (—CHO), carboxylic acids (—$CO_2H$), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

Aliphatic—As used herein, the term "aliphatic" or "aliphatic group" denotes an optionally substituted hydrocarbon moiety that may be straight-chain (i.e., unbranched), branched, or cyclic ("carbocyclic") and may be completely saturated or may contain one or more units of unsaturation, but which is not aromatic. Unless otherwise specified, aliphatic groups contain 1-12 carbon atoms. In some embodiments, aliphatic groups contain 1-6 carbon atoms. In some embodiments, aliphatic groups contain 1-4 carbon atoms, and in yet other embodiments aliphatic groups contain 1-3 carbon atoms. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

Alkenyl—As used herein, the term "alkenyl" denotes an optionally substituted monovalent group derived from a straight- or branched-chain aliphatic moiety having at least one carbon-carbon double bond by the removal of a single hydrogen atom. In certain embodiments, the alkenyl group employed in the invention contains 2-6 carbon atoms. In certain embodiments, the alkenyl group employed in the invention contains 2-5 carbon atoms. In some embodiments, the alkenyl group employed in the invention contains 2-4 carbon atoms. In another embodiment, the alkenyl group employed contains 2-3 carbon atoms. Alkenyl groups include, for example, ethenyl, propenyl, butenyl, 1-methyl-2-buten-1-yl, and the like.

Alkyl—As used herein, the term "alkyl" refers to optionally substituted saturated, straight- or branched-chain hydrocarbon radicals derived from an aliphatic moiety containing between 1-6 carbon atoms by removal of a single hydrogen atom. In some embodiments, the alkyl group employed in the invention contains 1-5 carbon atoms. In another embodiment, the alkyl group employed contains 1-4 carbon atoms. In still other embodiments, the alkyl group contains 1-3 carbon atoms. In yet another embodiment, the alkyl group contains 1-2 carbons. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like.

Alkynyl—As used herein, the term "alkynyl" refers to an optionally substituted monovalent group derived from a straight- or branched-chain aliphatic moiety having at least one carbon-carbon triple bond by the removal of a single hydrogen atom. In certain embodiments, the alkynyl group employed in the invention contains 2-6 carbon atoms. In certain embodiments, the alkynyl group employed in the invention contains 2-5 carbon atoms. In some embodiments, the alkynyl group employed in the invention contains 2-4 carbon atoms. In another embodiment, the alkynyl group employed contains 2-3 carbon atoms. Representative alkynyl groups include, but are not limited to, ethynyl, 2-propynyl (propargyl), 1-propynyl, and the like.

Aryl—As used herein, the term "aryl" used alone or as part of a larger moiety as in "aralkyl", "aralkoxy", or "aryloxyalkyl", refers to an optionally substituted monocyclic and bicyclic ring systems having a total of five to 10 ring members, wherein at least one ring in the system is aromatic and wherein each ring in the system contains three to seven ring members. The term "aryl" may be used interchangeably with the term "aryl ring". In certain embodiments of the present invention, "aryl" refers to an aromatic ring system which includes, but not limited to, phenyl, biphenyl, naphthyl, anthracyl and the like, which may bear one or more substituents.

Arylalkyl—As used herein, the term "arylalkyl" refers to an alkyl group substituted with an aryl group (e.g., an aromatic or heteroaromatic group).

Bivalent hydrocarbon chain—As used herein, the term "bivalent hydrocarbon chain" (also referred to as a "bivalent alkylene group") is a polymethylene group, i.e., —$(CH_2)_z$—, wherein z is a positive integer from 1 to 30, from 1 to 20, from 1 to 12, from 1 to 8, from 1 to 6, from 1 to 4, from 1 to 3, from 1 to 2, from 2 to 30, from 2 to 20, from 2 to 10, from 2 to 8, from 2 to 6, from 2 to 4, or from 2 to 3. A substituted bivalent hydrocarbon chain is a polymethylene group in which one or more methylene hydrogen atoms are replaced with a substituent. Suitable substituents include those described below for a substituted aliphatic group.

Carbonyl—As used herein, the term "carbonyl" refers to a monovalent or bivalent moiety containing a carbon-oxygen double bond. Non-limiting examples of carbonyl groups include aldehydes, ketones, carboxylic acids, ester, amide, enones, acyl halides, anhydrides, ureas, carbamates, carbonates, thioesters, lactones, lactams, hydroxamates, isocyanates, and chloroformates.

Cycloaliphatic—As used herein, the terms "cycloaliphatic", "carbocycle", or "carbocyclic", used alone or as part of a larger moiety, refer to an optionally substituted saturated or partially unsaturated cyclic aliphatic monocyclic or bicyclic ring systems, as described herein, having from 3 to 10 members. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. In some embodiments, the cycloalkyl has 3-6 carbons.

Halogen—As used herein, the terms "halo" and "halogen" refer to an atom selected from fluorine (fluoro, —F), chlorine (chloro, —Cl), bromine (bromo, —Br), and iodine (iodo, —I).

Heteroaliphatic—As used herein, the terms "heteroaliphatic" or "heteroaliphatic group", denote an optionally substituted hydrocarbon moiety having, in addition to carbon atoms, from one to five heteroatoms, that may be straight-chain (i.e., unbranched), branched, or cyclic ("heterocyclic") and may be completely saturated or may contain one or more units of unsaturation, but which is not aromatic. Unless otherwise specified, heteroaliphatic groups contain 1-6 carbon atoms wherein 1-3 carbon atoms are optionally and independently replaced with heteroatoms selected from oxygen, nitrogen and sulfur. In some embodiments, heteroaliphatic groups contain 1-4 carbon atoms, wherein 1-2 carbon atoms are optionally and independently replaced with heteroatoms selected from oxygen, nitrogen and sulfur. In yet other embodiments, heteroaliphatic groups contain 1-3 carbon atoms, wherein 1 carbon atom is optionally and independently replaced with a heteroatom selected from oxygen, nitrogen and sulfur. Suitable heteroaliphatic groups include, but are not limited to, linear or branched, heteroalkyl, heteroalkenyl, and heteroalkynyl groups.

Heteroaralkyl—As used herein, the term "heteroaralkyl" refers to an alkyl group substituted by a heteroaryl, wherein the alkyl and heteroaryl portions independently are optionally substituted.

Heteroaryl—As used herein, the term "heteroaryl" used alone or as part of a larger moiety, e.g., "heteroaralkyl", or "heteroaralkoxy", refers to an optionally substituted group having 5 to 10 ring atoms, preferably 5, 6, or 9 ring atoms; having 6, 10, or 14 π electrons shared in a cyclic array; and having, in addition to carbon atoms, from one to five heteroatoms. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, carbocyclic, or heterocyclic rings, where the radical or point of attachment is on the heteroaromatic ring. Non limiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, and tetrahydroisoquinolinyl. A heteroaryl group may be mono- or bicyclic. The term "heteroaryl" may be used interchangeably with the terms "heteroaryl ring", "heteroaryl group", or "heteroaromatic", any of which terms include rings that are optionally substituted.

Heteroatom—As used herein, the term "heteroatom" refers to nitrogen, oxygen, or sulfur, and includes any oxidized form of nitrogen or sulfur, and any quaternized form of a basic nitrogen. The term "nitrogen" also includes a substituted nitrogen.

Heterocyclic—As used herein, the terms "heterocycle", "heterocyclyl", "heterocyclic radical", and "heterocyclic ring" are used interchangeably and refer to a stable optionally substituted 5- to 7-membered monocyclic or 7- to 10-membered bicyclic heterocyclic moiety that is either saturated or partially unsaturated, and having, in addition to carbon atoms, one or more heteroatoms, as defined above. A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or carbocyclic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

Unsaturated—As used herein, the term "unsaturated", means that a moiety has one or more double or triple bonds.

Partially unsaturated—As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

Optionally substituted—As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; $-(CH_2)_{0-4}R^\circ$; $-(CH_2)_{0-4}OR^\circ$; $-O-(CH_2)_{0-4}C(O)OR^\circ$; $-(CH_2)_{0-4}CH(OR^\circ)_2$; $-(CH_2)_{0-4}SR^\circ$; $-(CH_2)_{0-4}Ph$, which may be substituted with $R^\circ$; $-(CH_2)_{0-4}O(CH_2)_{0-1}Ph$ which may be substituted with $R^\circ$; $-CH=CHPh$, which may be substituted with $R^\circ$; $-NO_2$; $-CN$; $-N_3$; $-(CH_2)_{0-4}N(R^\circ)_2$; $-(CH_2)_{0-4}N(R^\circ)C(O)R^\circ$; $-N(R^\circ)C(S)R^\circ$; $-(CH_2)_{0-4}N(R^\circ)C(O)NR^\circ_2$; $-N(R^\circ)C(S)NR^\circ_2$; $-(CH_2)_{0-4}N(R^\circ)C(O)OR^\circ$; $-N(R^\circ)N(R^\circ)C(O)R^\circ$; $-N(R^\circ)N(R^\circ)C(O)NR^\circ_2$; $-N(R^\circ)N(R^\circ)C(O)OR^\circ$; $-(CH_2)_{0-4}C(O)R^\circ$; $-C(S)R^\circ$; $-(CH_2)_{0-4}C(O)OR^\circ$; $-(CH_2)_{0-4}C(O)SR^\circ$; $-(CH_2)_{0-4}C(O)OSiR^\circ_3$; $-(CH_2)_{0-4}OC(O)R^\circ$; $-OC(O)(CH_2)_{0-4}SR-$, $SC(S)SR^\circ$; $-(CH_2)_{0-4}SC(O)R^\circ$; $-(CH_2)_{0-4}C(O)NR^\circ_2$; $-C(S)NR^\circ_2$; $-C(S)SR^\circ$; $-SC(S)SR^\circ$, $-(CH_2)_{0-4}OC(O)NR^\circ_2$; $-C(O)N(OR^\circ)R^\circ$; $-C(O)C(O)R^\circ$; $-C(O)CH_2C(O)R^\circ$; $-C(NOR^\circ)R^\circ$; $-(CH_2)_{0-4}SSR^\circ$; $-(CH_2)_{0-4}S(O)_2R^\circ$; $-(CH_2)_{0-4}S(O)_2OR^\circ$; $-(CH_2)_{0-4}OS(O)_2R^\circ$; $-S(O)_2NR^\circ_2$; $-(CH_2)_{0-4}S(O)R^\circ$; $-N(R^\circ)S(O)_2NR^\circ_2$; $-N(R^\circ)S(O)_2R^\circ$; $-N(OR^\circ)R^\circ$; $-C(NH)NR^\circ_2$; $-P(O)_2R^\circ$; $-P(O)R^\circ_2$; $-OP(O)R^\circ_2$; $-OP(O)(OR^\circ)_2$; $SiR^\circ_3$; $-(C_{1-4}$ straight or branched)alkylene)O$-$N(R$^\circ)_2$; or $-(C_{1-4}$ straight or branched alkylene)C(O)O$-$N(R$^\circ)_2$, wherein each R$^\circ$ may be substituted as defined below and is independently hydrogen, $C_{1-6}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^{\bullet}$, -(haloR$^{\bullet}$), —(CH$_2$)$_{0-2}$OH, —(CH$_2$)$_{0-2}$OR$^{\bullet}$, —(CH$_2$)$_{0-2}$CH(OR$^{\bullet}$)$_2$; —O(haloR$^{\bullet}$), —CN, —N$_3$, —(CH$_2$)$_{0-2}$C(O)R$^{\bullet}$, —(CH$_2$)$_{0-2}$C(O)OH, —(CH$_2$)$_{0-2}$C(O)OR$^{\bullet}$, —(CH$_2$)$_{0-2}$SR$^{\bullet}$, —(CH$_2$)$_{0-2}$SH, —(CH$_2$)$_{0-2}$NH$_2$, —(CH$_2$)$_{0-2}$NHR$^{\bullet}$, —(CH$_2$)$_{0-2}$NR$^{\bullet}$$_2$, —NO$_2$, —SiR$^{\bullet}$$_3$, —OSiR$^{\bullet}$$_3$, —C(O)SR$^{\bullet}$, —(C$_{1-4}$ straight or branched alkylene)C(O)OR$^{\bullet}$, or —SSR$^{\bullet}$ wherein each R$^{\bullet}$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^{\bullet}$, -(haloR$^{\bullet}$), —OH, —OR$^{\bullet}$, —O(haloR$^{\bullet}$), —CN, —C(O)OH, —C(O)OR$^{\bullet}$, —NH$_2$, —NHR$^{\bullet}$, —NR$^{\bullet}$$_2$, or —NO$_2$, wherein each R$^{\bullet}$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^{\dagger}$, —NR$^{\dagger}$$_2$, —C(O)R$^{\dagger}$, —C(O)OR$^{\dagger}$, —C(O)C(O)R$^{\dagger}$, —C(O)CH$_2$C(O)R$^{\dagger}$, —S(O)$_2$R$^{\dagger}$, —S(O)$_2$NR$^{\dagger}$$_2$, —C(S)NR$^{\dagger}$$_2$, —C(NH)NR$^{\dagger}$$_2$, or —N(R$^{\dagger}$)S(O)$_2$R$^{\dagger}$; wherein each R$^{\dagger}$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^{\dagger}$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^{\dagger}$ are independently halogen, —R$^{\bullet}$, -(haloR$^{\bullet}$), —OH, —OR$^{\bullet}$, —O(haloR$^{\bullet}$), —CN, —C(O)OH, —C(O)OR$^{\bullet}$, —NH$_2$, —NHR$^{\bullet}$, —NR$^{\bullet}$$_2$, or —NO$_2$, wherein each R$^{\bullet}$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable protecting group —As used herein, the term "suitable protecting group," refers to amino protecting groups or hydroxyl protecting groups depending on its location within the compound and includes those described in detail in *Protecting Groups in Organic Synthesis*, T. W. Greene and P. G. M. Wuts, 3$^{rd}$ edition, John Wiley & Sons, 1999.

Suitable amino—protecting groups include methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Suitable hydroxylprotecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxide, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris(levulinoyloxyphenyl)methyl, 4,4',4''-tris(benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate.

In any case where a chemical variable (e.g., an R group) is shown attached to a bond that crosses a bond of ring, this means that one or more such variables are optionally attached to the ring having the crossed bond. Each R group on such a ring can be attached at any suitable position, this is generally understood to mean that the group is attached in place of a hydrogen atom on the parent ring. This includes the possibility that two R groups can be attached to the same ring atom. Furthermore, when more than one R group is present on a ring, each may be the same or different than other R groups attached thereto, and each group is defined independently of other groups that may be attached elsewhere on the same molecule, even though they may be represented by the same identifier.

Information on proteins of the present invention:

PRPK: CAS registry number 183450-12-6. Pubmed names (accession number, version number): TP53-regulating kinase [Homo sapiens] (NP_291028.3 GI:41327715); RecName: Full=TP53-regulating kinase; AltName: Full=p53-related protein kinase; AltName: Full=Nori-2 (Q96S44.2 GI:26398348); TP53RK protein [Homo sapiens] (AAH10637.1 GI:14714958); TP53RK protein [Homo sapiens] (AAH10637.1 GI:14714958); TP53 regulating kinase [Homo sapiens] (AAH09727.1 GI:16307277); TP53 regulating kinase [Homo sapiens] (AAH66309.1 GI:42542637).

TPRKB: CAS registry number 562887-50-7. Pubmed names (accession numbers, version number): p53-related protein klinase-binding protein, CGI-121 protein-human (JC7956 GI:60729596); TP53RK-binding protein [Homo sapiens] (NP_057142.1 GI:7705590); CGI-121 S1 isoform [Homo sapiens] (AAN76357.1 GI:26224772); CGI-121 L1 isoform [Homo sapiens] (AAN76356.1 GI:26224770); RecName: Full=TP53RK-binding protein; AltName: Full=PRPK-binding protein (Q9Y3C4.1 GI:74735252).

OSGEP: CAS registry number 129430-53-1. Pubmed names (accession numbers, version number): OSGEP [Homo sapiens] (CAG33513.1 GI:48146581); RecName: Full=Probable O-sialoglycoprotein endopeptidase; Short=hOSGEP (Q9NPF4.1 GI:47605574); probable O-sialoglycoprotein endopeptidase [Homo sapiens] (NP_060277.1 GI:8923380); O-sialoglycoprotein endopeptidase [Homo sapiens] (BAB33172.1 GI:13358864); O-sialoglycoprotein endopeptidase [Homo sapiens] (BAB33147.1 GI:13358802); O-sialoglycoprotein endopeptidase [Homo sapiens] (AAH32310.1 GI:21619574).

LAGE3: Pubmed names (accession numbers, version number): L antigen family, member 3 [Homo sapiens] (CAI43195.1 GI:57284198); L antigen family member 3 [Homo sapiens] (NP_006005.2 GI:24430137); RecName: Full=L antigen family member 3; AltName: Full=Protein ITBA2; AltName: Full=Protein ESO-3 (Q14657.2 GI:54041570); L antigen family, member 3 [Homo sapiens] (AAH15744.2 GI:37589922); L antigen family, member 3 [Homo sapiens] (AAH62330.1 GI:38383094); L antigen family, member 3 [Homo sapiens] (CAQ08986.1 GI:168984692). LAGE3 homologs: CTAG2 protein [Homo sapiens] (AAI14934.1 GI:133777817, AAI28046.1 GI:118341658); cancer/testis antigen 2 isoform LAGE-1b [Homo sapiens] (NP_066274.1 GI:10337609); cancer/testis antigen 2, isoform CRA_b [Homo sapiens] (EAW72669.1 GI:119593075); cancer/testis antigen 2, isoform CRA_a [Homo sapiens] (EAW72668.1 GI:119593074); cancer/testis antigen 2 isoform LAGE-1a [Homo sapiens] (NP_758965.1 GI:50233789); RecName: Full=Cancer/testis antigen 2; Short=CT2; AltName: Full=L antigen family member 1; Short=LAGE-1; AltName: Full=Autoimmunogenic cancer/testis antigen NY-ESO-2; AltName: Full=Cancer/testis antigen 6.2; Short=CT6.2 (075638.2 GI:296434470); LAGE-1a protein transcript variant 1 [Homo sapiens] (AAV98585.1 GI:56567192); LAGE-1a protein transcript variant 2 [Homo sapiens] (AAV98584.1 GI:56567190); Cancer/testis antigen 2 [Homo sapiens] (AAH02833.1 GI:12803969).

DETAILED DESCRIPTION OF CERTAIN EMBODIMENTS

In some embodiments, the present invention provides methods of identifying agents that interact with a PRPK/TPRKB complex. In some embodiments, the present invention provides methods of identifying agents that interact with a KEOPS complex comprising PRPK, TPRKB, OSGEP, and LAGE3 and its homologs. In some embodiments, such methods include high throughput screening methods. In some embodiments, the methods include in vitro, in cyto and/or in vivo assays. In certain embodiments, the present invention encompasses agents identified by inventive methods.

In some embodiments, the present invention provides methods of identifying agents that modulate PRPK.

In some embodiments, the present invention provides methods of inhibiting proliferation (e.g., B cell proliferation). In some embodiments, the present invention provides methods of inducing IL-2 production. In some embodiments, the present invention provides methods of inhibiting TNF-α production. In some embodiments, the present invention provides methods of inducing natural killer cell activation. In some embodiments, the present invention provides methods of enhancing immune synapse formation.

In some embodiments, the present invention provides a method of treating inflammation, an inflammatory disease or an autoimmune disease. In some embodiments, the present invention provides a method of treating an oncogenic or cancerous condition.

PRPK-TPRKB and KEOPS Complex

The inventors have surprisingly found that PRPK and TPRKB mediate the immunomodulatory and growth inhibitory activities of compounds such as lenalidomide and pomalidomide. PRPK and TPRKB were captured by affinity reagents based on lenalidomide, pomalidomide, and thalidomide.

PRPK and TPRKB are evolutionarily conserved from archaea and yeast to humans; yet very little is known about the function of these proteins, particularly in humans. There are a limited number of publications describing these human proteins and below is a summary of the key literature findings.

In yeast and archaea, Bud32 and Cgi121 (PRPK and TPRKB, respectively) have previously been demonstrated to form a functional complex named KEOPS with two other proteins called Kae1 and Pcc1. The yeast KEOPS complex is required for telomere maintenance and transcriptional regulation (Downey et al, Cell 124:1155-1168 (2006); Kisseleva- Romanova et al, EMBO J. 25:3576-3585 (2006)). The structure of the KEOPS complex has been studied by crystallography, although the proteins were of mixed origin (mostly archaea) (Mao et al, Mol Cell 32:259-275 (2008); Hecker et al, EMBO J. 27:2340-2351 (2008)). Structure-based sequence alignments indicate that Bud32 (PRPK) is an atypical kinase that possesses an architecture characteristic of protein kinases but lacks an activation loop that is normally responsible for substrate recognition. Formation and biological function of the human KEOPS complex has not been previously disclosed.

The inventors have further determined that the human orthologues of the two other proteins in the KEOPS complex, OSGEP and LAGE3 and its homologs (Kae1 and Pcc1, respectively), are also captured by a pomalidomide-based affinity reagent. This is the first evidence that a KEOPS complex may form in humans. In the literature, there are very few reports describing potential functions of PRPK and TPRKB. PRPK was first identified as a transcript that is up-regulated in IL-2 activated cytolytic T cells (Abe et al, J. Biol. Chem. 276:44003-44011 (2001)). It has been suggested that PRPK might possess kinase activity and phosphorylate p53 at Ser15 in vitro (Facchin et al (2003) FEBS Letters 549: 63). Kinase activity of recombinant PRPK was not observed unless PRPK was pre-incubated with cell lysates, suggesting that PRPK may be regulated by other cellular component(s). The physical interaction between PRPK and TPRKB has been demonstrated in vitro (Miyoshi et al, (2003) Biochem. Biophys. Res. Commun 303:399-405) and there is evidence that PRPK may be activated by Akt (Facchin et al, Cell Mol Life Sci 64:2680-2689 (2007)), suggesting that it could be part of an important regulatory pathway relevant to cancer. The human homologs of LAGE3 such as CTAG2 and CTG1B are known as cancer/testis antigens which express specifically in cancer and testis and are a target for cancer immunotherapy (Caballero et al, Cancer Sci (2009) 100, 2014) and may also form a KEOPS complex.

PRPK-TPRKB and KEOPS Complex Modulators

In some embodiments, the invention provides methods of identifying an agent that modulates PRPK, TPRKB, OSGEP, LAGE3 and its homologs, or a complex or combination thereof. Inventive methods comprise providing a system comprising a protein of interest (e.g., PRPK, TPRKB, OSGEP, LAGE3 and its homologs, or a complex or combination thereof); providing a test agent; contacting the test agent with the system; and detecting an interaction between the test agent and the protein of interest (e.g., PRPK, TPRKB, OSGEP, LAGE3 and its homologs, or a complex or combination thereof).

Test Agents

In general, any agent can be screened in a method according to the invention. In some embodiments, a plurality of test agents is screened according to the invention. Exemplary test agents include, but are not limited to, chemical compounds, small molecules, proteins or peptides, antibodies, co-crystals, nano-crystals, nucleic acids (e.g., DNAs, RNAs, DNA/RNA hybrids, siRNAs, shRNAs, miRNAs, ribozymes, aptamers, etc.), carbohydrates (e.g., mono-, di-, or poly-saccharides), lipids (e.g., phospholipids, triglycerides, steroids, etc.), amino acids, natural products, or any combination thereof. Test agents can also be designed using computer-based rational drug design methods. Typically, a plurality of test agents (e.g., libraries of test agents) are tested in screening assays for potential modulators. For example, test agents may be provided as chemically synthesized libraries. In some embodiments, test agents are provided as combinatorial libraries, phase display libraries, nucleic acid libraries, amino acid libraries, peptide libraries, or combinations thereof. In certain embodiments, a library is designed in silico and synthesized for screening.

In some embodiments, small molecule test agents are screened using methods according to the present invention. In some embodiments, compound libraries synthesized de novo can be screened to identify novel compounds that have target modulatory functions. In some embodiments, public libraries containing drugs (including FDA approved drugs) can be screened to identify existing compounds whose target modulating activities are previously unknown. In some embodiments, modified libraries containing derivatives or analogues of existing compounds can be synthesized using methods well known in the art and screened to identify novel or improved target modulators. Suitable small molecule compound libraries can be obtained from commercial vendors such as ChemBridge Libraries (chembridge.com), BIOMOL International, ASINEX, ChemDiv, ChemDB, ICCB-Longwood. In some embodiments, suitable small molecule libraries contain a large collection (e.g., >100,000 compounds) of commercial compounds selected for diversity and good "drug-like" properties. In some embodiments, small molecules are screened individually.

In some embodiments, antibodies can be screened according to the present invention. For example, antibodies can be designed to target PRPK, TPRKB, OSGEP, and/or LAGE3 and its homologs.

Antibodies can be generated using methods well known in the art. For example, protocols for antibody production are described by Harlow and Lane, *Antibodies: A Laboratory Manual*, (1988). Typically, antibodies can be generated in mouse, rat, guinea pig, hamster, camel, llama, shark, or other appropriate host. Alternatively, antibodies may be made in chickens, producing IgY molecules (Schade et al., (1996) *ALTEX* 13(5):80-85). In some embodiments, antibodies suitable for the present invention are subhuman primate antibodies. For example, general techniques for raising therapeutically useful antibodies in baboons may be found, for example, in Goldenberg et al., international patent publication No. WO 91/11465 (1991), and in Losman et al., *Int. J. Cancer* 46: 310 (1990). In some embodiments, monoclonal antibodies may be prepared using hybridoma methods (Milstein and Cuello, (1983) *Nature* 305(5934):537-40.). In some embodiments, monoclonal antibodies may also be made by recombinant methods (U.S. Pat. No. 4,166,452, 1979).

In some embodiments, antibodies suitable for the invention may include humanized or human antibodies. Humanized forms of non-human antibodies are chimeric Igs, Ig chains or fragments (such as Fv, Fab, Fab', F(ab')2 or other antigen-binding subsequences of Abs) that contain minimal sequence derived from non-human Ig. Generally, a humanized antibody has one or more amino acid residues introduced from a non-human source. These non-human amino acid residues are often referred to as "import" residues, which are typically taken from an "import" variable domain. Humanization is accomplished by substituting rodent CDRs or CDR sequences for the corresponding sequences of a human antibody (Riechmann et al., *Nature* 332(6162):323-7, 1988; Verhoeyen et al., *Science*. 239(4847):1534-6, 1988.). Such "humanized" antibodies are chimeric Abs (U.S. Pat. No. 4,816,567, 1989), wherein substantially less than an intact human variable domain has been substituted by the corresponding sequence from a non-human species. In some embodiments, humanized antibodies are typically human antibodies in which some CDR residues and possibly some FR residues are substituted by residues from analogous sites in rodent Abs. Humanized antibodies include human Igs (recipient antibody) in which residues from a complementary determining region (CDR) of the recipient are replaced by residues from a CDR of a non-human species (donor antibody) such as mouse, rat or rabbit, having the desired specificity, affinity and capacity. In some instances, corresponding non-human residues replace Fv framework residues of the human Ig. Humanized antibodies may comprise residues that are found neither in the recipient antibody nor in the imported CDR or framework sequences. In general, the humanized antibody comprises substantially all of at least one, and typically two, variable domains, in which most if not all of the CDR regions correspond to those of a non-human Ig and most if not all of the FR regions are those of a human Ig consensus sequence. The humanized antibody optimally also comprises at least a portion of an Ig constant region (Fc), typically that of a human Ig (Riechmann et al., *Nature* 332(6162):323-7, 1988; Verhoeyen et al., *Science.* 239(4847):1534-6, 1988.).

Human antibodies can also be produced using various techniques, including phage display libraries (Hoogenboom et al., *Mol Immunol.* (1991) 28(9):1027-37; Marks et al., *J Mol Biol.* (1991) 222(3):581-97) and the preparation of human monoclonal antibodies (Reisfeld and Sell, 1985, *Cancer Surv.* 4(1): 271-90). Similarly, introducing human Ig genes into transgenic animals in which the endogenous Ig genes have been partially or completely inactivated can be exploited to synthesize human antibodies. Upon challenge, human antibody production is observed, which closely resembles that seen in humans in all respects, including gene rearrangement, assembly, and antibody repertoire (Fishwild et al., High-avidity human IgG kappa monoclonal antibodies from a novel strain of minilocus transgenic mice, *Nat Biotechnol.* 1996 July; 14(7):845-51; Lonberg et al., Antigen-specific human antibodies from mice comprising four distinct genetic modifications, *Nature* 1994 Apr. 28; 368(6474):856-9; Lonberg and Huszar, Human antibodies from transgenic mice, *Int. Rev. Immunol.* 1995; 13(1):65-93; Marks et al., By-passing immunization: building high affinity human antibodies by chain shuffling. *Biotechnology* (N Y). 1992 July; 10(7):779-83).

In some embodiments, peptide and/or protein test agents can be screened according to the present invention. As used herein, the terms "protein" and "peptide" can be used interchangeably. In certain embodiments, peptides range from about 5 to 40, 10 to 35, to 30, or 20 to 25 amino acids in size. A suitable peptide library can be a random peptide library produced by recombinant bacteriophage, for example, Scott and Smith, Science, 249:386-390 (1990); Cwirla et al., Proc. Natl. Acad. Sci., 87:6378-6382 (1990); Devlin et al., Science, 249:404-406 (1990), or a chemical library. Using the "phage method" very large libraries can be constructed ($10^6$-$10^8$ chemical entities). A second approach uses primarily chemical methods, of which the Geysen method (Geysen et al., *Molecular Immunology* 23:709-715 (1986); Geysen et al. J. Immunologic Method 102:259-274 (1987)) and the method of Fodor et al. (*Science* 251:767-773 (1991)) are examples. Furka et al. *14th International Congress of Biochemistry*, Volume 5, Abstract FR:013 (1988); Furka, *Int. J. Peptide Protein Res.* 37:487-493 (1991), describe methods to produce a mixture of peptides.

PRPK is known to phosphorylate p53. Thus, peptide modulators of PRPK may comprise amino acids found in p53. In some embodiments, test agents may comprise TPRKB, OSGEP or LAGE3 homologs proteins and/or characteristic portions thereof.

In some embodiments, test agents are peptide mimetics. As used herein, the term "peptide mimetics" refers to structures which substitute for peptides in interactions with natural binding partners, receptors, and/or enzymes. The mimetic may possess affinity, efficacy, and/or substrate function. In certain embodiments, a peptide mimetic exhibits function(s) of a particular peptide, without restriction of structure. Peptide mimetics may include amino acid residues and/or other chemical moieties which provide the desired functional characteristics.

In some embodiments, synthetic libraries (Needels et al., *Proc. Natl. Acad. Sci. USA* 90:10700-4 (1993; Ohlmeyer et al., *Proc. Natl. Acad. Sci. USA* 90:10922-10926 (1993); Lam et al., International Patent Publication No. WO 92/00252; Kocis et al., International Patent Publication No. WO 94/28028, each of which is incorporated herein by reference in its entirety), and the like can be used to screen for modulators of a target of interest according to the present invention. Once a potential modulator is identified, chemical analogues can be either selected from a library of chemicals as are commercially available from commercial vendors such as ChemBridge Libraries (chembridge.com), BIOMOL International, ASINEX, ChemDiv, ChemDB, ICCB-Longwood or alternatively synthesized de novo.

In some embodiments, antisense molecules are screened according to the present invention. Antisense molecules are RNA or single-stranded DNA molecules with nucleotide sequences complementary to a specified mRNA. When a laboratory-prepared antisense molecule is injected into cells containing the normal mRNA transcribed by a gene under study, the antisense molecule can base-pair with the mRNA, preventing translation of the mRNA into protein. The resulting double-stranded RNA or RNA/DNA is digested by enzymes that specifically attach to such molecules. Therefore, a depletion of the mRNA occurs, blocking the translation of the gene product so that antisense molecules find uses in medicine to block the production of deleterious proteins. Methods of producing and utilizing antisense RNA are well known to those of ordinary skill in the art (see, for example, C. Lichtenstein and W. Nellen (Editors), *Antisense Technology: A Practical Approach*, Oxford University Press (December, 1997); S. Agrawal and S. T. Crooke, *Antisense Research and Application* (Handbook of Experimental Pharmacology, Volume 131), Springer Verlag (April, 1998); I. Gibson, *Antisense and Ribozyme Methodology: Laboratory Companion*, Chapman & Hall (June, 1997); J. N. M. Mol and A. R. Van Der Krol, *Antisense Nucleic Acids and Proteins*, Marcel Dekker; B. Weiss, *Antisense Oligonodeoxynucleotides and Antisense RNA Novel Pharmacological and Therapeutic Agents*, CRC Press (June, 1997); Stanley et al., *Antisense Research and Applications*, CRC Press (June, 1993); C. A. Stein and A. M. Krieg, *Applied Antisense Oligonucleotide Technology* (April, 1998)).

The antisense molecules and ribozymes may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding UGGT. Such DNA sequences maybe incorporated into a wide variety of vectors with suitable RNA polymerase promoters such as T7 or SP6. Alternatively, these cDNA constructs that synthesize antisense RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2'O-methyl rather than phosphodiesterase linkages within the backbone of the molecule. This concept can be extended by the inclusion of nontraditional bases such as inosine, queosine, and wybutosine, as well as acetyl-, methyl-, thio-, similarly modified forms of adenine, cytidine, guanine, thymine, and uridine which are not as easily recognized by endogenous endonucleases.

RNA interference (RNAi) is a mechanism of post-transcriptional gene silencing mediated by double-stranded RNA (dsRNA), which is distinct from the antisense and ribozyme-based approaches described above. dsRNA molecules are believed to direct sequence-specific degradation of mRNA in cells of various lineages after first undergoing processing by an RNase III-like enzyme called DICER (Bernstein et al., Nature 409:363, 2001) into smaller dsRNA molecules comprised of two 21 nt strands, each of which has a 5' phosphate group and a 3' hydroxyl, and includes a 19 nt region precisely complementary with the other strand, so that there is a 19 nt duplex region flanked by 2 nt-3' overhangs. RNAi is thus mediated by short interfering RNAs (siRNA), which typically comprise a double-stranded region approximately 19 nucleotides in length typically with 1-2 nucleotide 3' overhangs on each strand, resulting in a total length typically of between approximately 21 and 23 nucleotides.

It will also be appreciated that siRNAs can have a range of lengths, e.g., the double-stranded portion can range from 15-29 nucleotides. It will also be appreciated that the siRNA can have a blunt end or a 3' overhang at either or both ends. If present, such 3' overhang is often from 1-5 nucleotides in length.

siRNA has been shown to downregulate gene expression when transferred into mammalian cells by such methods as transfection, electroporation, or microinjection, or when expressed in cells via any of a variety of plasmid-based approaches. RNA interference using siRNA is reviewed in, e.g., Tuschl, T., Nat. Biotechnol., 20:446-448, May 2002. See also Yu, J., et al., Proc. Natl. Acad. Sci., 99(9), 6047-6052 (2002); Sui, G., et al., Proc. Natl. Acad. Sci., 99(8), 5515-5520 (2002); Paddison, P., et al., Genes and Dev., 16, 948-958 (2002); Brummelkamp, T. et al., Science, 296, 550-553 (2002); Miyagashi, M. and Taira, K., Nat. Biotech., 20, 497-500 (2002); Paul, C., et al., Nat. Biotech., 20, 505-508 (2002).

Indeed, in vivo inhibition of specific gene expression by RNAi has been achieved in various organisms including mammals. For example, Song et al., Nature Medicine, 9:347-351 (2003) discloses that intravenous injection of Fas siRNA compounds into laboratory mice with autoimmune hepatitis specifically reduced Fas mRNA levels and expression of Fas protein in mouse liver cells. Several other approaches for delivery of siRNA into animals have also proved to be successful. See e.g., McCaffery et al., Nature, 418:38-39 (2002); Lewis et al., Nature Genetics, 32:107-108 (2002); and Xia et al., Nature Biotech., 20:1006-1010 (2002).

siRNA may consist of two individual nucleic acid strands or of a single strand with a self-complementary region capable of forming a hairpin (stem-loop) structure. A number of variations in structure, length, number of mismatches, size of loop, identity of nucleotides in overhangs, etc., are consistent with effective siRNA-triggered gene silencing. While not wishing to be bound by any theory, it is thought that intracellular processing (e.g., by DICER) of a variety of different precursors results in production of siRNA capable of effectively mediating gene silencing. Generally it is desirable to target exons rather than introns, and it may also be particularly desirable to select sequences complementary to regions within the 3' portion of the target transcript. Generally it is preferred to select sequences that contain approximately equimolar ratio of the different nucleotides and to avoid stretches in which a single residue is repeated multiple times.

siRNA may thus comprise RNA molecules typically having a double-stranded region approximately 19 nucleotides in length typically with 1-2 nucleotide 3' overhangs on each strand, resulting in a total length of between approximately 21 and 23 nucleotides. As used herein, siRNA also includes various RNA structures that may be processed in vivo to generate such molecules. Such structures include RNA strands containing two complementary elements that hybridize to one another to form a stem, a loop, and optionally an overhang, preferably a 3' overhang. Typically, the stem is approximately 19 bp long, the loop is about 1-20, preferably about 4-10, and more preferably about 6-8 nucleotides long and/or the overhang is typically about 1-20, and preferably about 2-15 nucleotides long. In certain embodiments of the invention the stem is minimally 19 nucleotides in length and may be up to approximately 29 nucleotides in length. Loops of 4 nucleotides or greater are less likely subject to steric constraints than are shorter loops and therefore may be preferred. The overhang may include a 5' phosphate and a 3' hydroxyl. The overhang may, but need not, comprise a plurality of U residues, e.g., between 1 and 5 U residues.

In some embodiments, siRNA compounds suitable for the present invention can be designed based on sequence information of proteins and genes involved in the target pathway. For example, siRNAs can be designed to target the biological target of interest, biological target activators, inhibitors or substrates.

Suitable siRNAs can be synthesized using conventional RNA synthesis methods. For example, they can be chemically synthesized using appropriately protected ribonucleoside phosphoramidites and a conventional DNA/RNA synthesizer. Various applicable methods for RNA synthesis are disclosed in, e.g., Usman et al., J. Am. Chem. Soc., 109:7845-7854 (1987) and Scaringe et al., Nucleic Acids Res., 18:5433-5441 (1990). Custom siRNA synthesis services are available from commercial vendors such as Ambion (Austin, Tex., USA), Dharmacon Research (Lafayette, Colo., USA), Pierce Chemical (Rockford, Ill., USA), ChemGenes (Ashland, Mass., USA), Proligo (Hamburg, Germany), and Cruachem (Glasgow, UK).

Inventive siRNAs may be comprised entirely of natural RNA nucleotides, or may instead include one or more nucleotide analogs and/or modifications as mentioned above for antisense molecules. The siRNA structure may be stabilized, for example by including nucleotide analogs at one or more free strand ends in order to reduce digestion, e.g., by exonucleases. Alternatively, siRNA molecules may be generated by in vitro transcription of DNA sequences encoding the relevant molecule. Such DNA sequences may be incorporated into a wide variety of vectors with suitable RNA polymerase promoters such as T7, T3, or SP6.

In some embodiments, natural product libraries can be screened according to the present invention. In some embodiments, libraries are designed in silico (e.g., based on structural analysis of the protein or complex of interest) and synthesized for screening according to the invention.

In some embodiments, rational drug design may be used to predict and/or produce structural analogs of known biologically-active candidate substances. By creating such analogs, it is possible to fashion drugs which may be more active and/or stable than the natural substances, may have different susceptibility to alteration, and/or may affect the function of various other molecules. In one approach, one would generate a three-dimensional structure for a known candidate substance and/or characteristic portion thereof. In some embodiments, generation of a three-dimensional structure is accomplished by x-ray crystallography, NMR structure, computer modeling, and/or by a combination of these approaches.

In some embodiments, a test agent is a compound of formula I:

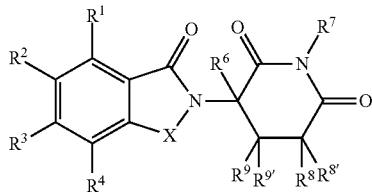

I wherein:
X is —C(=O)— or —CH$_2$—;
R$^1$, R$^2$, R$^3$, and R$^4$ are independently hydrogen, halo, C$_{1-6}$ alkyl, C$_{1-6}$ alkoxy, or —N(R$^5$)$_2$;
each R$^5$ is independently hydrogen or C$_{1-6}$ alkyl, or two R$^5$ groups are taken together with the nitrogen to which they are attached to form a heterocycle;
R$^6$ is hydrogen, halo, benzyl, or C$_{1-8}$ alkyl;
R$^7$ is hydrogen, benzyl, or C$_{1-8}$ alkyl; and
R$^8$, R$^{8'}$, R$^9$, and R$^{9'}$ are independently hydrogen, halo, C$_{1-6}$ alkyl, or C$_{1-6}$ alkoxy.

In some embodiments, a test agent is a compound of formula II:

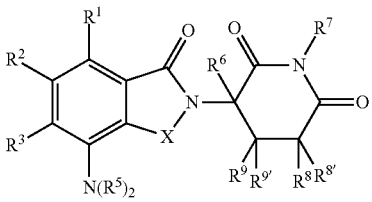

II wherein:
X is —C(=O)— or —CH$_2$—;
R$^1$, R$^2$, and R$^3$ are independently hydrogen, halo, C$_{1-6}$ alkyl, or C$_{1-6}$ alkoxy;
each R$^5$ is independently hydrogen or C$_{1-6}$ alkyl, or two R$^5$ groups are taken together with the nitrogen to which they are attached to form a heterocycle;
R$^6$ is hydrogen, halo, benzyl, or C$_{1-8}$ alkyl;
R$^7$ is hydrogen, benzyl, or C$_{1-8}$ alkyl; and
R$^8$, R$^{8'}$, R$^9$, and R$^{9'}$ are independently hydrogen, halo, C$_{1-6}$ alkyl, or C$_{1-6}$ alkoxy.

In some embodiments, the invention provides a compound of formula III:

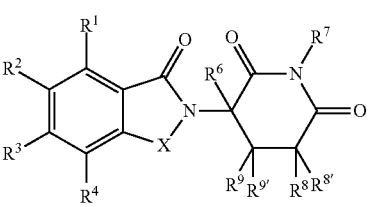

III wherein:
X is —C(=O)— or —CH$_2$—;
R$^1$, R$^2$, R$^3$, and R$^4$ are independently hydrogen, halo, C$_{1-6}$ alkyl, C$_{1-6}$ alkoxy, or —N(R$^5$)$_2$;
each R$^5$ is independently hydrogen or C$_{1-6}$ alkyl, or two R$^5$ groups are taken together with the nitrogen to which they are attached to form a heterocycle;
R$^6$ is hydrogen, halo, benzyl, or C$_{1-8}$ alkyl;
R$^7$ is hydrogen, benzyl, or C$_{1-8}$ alkyl; and
R$^8$, R$^{8'}$, R$^9$, and R$^{9'}$ are independently hydrogen, halo, C$_{1-6}$ alkyl, or C$_{1-6}$ alkoxy;
wherein at least one of R$^7$, R$^8$, R$^{8'}$, R$^9$, and R$^{9'}$ is not hydrogen.

In some embodiments, a test agent is a compound of formula III.

In some embodiments, the invention provides a compound of formula IIIa or IIIb:

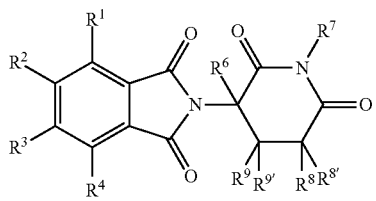

IIIa

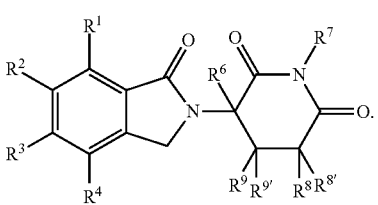

IIIb

In some embodiments, the invention provides a compound of formula IV:

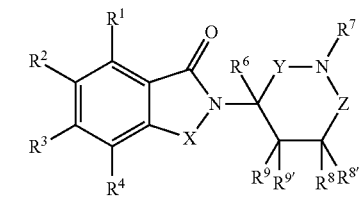

IV wherein:
X is —C(=O)— or —CH$_2$—;
Y is —C(=O)— or —C(R$^{10}$)(R$^{10'}$)—;
Z is —C(=O)— or —C(R$^{11}$)(R$^{11'}$)—;
R$^1$, R$^2$, R$^3$, and R$^4$ are independently hydrogen, halo, C$_{1-6}$ alkyl, C$_{1-6}$ alkoxy, or —N(R$^5$)$_2$;
each R$^5$ is independently hydrogen or C$_{1-6}$ alkyl, or two R$^5$ groups are taken together with the nitrogen to which they are attached to form a heterocycle;
R$^6$ is hydrogen, halo, benzyl, or C$_{1-8}$alkyl;
R$^7$ is hydrogen, benzyl, or C$_{1-8}$alkyl; and
R$^8$, R$^{8'}$, R$^9$, R$^{9'}$, R$^{10}$, R$^{10'}$, R$^{11}$, and R$^{11'}$ are independently hydrogen, halo, C$_{1-6}$ alkyl, or C$_{1-6}$ alkoxy.

In some embodiments, the invention provides a compound of formula:
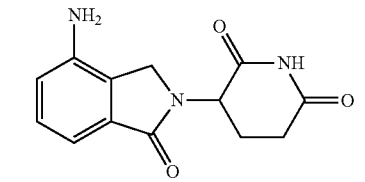
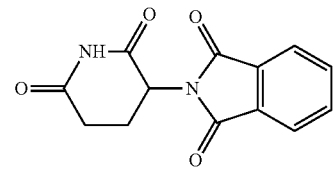
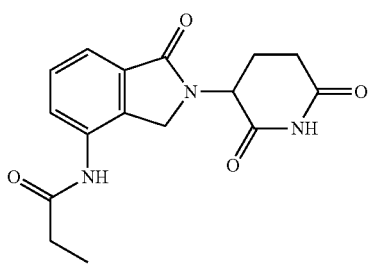
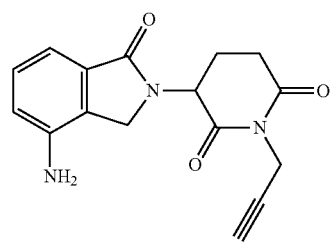
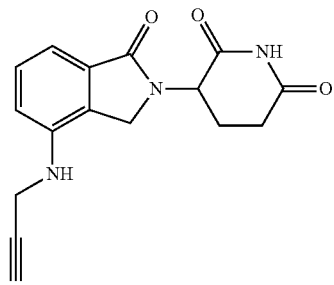
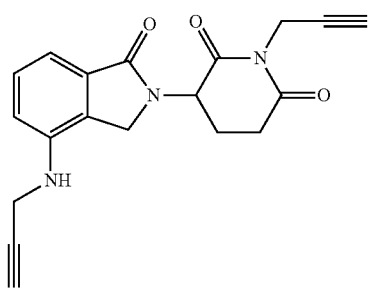
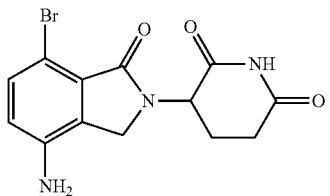
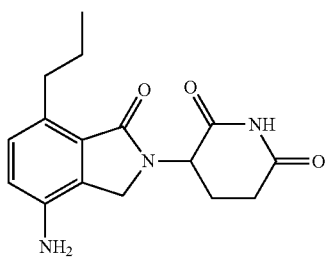
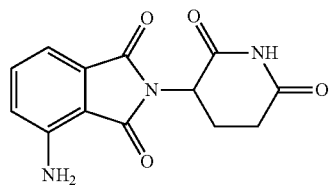
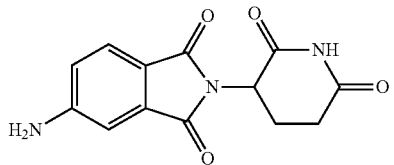
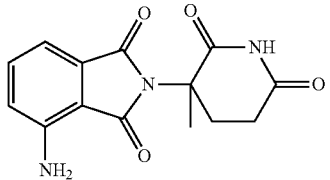
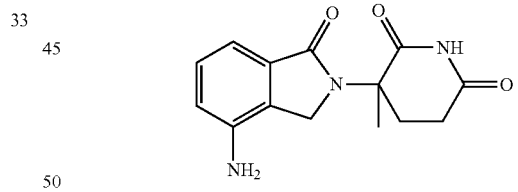
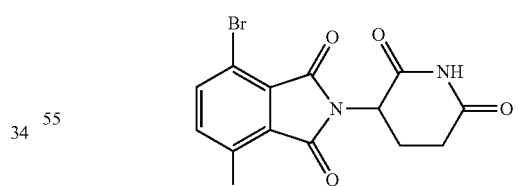
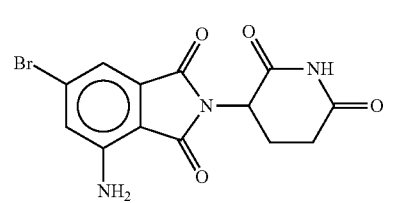

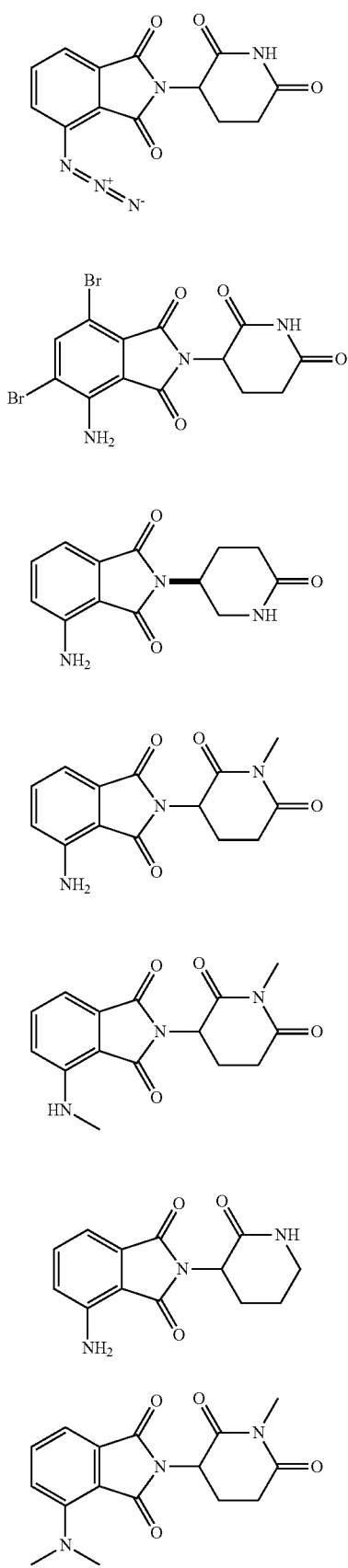
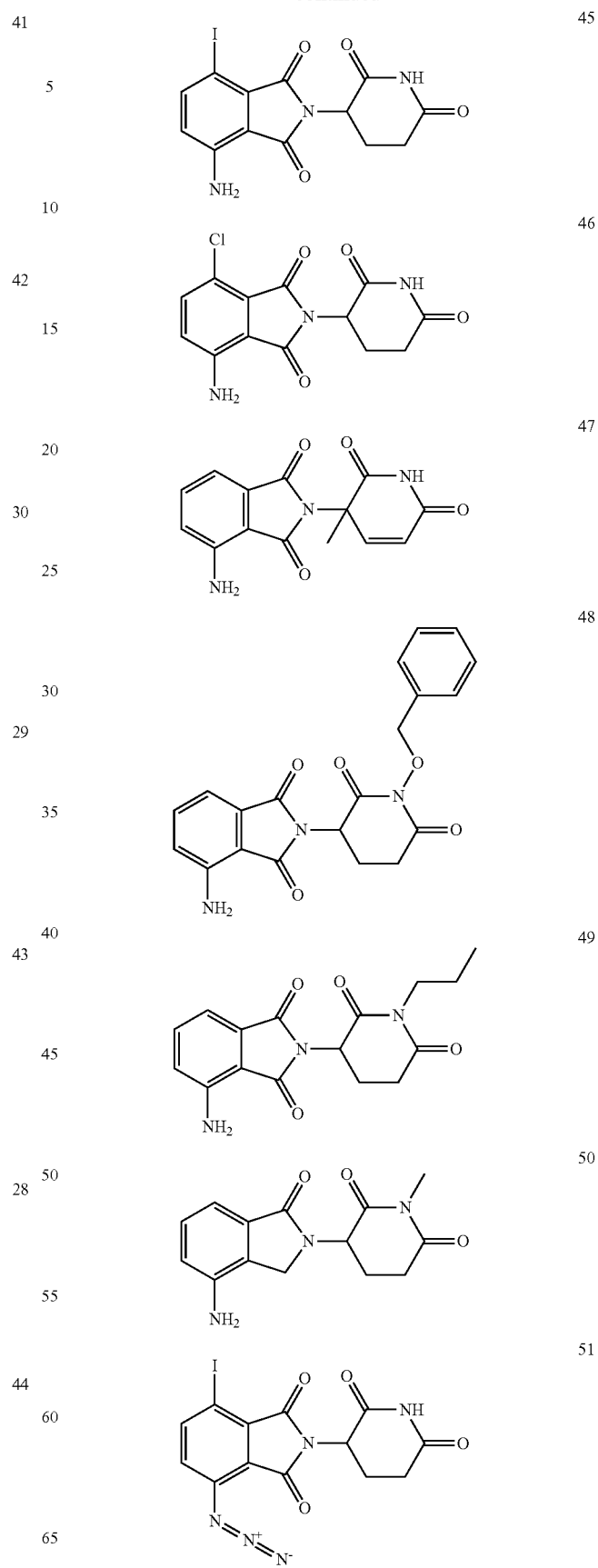

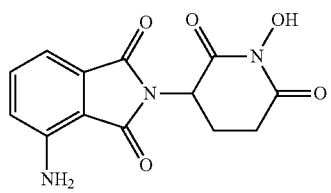

52

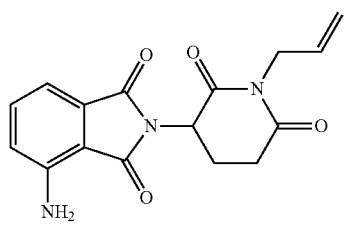

53

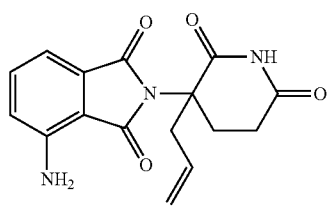

54

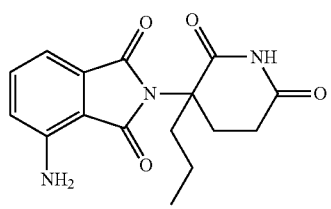

55

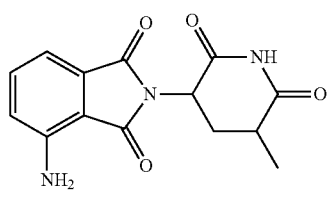

56

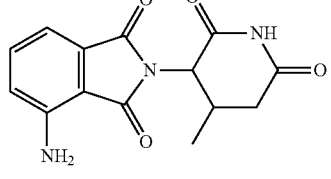

57

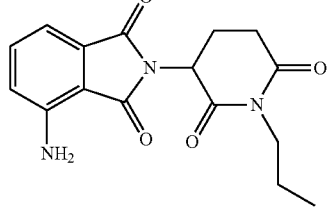

58

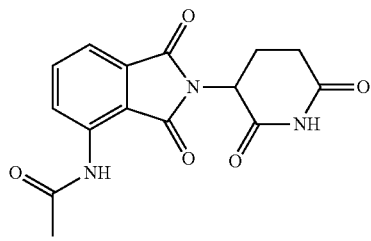

59

In certain embodiments, a test agent and/or modulator according to the present invention is found in one or more of the following patents: U.S. Pat. No. 5,635,517, U.S. Pat. No. 6,045,501, U.S. Pat. No. 6,281,230, U.S. Pat. No. 6,315,720, U.S. Pat. No. 6,555,554, U.S. Pat. No. 6,561,976, U.S. Pat. No. 6,561,977, U.S. Pat. No. 6,755,784, U.S. Pat. No. 6,908,432, U.S. Pat. No. 7,119,106, U.S. Pat. No. 7,189,740, U.S. Pat. No. 7,465,800. In certain embodiments, a test agent and/or modulator according to the present invention is not found in one or more of the following patents: U.S. Pat. No. 5,635,517, U.S. Pat. No. 6,045,501, U.S. Pat. No. 6,281,230, U.S. Pat. No. 6,315,720, U.S. Pat. No. 6,555,554, U.S. Pat. No. 6,561,976, U.S. Pat. No. 6,561,977, U.S. Pat. No. 6,755,784, U.S. Pat. No. 6,908,432, U.S. Pat. No. 7,119,106, U.S. Pat. No. 7,189,740, U.S. Pat. No. 7,465,800. In certain embodiments, a test agent and/or modulator according to the present invention is 1-oxo-2-(2,6-dioxopiperidin-3-yl)-5-aminoisoindoline, 1-oxo-2-(2,6-dioxopiperidin-3-yl)-4-aminoisoindoline, 1-oxo-2-(2,6-dioxopiperidin-3-yl)-6-aminoisoindoline, 1-oxo-2-(2,6-dioxopiperidin-3-yl)-7-aminoisoindoline, 1,3-dioxo-2-(2,6-dioxopiperidin-3-yl)-4-aminoisoindoline, or 1,3-dioxo-2-(2,6-dioxopiperidin-3-yl)-5-aminoisoindoline. In certain embodiments, a test agent and/or modulator according to the present invention is not 1-oxo-2-(2,6-dioxopiperidin-3-yl)-5-aminoisoindoline, 1-oxo-2-(2,6-dioxopiperidin-3-yl)-4-aminoisoindoline, 1-oxo-2-(2,6-dioxopiperidin-3-yl)-6-aminoisoindoline, 1-oxo-2-(2,6-dioxopiperidin-3-yl)-7-aminoisoindoline, 1,3-dioxo-2-(2,6-dioxopiperidin-3-yl)-4-aminoisoindoline, or 1,3-dioxo-2-(2,6-dioxopiperidin-3-yl)-5-aminoisoindoline. In certain embodiments, a test agent and/or modulator according to the present invention is compound 29, 31, 27, or 23. In certain embodiments, a test agent and/or modulator according to the present invention is not compound 29, 31, 27, or 23. In certain embodiments, a test agent and/or modulator according to the present invention is compound 18. In certain embodiments, a test agent and/or modulator according to the present invention is not compound 18. In certain embodiments, a test agent and/or modulator according to the present invention is one or more of compounds 2-21. In certain embodiments, a test agent and/or modulator according to the present invention is not one or more of compounds 2-21. In certain embodiments, a test agent and/or modulator according to the present invention is one or more of compounds 24-26. In certain embodiments, a test agent and/or modulator according to the present invention is not one or more of compounds 24-26.

Identification and/or Characterization of PRPK-TPRKB and KEOPS Complex Modulators The present invention provides methods of identifying agents that modulate PRPK, TPRKB, OSGEP, LAGE3 and its homologs, PRPK-TPRKB complex and/or KEOPS complex. In some embodiments, an inventive method screens for modulators of PRPK, TPRKB, OSGEP, LAGE3 and its homologs, PRPK-TPRKB complex and/or KEOPS complex by identifying agents that bind to PRPK, TPRKB, OSGEP, LAGE3 and its homologs, PRPK-TPRKB complex and/or KEOPS complex. In some embodiments, an inventive method screens for modulators of PRPK, TPRKB, OSGEP, LAGE3 and its homologs, PRPK-TPRKB complex and/or KEOPS complex by identifying agents that bind to PRPK, TPRKB, OSGEP, LAGE3 and its homologs, PRPK-TPRKB complex and/or KEOPS complex with an affinity within the range of less than 1 mM as compared with that of a reference agent. In some embodiments, an inventive method screens for modulators of PRPK, TPRKB, OSGEP, LAGE3 and its homologs, PRPK-TPRKB complex and/or KEOPS complex by identifying agents that inhibit cell proliferation. In some embodiments, an inventive method screens for modulators of PRPK, TPRKB, OSGEP, LAGE3 and its homologs, PRPK-TPRKB complex and/or KEOPS complex by identifying agents that inhibit B cell proliferation. In some embodiments, an inventive method screens for modulators of PRPK, TPRKB, OSGEP, LAGE3 and its homologs, PRPK-TPRKB complex and/or KEOPS complex by identifying agents that induce IL-2 production. In some embodiments, an inventive method screens for modulators of PRPK, TPRKB, OSGEP, LAGE3 and its homologs, PRPK-TPRKB complex and/or KEOPS complex by identifying agents that inhibit TNF-α production. In some embodiments, an inventive method screens for modulators of PRPK, TPRKB, OSGEP, LAGE3 and its homologs, PRPK-TPRKB complex and/or KEOPS complex by identifying agents that induce TNF-α production. In some embodiments, an inventive method screens for modulators of PRPK, TPRKB, OSGEP, LAGE3 and its homologs, PRPK-TPRKB complex and/or KEOPS complex by identifying agents that treat the symptoms of inflammation, inflammatory disease and/or autoimmune disease. In some embodiments, an inventive method screens for modulators of PRPK, TPRKB, OSGEP, LAGE3 and its homologs, PRPK-TPRKB complex and/or KEOPS complex by identifying agents that treat the symptoms of an oncogenic or cancerous condition. In some embodiments, an inventive method identifies modulators of PRPK, PRPK-TPRKB complex and/or KEOPS complex by identifying agents that modulate PRPK kinase activity. In yet other embodiments, the inventive method identifies modulators of PRPK, TPRKB, OSGEP, LAGE3 and its homologs, PRPK-TPRKB complex and/or KEOPS complex by identifying agents that modulate expression and/or levels of PRPK, TPRKB, OSGEP, and/or LAGE3 and its homologs. In some embodiments, an inventive method screens for modulators of PRPK, TPRKB, OSGEP, LAGE3 and its homologs, PRPK-TPRKB complex and/or KEOPS complex by identifying agents that activate natural killer cells. In some embodiments, an inventive method screens for modulators of PRPK, TPRKB, OSGEP, LAGE3 and its homologs, PRPK-TPRKB complex and/or KEOPS complex by identifying agents that induce immune synapse formation.

As used herein, the phrase "biological target" refers to (1) a PRPK protein, a nucleic acid encoding PRPK, and/or homolog, portion, variant, mutant, and/or derivative thereof; (2) a TPRKB protein, a nucleic acid encoding TPRKB, and/or homolog, portion, variant, mutant, and/or derivative thereof; (3) a OSGEP protein, a nucleic acid encoding OSGEP, and/or homolog, portion, variant, mutant, and/or derivative thereof; (4) an LAGE3 and its homologs protein, a nucleic acid encoding LAGE3 and its homologs, and/or homolog, portion, variant, mutant, and/or derivative thereof; and/or (5) a complex of any two or more of PRPK, TPRKB, OSGEP, and/or LAGE3 and its homologs.

The efficacy of the test agent may be assessed by generating dose response curves from data obtained using various concentrations of the test agent. Moreover, a control assay may be performed to provide a baseline for comparison. In certain embodiments, a control assay is performed in the absence of a candidate substance. In certain embodiments, a control assay is performed in the presence of a reference agent.

In some embodiments, agents according to the invention inhibit and/or activate PRPK, TPRKB, OSGEP, LAGE3 and its homologs, PRPK-TPRKB complex and/or KEOPS complex by at least about 10%, 15%, 20%, 30%, 40%, 50%, 60%, 70%, 80%, 90%, 95%, 99% or more as compared with the activity observed under otherwise identical conditions lacking a test agent. In some embodiments, agents according to the invention inhibit and/or activate PRPK, TPRKB, OSGEP, LAGE3 and its homologs, PRPK-TPRKB complex and/or KEOPS complex by at least about 10%, 15%, 20%, 30%, 40%, 50%, 60%, 70%, 80%, 90%, 95%, 99% or more as compared with the activity observed under comparable conditions using a reference standard.

It will be understood that all screening methods of the present invention are useful in themselves notwithstanding the fact that effective agents may not be found. The invention provides methods for screening for test agents, not solely methods of finding effective agents.

Screening

In some embodiments, screening for modulators of PRPK, TPRKB, OSGEP, LAGE3 and its homologs, PRPK-TPRKB complex and/or KEOPS complex is employed. In some embodiments, high throughput screening for modulators of PRPK, TPRKB, OSGEP, LAGE3 and its homologs, PRPK-TPRKB complex and/or KEOPS complex is employed. In some embodiments, such screening identifies substances that bind to PRPK, TPRKB, OSGEP, LAGE3 and its homologs, PRPK-TPRKB complex and/or KEOPS complex.

In high throughput assays of the invention, it is possible to screen up to several thousand test agents in a single day. Each well of a microtiter plate can be used to run a separate assay against a selected test agent, or, if concentration and/or incubation time effects are to be observed, every 5-10 wells can test a single test agent. Thus, a single standard microtiter plate can assay 96 test agents. If 1536 well plates are used, then a single plate can easily assay from about 100 to about 1500 different test agents. It is possible to assay many plates per day; assay screens for up to about 6,000, 20,000, 50,000, or more than 100,000 different test agents are possible.

For a solid state reaction, the biological target of interest may be bound to the solid state component, directly or indirectly, via covalent and/or non covalent linkage e.g., via a tag. The tag may comprise any of a variety of components. In general, a substance which binds the tag (a tag binder) is fixed to a solid support, and the tagged molecule of interest is attached to the solid support by interaction of the tag and/or the tag binder.

A number of tags and/or tag binders may be used, based upon known molecular interactions well described in the literature. For example, where a tag has a natural binder, for example, biotin, protein A, and/or protein G, it may be used in conjunction with appropriate tag binders (avidin, streptavidin, neutravidin, the Fc region of an immunoglobulin, etc.). Antibodies to molecules with natural binders such as biotin and/or appropriate tag binders are widely available (Sigma Immunochemicals, 1998 catalogue, St. Louis, Mo.).

Similarly, any haptenic and/or antigenic compound may be used in combination with an appropriate antibody to form a tag/tag binder pair. Thousands of specific antibodies are commercially available and many additional antibodies are described in the literature. For example, in one common configuration, the tag is a first antibody and the tag binder is a second antibody which recognizes the first antibody. In addition to antibody-antigen interactions, receptor-ligand interactions are appropriate as tag and/or tag-binder pairs, including but not limited to transferrin, c-kit, viral receptor ligands, cytokine receptors, chemokine receptors, interleukin receptors, immunoglobulin receptors and/or antibodies, the cadherin family, the integrin family, the selectin family, etc. (see, e.g., Pigott et al., *The Adhesion Molecule Facts Book I*, 1993). Similarly, toxins and/or venoms; viral epitopes; hormones (e.g. opiates, steroids, etc.); intracellular receptors (e.g. which mediate the effects of various small ligands, including steroids, thyroid hormone, retinoids, vitamin D, and/or peptides); drugs; lectins; carbohydrates; nucleic acids (linear and/or cyclic polymer configurations); proteins; phospholipids; and/or antibodies may interact with various cell receptors.

Synthetic polymers, such as polyurethanes, polyesters, polycarbonates, polyureas, polyamides, polyethyleneimines, polyarylene sulfides, polysiloxanes, polyimides, and/or polyacetates may form appropriate tags and/or tag binders. Many other tag/tag binder pairs are useful in assay systems described herein, as would be apparent to one skilled in the art.

Common linkers such as peptides, polyethers, and the like may serve as tags and may include polypeptide sequences, such as poly-Gly sequences of between about 5 and 200 amino acids. Such flexible linkers are known to persons of skill in the art. For example, poly(ethelyne glycol) linkers are available from Shearwater Polymers, Inc. (Huntsville, Ala.). These linkers optionally have amide linkages, sulfhydryl linkages, and/or heterofunctional linkages.

Tag binders are fixed to solid substrates using any of a variety of methods currently available. Solid substrates are commonly derivatized and/or functionalized by exposing all and/or a portion of the substrate to a chemical reagent which fixes a chemical group to the surface which is reactive with a portion of the tag binder. For example, groups which are suitable for attachment to a longer chain portion include amines, hydroxyl, thiol, and/or carboxyl groups Aminoalkylsilanes and/or hydroxyalkylsilanes may be used to functionalize a variety of surfaces, such as glass surfaces. The construction of such solid phase biopolymer arrays is well described in the literature (see, e.g., Merrifield, 1963, *J. Am. Chem. Soc.* 85:2149, describing solid phase synthesis of, e.g., peptides; Geysen et al., 1987, *J. Immun. Meth.* 102:259, describing synthesis of solid phase components on pins; Frank et al., 1988, *Tetrahedron* 44:6031, describing synthesis of various peptide sequences on cellulose disks); Fodor et al., 1991, *Science*, 251:767; Sheldon et al., 1993, *Clinical Chemistry* 39(4):718; and Kozal et al., 1996, *Nature Medicine* 2:753; all describing arrays of biopolymers fixed to solid substrates). Non-chemical approaches for fixing tag binders to substrates include other common methods, such as heat, cross-linking by UV radiation, and the like.

In Vitro Assays

The present invention provides in vitro methods for screening a modulator of PRPK, TPRKB, OSGEP, LAGE3 and its homologs, PRPK-TPRKB complex and/or KEOPS complex. For example, in some embodiments, a method generally comprises steps of: (1) providing a system comprising PRPK, TPRKB, OSGEP, LAGE3 and its homologs, PRPK-TPRKB complex and/or KEOPS complex; (2) providing a test agent; (3) contacting the test agent with the system; and (4) measuring and/or detecting modulation of PRPK, TPRKB, OSGEP, LAGE3 and its homologs, PRPK-TPRKB complex and/or KEOPS complex by the test agent.

In general, PRPK, TPRKB, OSGEP, LAGE3 and its homologs, PRPK-TPRKB complex and/or KEOPS complex is provided and brought directly and/or indirectly into contact with a test agent. Then, modulation of PRPK, TPRKB, OSGEP, LAGE3 and its homologs, PRPK-TPRKB complex and/or KEOPS complex by the test agent is detected and/or measured. Thereafter, suitable agents may be isolated and/or analyzed. For the screening of libraries, the use of high-throughput assays, which are known to the skilled person, are commercially available, and are described herein.

In some embodiments, in vitro assays comprise binding assays. Binding of a candidate substance to a biological target (e.g. PRPK, TPRKB, OSGEP, LAGE3 and its homologs, PRPK-TPRKB complex and/or KEOPS complex) may, in and of itself, be inhibitory, due to steric, allosteric, and/or charge-charge interactions. The biological target may be free in solution, fixed to a support, and/or expressed in and/or on the surface of a cell. The biological target and/or the test agent may be labeled, thereby permitting detection of binding. The biological target is frequently the labeled species, decreasing the chance that the labeling will interfere with and/or enhance binding. Competitive binding formats may be performed in which one of the test agents is labeled, and one may measure the amount of free label versus bound label to determine the effect on binding.

In some embodiments, binding assays involve exposing a biological target to a test agent and detecting binding between the biological target and the test agent. The binding assay may be conducted in vitro (e.g. in a test tube, comprising substantially only the components mentioned; in cell-free extracts; and/or in substantially purified components). Alternatively or additionally, the assays may be conducted in cyto and/or in vivo (e.g. within a cell, tissue, organ, and/or organism; described in further detail below).

In certain embodiments, a test agent is contacted with a biological target and an effect detected. In one assay, for example, a test agent is contacted with PRPK protein, and binding to PRPK protein is tested. Similar assays may be performed for TPRKB, OSGEP, LAGE3 and its homologs, PRPK-TPRKB complex and/or KEOPS complex. It will be appreciated that fragments, portions, homologs, variants, and/or derivatives of PRPK, TPRKB, OSGEP, and/or LAGE3 and its homologs may be employed.

In some embodiments, an assay for identifying agents that bind to a biological target, which is immobilized on a solid support, with a non-immobilized test agent is used to determine whether and/or to what extent the biological target and test agent bind to each other. Alternatively, the test agent may be immobilized and the biological target non-immobilized. Such assays may be used to identify agents capable of binding to PRPK, TPRKB, OSGEP, LAGE3 and its homologs, PRPK-TPRKB complex and/or KEOPS complex.

In one embodiment, an antibody that recognizes the biological target (e.g. a PRPK antibody) is bound to a solid support (e.g. Protein-A beads). The antibody is contacted with the biological target, which binds to the immobilized antibody. The resulting complex is then brought into contact with the test agent (purified protein, cellular extract, combinatorial library, etc.). If the test agent interacts with the biological target, the test agent will become indirectly immobilized to the solid support. Presence of the test agent on the solid support can be assayed by any standard technique known in the art (including, but not limited to, western blotting). This type of assay is known in the art as an "immunoprecipitation" assay.

In one embodiment, a biological target (e.g., PRPK, TPRKB, OSGEP, LAGE3 and its homologs, PRPK-TPRKB complex and/or KEOPS complex) is immobilized on beads, such as agarose beads. In certain embodiments, PRPK, TPRKB, OSGEP, LAGE3 and its homologs, and/or a characteristic portion thereof is expressed as a GST-fusion protein in bacteria, yeast, insect, and/or higher eukaryotic cell line and/or purified from crude cell extracts using glutathione-agarose beads. As a control, binding of the test agent, which is not a GST-fusion protein, to the immobilized biological target is determined in the absence of biological target. The binding of the test agent to the immobilized biological target is then determined. This type of assay is known in the art as a "GST pulldown" assay. Alternatively or additionally, the test agent may be immobilized and the biological target non-immobilized.

It is possible to perform this type of assay using different affinity purification systems for immobilizing one of the components, for example Ni-NTA agarose- and/or histidine-tagged components.

Binding of a biological target to a test agent may be determined by a variety of methods well-known in the art. For example, a non-immobilized component may be labeled (with for example, a radioactive label, an epitope tag, and/or an enzyme-antibody conjugate). Alternatively, binding may be determined by immunological detection techniques. For example, a reaction mixture may be Western blotted and the blot probed with an antibody that detects the non-immobilized component. Alternatively or additionally, enzyme linked immunosorbent assay (ELISA) may be utilized to assay for binding.

The activity of PRPK, PRPK-TPRKB complex and/or KEOPS complex modulators of the present invention may be determined by, for example, assaying for kinase activity of PRPK. In such assays PRPK and/or a characteristic portion thereof produced by recombinant means is contacted with a substrate in the presence of a suitable phosphate donor (e.g. ATP) containing radiolabeled phosphate, and PRPK-dependent incorporation of radiolabel into the substrate is measured. By "substrate," one means any substance containing a suitable hydroxyl moiety that acts as an acceptor for the γ-phosphate group transferred from a donor molecule such as ATP in a reaction catalyzed by PRPK. The substrate may be an endogenous substrate of PRPK (e.g., p53). The substrate may be a protein or peptide, and the phosphorylation reaction may occur on a substrate serine and/or threonine residue. It is well-known to those skilled in the art that non-natural substrates can act as suitable substrates in kinase assays such as that described above, and examples of specific substrates which are commonly employed in such assays include, but are not limited to, histone proteins or any myelin basic protein.

It is well known to those skilled in the art that detection of kinase-dependent substrate phosphorylation can be effected by a number of means other than measurement of radiolabeled phosphate incorporation into the substrate. For example, incorporation of phosphate groups can affect physicochemical properties of the substrate, such as electrophoretic mobility, light absorbance, fluorescence and/or phosphorescence, chromatographic properties and the like. Such alterations of substrate physicochemical properties can be readily measured by one skilled in the art and used as an indicator of kinase activity.

In Cyto Assays

In some embodiments, the present invention provides methods of screening for modulators of PRPK, TPRKB, OSGEP, LAGE3 and its homologs, PRPK-TPRKB complex and/or KEOPS complex wherein the test agent is contacted with a cell. The cell can then be assayed for various parameters associated with activity of PRPK, TPRKB, OSGEP, LAGE3 and its homologs, PRPK-TPRKB complex and/or KEOPS complex. In some embodiments, the cell overexpresses one or more members of the PRPK-TPRKB complex and/or of the KEOPS complex and/or contains a modification of a biological pathway in which one or both of these complexes operates. The present invention provides such overexpressing and/or modified cells; those of skill in the art, reading the present disclosure, would be well apprised of the boundaries of such cells and well aware of the wide variety of established and readily available strategies for constructing, characterizing, and/or utilizing such cells.

In certain embodiments, cells may be directly assayed for binding between two or more of PRPK, TPRKB, OSGEP, and LAGE3 and its homologs Immunohistochemical techniques, confocal techniques, and/or other techniques to assess binding are well known to those of skill in the art. Various cell lines may be utilized for such screening assays, including cells specifically engineered for this purpose. Examples of cells used in the screening assays include Jeko-1, NCI-H929, Jurkat, PBMCs (peripheral blood mononuclear cells), HS-Sultan, multiple myeloma cell lines, HEK-293FT, Raji, Daudi, Ramos, B cell lines, T cell lines. The cell may be a stimulated cell, such as a cell stimulated with a growth factor. One of skill in the art would understand that the invention disclosed herein encompasses a wide variety of in cyto assays for measuring parameters that correlate with the activity of PRPK, TPRKB, OSGEP, LAGE3 and its homologs, PRPK-TPRKB complex and/or KEOPS complex.

Depending on the assay, cell and/or tissue culture may be required. The cell may be examined using any of a number of different physiologic assays, as discussed above for binding between two or more of PRPK, TPRKB, OSGEP, and LAGE3 and its homologs. Alternatively, molecular analysis may be performed, including, but not limited to, western blotting to monitor protein expression and/or test for protein-protein interactions; northern blotting, differential display of RNA, and/or microarray analysis to monitor mRNA expression; kinase assays to monitor phosphorylation; mass spectrometry to monitor other chemical modifications; etc.

The present invention provides methods for identifying agents that bind to PRPK, TPRKB, OSGEP, LAGE3 and its homologs, PRPK-TPRKB complex and/or KEOPS complex and, therefore, may modulate activity of PRPK, TPRKB, OSGEP, LAGE3 and its homologs, PRPK-TPRKB complex and/or KEOPS complex. One in cyto method of identifying substances that bind to PRPK, TPRKB, OSGEP, LAGE3 and its homologs, PRPK-TPRKB complex and/or KEOPS complex is the two-hybrid system assay (Fields et al., 1994, *Trends in Genetics* 10:286; and Colas et al., 1998, *TIBTECH* 16:355). In this assay, yeast cells express a first fusion protein consisting of the biological target according to the invention (e.g. PRPK, TPRKB, OSGEP, LAGE3 and its homologs, PRPK-TPRKB complex and/or KEOPS complex) and a DNA-binding domain of a transcription factor such as Gal4 and/or LexA. The cells additionally contain a reporter gene whose promoter contains binding sites for the corresponding DNA-binding domain. By transforming the cells with a vector that expresses a second fusion protein consisting of a candidate substance fused to an activation domain (e.g. from Gal4 and/or herpes simplex virus VP16) the expression of the reporter gene may be greatly increased if the test agent interacts with the biological target.

Another assay is based on solid phase-bound biological target and its interaction with the test agents to be screened.

Thus, a biological target (e.g. PRPK, TPRKB, OSGEP, LAGE3 and its homologs, PRPK-TPRKB complex and/or KEOPS complex) may contain a detectable marker, such as a radioactive, fluorescent, and/or luminescent label. Furthermore, candidate substances can be coupled to other substances which permit indirect detection (e.g. by means of employing an enzyme which uses a chromogenic substrate and/or by means of binding a detectable antibody). Changes in the conformation of PRPK, TPRKB, OSGEP, LAGE3 and its homologs, PRPK-TPRKB complex and/or KEOPS complex as the result of an interaction with a test agent may be detected, for example, by the change in the emission of the detectable marker. Alternatively or additionally, the solid phase-bound protein complexes may be analyzed by means of mass spectrometry.

In some embodiments, screening assays may assay activity of PRPK, TPRKB, OSGEP, LAGE3 and its homologs, PRPK-TPRKB complex and/or KEOPS complex by monitoring the downstream cellular effects of activity of PRPK, TPRKB, OSGEP, LAGE3 and its homologs, PRPK-TPRKB complex and/or KEOPS complex. Such effects include, but are not limited to, phosphorylation of p53 and signaling effects in the PI3K/AKT pathway, and/or other cellular responses, such as growth, growth arrest, differentiation, changes in glycosylation, changes in gene expression, regulation of transcription, effects on telomere length, effects on cytokine production and/or apoptosis.

In another embodiment, levels PRPK, TPRKB, OSGEP, and/or LAGE3 and its homologs are determined by measuring the level of protein and/or mRNA. The level of protein and/or characteristic portions thereof are measured using immunoassays such as western blotting and/or ELISA using antibodies that selectively bind to PRPK, TPRKB, OSGEP, and/or LAGE3 and its homologs. For measurement of mRNA, amplification (e.g., using PCR, LCR) and/or hybridization assays (e.g., northern hybridization, RNAse protection, dot blotting) may be used. The level of protein and/or mRNA is detected using directly- and/or indirectly-labeled detection agents, e.g., fluorescently and/or radioactively labeled nucleic acids, radioactively and/or enzymatically labeled antibodies, etc. as described herein.

Alternatively or additionally, expression of PRPK, TPRKB, OSGEP, and/or LAGE3 and its homologs may be measured using a reporter gene system. Such a system may be devised using a PRPK, TPRKB, OSGEP, and/or LAGE3 and its homologs protein promoter operably-linked to a reporter gene such as chloramphenicol acetyltransferase, firefly luciferase, bacterial luciferase, O-galactosidase, and/or alkaline phosphatase. Furthermore, PRPK, TPRKB, OSGEP, and/or LAGE3 and its homologs may be used as an indirect reporter via attachment to a second reporter such as red and/or green fluorescent protein (see, e.g., Mistili et al., 1997, *Nature Biotech.* 15:961). The reporter construct is typically transfected into a cell. After treatment with a candidate substance, the amount of reporter gene transcription, translation, and/or activity is measured according to standard techniques known to those of skill in the art.

In some embodiments, the present invention provides methods to determine whether PRPK can induce phosphorylation of p53 in vivo. In such methods, cells are transfected with vectors expressing wild-type or mutant PRPK and/or p53. Cell extracts or whole cells are prepared at specified time points after transfection, and the degree of phosphorylation of p53 is analyzed by western blotting or mass-spectrometry (lysates) or by in-cell western, immunofluorescence, or high content imaging (whole cells).

In Vivo Assays

In vivo assays involve the use of various animal models, including transgenic animals that have been engineered to have specific defects and/or carry markers that can be used to measure the ability of a candidate substance to reach and/or affect different cells within the organism. Due to their size, ease of handling, and/or information on their physiology and/or genetic make-up, mice are one embodiment, especially for transgenics. However, other animals are suitable as well, including rats, rabbits, hamsters, guinea pigs, gerbils, woodchucks, cats, dogs, sheep, goats, pigs, cows, horses and/or monkeys (including chimps, gibbons and/or baboons). Assays for modulators may be conducted using an animal model derived from any of these species and/or other useful species not listed herein.

In such assays, one or more test agents are administered to an animal, and the ability of the test agent(s) to alter one or more characteristics, as compared to a similar animal not treated with the test agent(s), identifies a modulator. The characteristics may be any of those discussed herein with regard to the symptoms associated with cell proliferation, IL-2 production, TNF-α production, and any other effect of PRPK, TPRKB, OSGEP, LAGE3 and its homologs, PRPK-TPRKB complex and/or KEOPS complex (e.g., inflammation, inflammatory disease, autoimmune disease, oncogenic or cancerous conditions, etc).

The present invention provides methods of screening for an agent that may treat, stabilize, and/or delay the onset of a disease, condition, or disorder associated with PRPK, TPRKB, OSGEP, LAGE3 and its homologs, PRPK-TPRKB complex and/or KEOPS complex. In some embodiments, the agent comprises a modulator of PRPK, TPRKB, OSGEP, LAGE3 and its homologs, PRPK-TPRKB complex and/or KEOPS complex. Treatment of these animals with agents according to the invention will involve the administration of the substance, in an appropriate form, to the animal. Administration will be by any route that could be utilized for clinical and/or non-clinical purposes, including but not limited to oral, nasal, buccal, and/or topical. Alternatively or additionally, administration may be by intratracheal instillation, bronchial instillation, intradermal, subcutaneous, intramuscular, intraperitoneal, inhalation, and/or intravenous injection (e.g., systemic intravenous injection), regional administration via blood and/or lymph supply, and/or direct administration to an affected site.

Accordingly, in one aspect, the invention provides a screening system, including methods and/or compositions, for determining whether an agent is useful for treating, stabilizing, and/or delaying the onset of a disease, condition, or disorder associated with PRPK, TPRKB, OSGEP, LAGE3 and its homologs, PRPK-TPRKB complex and/or KEOPS complex in a mammal. In some embodiments, the candidate substance is determined to treat, stabilize, and/or delay the onset of a disease, condition, or disorder associated with PRPK, TPRKB, OSGEP, LAGE3 and its homologs, PRPK-TPRKB complex and/or KEOPS complex if the substance improves, stabilizes, and/or delays the onset of the symptoms associated with such as disease, disorder, or condition.

Determining the effectiveness of a compound in vivo may involve a variety of different criteria. Measuring toxicity and/or dose response may be performed in animals in a more meaningful fashion than in in vitro and/or in cyto assays. In vivo assays may include animal disease models for multiple myeloma, angiogenesis inhibition, chronic lymphocytic leukemia, or acute lymphoblastic leukemia, solid tumor animal models, any oncology-related animal models, inflammation animal models and auto-immune disease animal models.

Methods of Use

The present invention provides methods of treating a disease, condition, or disorder associated with PRPK, TPRKB, OSGEP, LAGE3 and its homologs, PRPK-TPRKB complex and/or KEOPS complex. In some embodiments, the present invention provides methods of treating a disease, condition, or disorder associated with cell proliferation, IL-2 production, or TNF-α production, natural killer activation. In certain embodiments, such methods involve modulating PRPK, TPRKB, OSGEP, LAGE3 and its homologs, PRPK-TPRKB complex and/or KEOPS complex. In certain embodiments, such methods involve activating PRPK, TPRKB, OSGEP, LAGE3 and its homologs, PRPK-TPRKB complex and/or KEOPS complex. In certain embodiments, such methods involve inhibiting PRPK, TPRKB, OSGEP, LAGE3 and its homologs, PRPK-TPRKB complex and/or KEOPS complex.

In some embodiments, the present invention provides methods of inhibiting cell proliferation comprising contacting a cell with an agent that modulates a PRPK/TPRKB complex and/or a KEOPS complex and/or any subunit or component thereof, and optionally further comprising a step of detecting a decrease in cell proliferation compared to a control. In some embodiments, the present invention provides methods of inhibiting B cell proliferation comprising contacting a B cell with an agent that modulates a PRPK/TPRKB complex and/or a KEOPS complex and/or any subunit or component thereof, and optionally further comprising a step of detecting a decrease in B cell proliferation compared to a control. In some embodiments, the present invention provides methods of inducing IL-2 production comprising contacting a cell with an agent that modulates a PRPK/TPRKB complex and/or a KEOPS complex and/or any subunit or component thereof, and optionally further comprising a step of detecting an increase in IL-2 production compared to a control. In some embodiments, the present invention provides methods of inhibiting TNF-α comprising contacting a cell with an agent that modulates a PRPK/TPRKB complex and/or a KEOPS complex and/or any subunit or component thereof, and optionally further comprising a step of detecting a decrease in TNF-α production compared to a control.

In some embodiments, the present invention provides methods of treating a disease, condition, or disorder associated with PRPK, TPRKB, OSGEP, LAGE3 and its homologs, PRPK-TPRKB complex and/or KEOPS complex. In certain embodiments, a disease, disorder, or condition treated by an inventive method is inflammation, inflammatory disease, autoimmune disease, an oncogenic or cancerous condition, rheumatoid arthritis, osteoarthritis, inflammatory bowel disease, sepsis, lupus, erythema nodosum leprosum, Crohn's disease, ulcerative colitis, multiple myeloma, myelodysplastic syndrome, multiple sclerosis, schizophrenia, host-versus-graft disease, HIV, diabetes, bacterial infection, emesis, cardiovascular disease, malaria, hypertension, arteriosclerosis, asthma, amyotrophic lateral sclerosis, ankylosing spondylitis, cachexia, colorectal cancer, head and neck cancer, idiopathic pulmonary fibrosis, leukemia, lung cancer, melanoma, pain, or prostate cancer. In certain embodiments, an agent used in the methods of the invention is a hypnotic, sedative, anticoagulant, salvage therapy, immunostimulant, immunosuppressant, adjuvant, fungicide, or nervous system agent.

In certain aspects of the invention, the method further comprises providing a pharmaceutical composition comprising an agent that modulates PRPK, TPRKB, OSGEP, LAGE3 and its homologs, PRPK-TPRKB complex and/or KEOPS complex. In certain aspects of the invention, the method further comprises providing a pharmaceutical composition comprising an agent of formula I, II, or III. In other aspects, the pharmaceutical composition comprising the candidate substance is administered to a cell, such as one in a patient suffering from a disease, condition, or disorder associated with PRPK, TPRKB, OSGEP, LAGE3 and its homologs, PRPK-TPRKB complex and/or KEOPS complex.

In yet other embodiments, the present invention provides methods of treating a disease, condition, or disorder associated with PRPK, TPRKB, OSGEP, LAGE3 and its homologs, PRPK-TPRKB complex and/or KEOPS complex comprising steps of (1) providing a patient exhibiting symptoms of a disease, condition, or disorder associated with PRPK, TPRKB, OSGEP, LAGE3 and its homologs, PRPK-TPRKB complex and/or KEOPS complex, and (2) administering an agent that modulates PRPK, TPRKB, OSGEP, LAGE3 and its homologs, PRPK-TPRKB complex and/or KEOPS complex. In certain embodiments, the present invention permits identification and/or classification of individuals who suffer from or are susceptible to a disease, condition, or disorder associated with PRPK, TPRKB, OSGEP, LAGE3 and its homologs, PRPK-TPRKB complex and/or KEOPS complex and/or who are likely (or unlikely) to respond to treatment with a modulator of a disease, condition, or disorder associated with PRPK, TPRKB, OSGEP, LAGE3 and its homologs, PRPK-TPRKB complex and/or KEOPS complex.

Pharmaceutical Compositions

The present invention provides modulators of PRPK, TPRKB, OSGEP, LAGE3 and its homologs, PRPK-TPRKB complex and/or KEOPS complex. In some embodiments, the present invention provides for pharmaceutical compositions comprising modulators of PRPK, TPRKB, OSGEP, LAGE3 and its homologs, PRPK-TPRKB complex and/or KEOPS complex, as described herein. The present invention provides pharmaceutical compositions comprising a therapeutically effective amount of one or more modulator(s) of PRPK, TPRKB, OSGEP, LAGE3 and its homologs, PRPK-TPRKB complex and/or KEOPS complex appropriately formulated for administration to a subject. Such pharmaceutical compositions may optionally comprise one or more additional therapeutically-active substances.

In accordance with one embodiment, a method of treating a disease, condition, or disorder associated with PRPK, TPRKB, OSGEP, LAGE3 and its homologs, PRPK-TPRKB complex and/or KEOPS complex is provided. The method comprises administering a pharmaceutical composition comprising at least one modulator of PRPK, TPRKB, OSGEP, LAGE3 and its homologs, PRPK-TPRKB complex and/or KEOPS complex of the present invention to a patient in need thereof. Modulators of PRPK, TPRKB, OSGEP, LAGE3 and its homologs, PRPK-TPRKB complex and/or KEOPS complex may be administered with other medications used to treat the symptoms of the particular disease, disorder, or condition to be treated. In some embodiments, the compositions are administered to humans.

The invention encompasses the preparation and/or use of pharmaceutical compositions comprising a modulator of PRPK, TPRKB, OSGEP, LAGE3 and its homologs, PRPK-TPRKB complex and/or KEOPS complex as an active ingredient. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, and/or a combination of these. The active ingredient may be present in the pharmaceutical composition in the form of a physiologically acceptable ester and/or salt, such as in combination with a physiologically acceptable cation and/or anion, as is well known in the art.

As used herein, the term "physiologically acceptable" ester and/or salt means an ester and/or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier and/or one or more other accessory ingredients, and then, if necessary and/or desirable, shaping and/or packaging the product into a desired single- or multi-dose unit.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the pharmaceutical compositions of the invention is contemplated include, but are not limited to, humans and/or other primates; mammals, including commercially relevant mammals such as cattle, pigs, horses, sheep, cats, and/or dogs; and/or birds, including commercially relevant birds such as chickens, ducks, geese, and/or turkeys.

A pharmaceutical composition of the invention may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

The relative amounts of the active ingredient, the pharmaceutically acceptable carrier, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

In general, a pharmaceutical composition will include a therapeutic agent in addition to one or more additional ingredients, including, but are not limited to, one or more of the following: excipients; surface active agents; dispersing agents; inert diluents; granulating and/or disintegrating agents; binding agents; lubricating agents; sweetening agents; flavoring agents; coloring agents; preservatives; physiologically degradable compositions such as gelatin; aqueous vehicles and/or solvents; oily vehicles and/or solvents; suspending agents; dispersing and/or wetting agents; emulsifying agents, demulcents; buffers; salts; thickening agents; fillers; emulsifying agents; antioxidants; antibiotics; antifungal agents; stabilizing agents; pharmaceutically acceptable polymeric and/or hydrophobic materials; and/or combinations thereof, as suited to the particular dosage form desired. *Remington: The Science and Practice of Pharmacy* (20$^{st}$ ed., Lippincott Williams & Wilkins, 2005) discloses other additional ingredients which may be used in formulating pharmaceutically acceptable compositions and/or known techniques for the preparation thereof.

The pharmaceutical compositions may be prepared, packaged, and/or sold in the form of a sterile injectable aqueous or oily suspension and/or solution. This suspension and/or solution may be formulated according to the known art, and may comprise, in addition to the active ingredient, additional ingredients such as the dispersing agents, wetting agents, and/or suspending agents described herein. Such sterile injectable formulations may be prepared using a non toxic parenterally acceptable diluent and/or solvent, such as water and/or 1,3 butane diol, for example. Other acceptable diluents and/or solvents include, but are not limited to, Ringer's solution, isotonic sodium chloride solution, and/or fixed oils such as synthetic mono- and/or di-glycerides. Other parentally-administrable formulations which are useful include those which comprise the active ingredient in microcrystalline form, in a liposomal preparation, and/or as a component of a biodegradable polymer systems. Compositions for sustained release and/or implantation may comprise pharmaceutically acceptable polymeric and/or hydrophobic materials such as an emulsion, an ion exchange resin, a sparingly soluble polymer, and/or a sparingly soluble salt.

In order to prolong the effect of a compound of the present invention, it is often desirable to slow the absorption of the compound from subcutaneous and/or intramuscular injection. This may be accomplished by the use of a liquid suspension of crystalline and/or amorphous material with poor water solubility. The rate of absorption of the compound then depends upon its rate of dissolution that, in turn, may depend upon crystal size and/or crystalline form. Alternatively or additionally, delayed absorption of a parenterally administered compound form can be accomplished by dissolving and/or suspending the compound in an oil vehicle. Injectable depot forms are made by forming microencapsule matrices of the compound in biodegradable polymers such as polylactide-polyglycolide. Depending upon the ratio of compound to polymer and/or the nature of the particular polymer employed, the rate of compound release can be controlled. Examples of other biodegradable polymers include poly (orthoesters) and/or poly(anhydrides). Depot injectable formulations are prepared by entrapping the compound in liposomes and/or microemulsions that are compatible with body tissues.

Inventive injectable formulations may be sterilized, for example, by filtration through a bacterial-retaining filter, and/or by incorporating sterilizing agents in the form of sterile solid compositions which may be dissolved and/or dispersed in sterile water and/or other sterile injectable medium prior to use.

A formulation of a pharmaceutical composition of the invention suitable for oral administration may be prepared, packaged, and/or sold in the form of a discrete solid dose unit including, but not limited to, a tablet, a hard or soft capsule, a cachet, a troche, and/or a lozenge, each containing a predetermined amount of the active ingredient. Other formulations suitable for oral administration include, but are not limited to, a powdered and/or granular formulation, an aqueous or oily suspension, an aqueous or oily solution, and/or an emulsion. As used herein, an "oily" liquid is one which comprises a carbon-containing liquid molecule and which exhibits a less polar character than water.

Powdered and/or granular formulations of a pharmaceutical preparation of the invention may be prepared using known methods. Such formulations may be administered directly to an apparatus, used, for example, to form tablets, to fill capsules, and/or to prepare an aqueous or oily suspension and/or solution by addition of an aqueous or oily vehicle thereto.

A pharmaceutical composition of the invention may be prepared, packaged, and/or sold in the form of oil in water emulsion and/or a water-in-oil emulsion. The oily phase may be a vegetable oil such as olive and/or arachis oil, a mineral oil such as liquid paraffin, and/or a combination of these. Such compositions may further comprise one or more emulsifying agents such as naturally occurring gums such as gum acacia and/or gum tragacanth, naturally occurring phosphatides such as soybean and/or lecithin phosphatide, esters and/or partial esters derived from combinations of fatty acids and/or hexitol anhydrides such as sorbitan monooleate, and/or condensation products of such partial esters with ethylene oxide such as polyoxyethylene sorbitan monooleate. These emulsions may contain additional ingredients including, for example, sweetening and/or flavoring agents.

Liquid formulations of a pharmaceutical composition of the invention which are suitable for oral administration include, but are not limited to, aqueous may be prepared, packaged, and/or sold either in liquid form and/or in the form of a dry product intended for reconstitution with water and/or another suitable vehicle prior to use.

Liquid dosage forms for oral administration include, but are not limited to, pharmaceutically acceptable emulsions, microemulsions, solutions, suspensions, syrups and/or elixirs. In addition to any active compounds, the liquid dosage forms may contain inert diluents commonly used in the art such as, for example, water, isotonic saline, and/or other solvents, solubilizing agents, and/or emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, sesame; soybean; apricot kernel; palm; peanut; safflower; coconut; olive; cocoa butter; palm kernel; shea butter; sunflower; almond; avocado; borage; carnauba; hazel nut; castor; cotton seed; evening primrose; orange roughy; rapeseed; rice bran; walnut; wheat germ; peach kernel; babassu; mango seed; black current seed; jojoba; macademia nut; sea buckthorn; sasquana; tsubaki; mallow; meadowfoam seed; coffee; emu; mink; grape seed; thistle; tea tree; pumpkin seed; kukui nut; and/or mixtures thereof), glycerol, tetrahydrofurfuryl alcohol, polyethylene glycols and/or fatty acid esters of sorbitan, ethyl alcohol, mineral oils such as liquid paraffin, and/or mixtures thereof.

Besides inert diluents, oral compositions may further comprise one or more additional ingredients including, but not limited to, suspending agents, dispersing and/or wetting agents, emulsifying agents, demulcents, preservatives, buffers, salts, flavorings, coloring agents, and/or sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and/or cellulose derivatives such as sodium carboxymethylcellulose, methylcellulose, hydroxypropylmethylcellulose.

Known dispersing and/or wetting agents include, but are not limited to, naturally occurring phosphatides such as lecithin, condensation products of an alkylene oxide with a fatty acid, with a long chain aliphatic alcohol, with a partial ester derived from a fatty acid and/or a hexitol, and/or with a partial ester derived from a fatty acid and/or a hexitol anhydride (e.g. polyoxyethylene stearate, heptadecaethyleneoxycetanol, polyoxyethylene sorbitol monooleate, and/or polyoxyethylene sorbitan monooleate, respectively). Known emulsifying agents include, but are not limited to, lecithin and/or acacia. Known preservatives include, but are not limited to, methyl, ethyl, and/or n-propyl para hydroxybenzoates, ascorbic acid, and/or sorbic acid. Known sweetening agents include, for example, glycerol, propylene glycol, sorbitol, sucrose, and/or saccharin. Known thickening agents for oily suspensions include, for example, beeswax, hard paraffin, and/or cetyl alcohol.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water and/or isotonic saline. Oily solvents include, for example, almond oil, peanut oil, oily esters, ethyl alcohol, vegetable oils such as arachis, olive, sesame, and/or coconut oil, fractionated vegetable oils, and/or mineral oils such as liquid paraffin.

Solid dosage forms for oral administration include capsules, tablets, pills, powders, and/or granules. Pharmaceutically acceptable excipients used in the manufacture of tablets include, but are not limited to, inert diluents, granulating and/or disintegrating agents, binding agents, and/or lubricating agents. Known dispersing agents include, but are not limited to, potato starch and/or sodium starch glycollate. Known surface active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and/or sodium phosphate. Known granulating and/or disintegrating agents include, but are not limited to, corn starch and/or alginic acid. Known binding agents include, but are not limited to, gelatin, acacia, pregelatinized maize starch, polyvinylpyrrolidone, and/or hydroxypropyl methylcellulose. Known lubricating agents include, but are not limited to, magnesium stearate, stearic acid, silica, and/or talc. Tablets may be non-coated and/or they may be coated using known methods to achieve delayed disintegration in the gastrointestinal tract of a subject, thereby providing sustained release and/or absorption of the active ingredient. By way of example, a material such as glyceryl monostearate and/or glyceryl distearate may be used to coat tablets. Further by way of example, tablets may be coated using methods described in U.S. Pat. Nos. 4,256,108; 4,160,452; and 4,265,874 to form osmotically-controlled release tablets. Tablets may further comprise a sweetening agent, a flavoring agent, a coloring agent, a preservative, and/or some combination of these in order to provide pharmaceutically elegant and/or palatable preparation.

Suitable binders include but are not limited to starch, PVP (polyvinyl pyrrolidone), low molecular weight HPC (hydroxypropyl cellulose), microcrystalline cellulose, low molecular weight HPMC (hydroxypropyl methylcellulose), low molecular weight carboxymethyl cellulose, ethylcellulose, alginates, gelatin, polyethylene oxide, acacia, dextrin, sucrose, magnesium aluminum silicate, and/or polymethacrylates.

Fillers include agents selected from the group consisting of microcrystalline cellulose, starch, lactitol, lactose, a suitable inorganic calcium salt, sucrose, glucose, mannitol, silicic acid, and/or a combination thereof. In some embodiments, the core comprises a binder and/or filler.

Incorporation of suitable disintegrant(s) into a solid dosage form may facilitate breakdown. Addition of disintegrant may facilitate release of active compound and/or achievement of concentration equilibration in the GI tract. Suitable disintegrants are known in the art and include but are not limited to, agar, calcium carbonate, potato and/or tapioca starch, alginic acid, certain silicates, sodium carbonate, crospovidone (cross-linked PVP), sodium carboxymethyl starch (sodium starch glycolate), cross-linked sodium carboxymethyl cellulose (croscarmellose), pregelatinized starch (starch 1500), microcrystalline starch, water insoluble starch, calcium carboxymethyl cellulose, magnesium aluminum silicate (Veegum) and/or a combination thereof.

Suitable surfactants are known in the art and include, e.g., poloxamer, polyoxyethylene ethers, polyoxyethylene sorbitan fatty acid esters polyoxyethylene fatty acid esters, polyethylene glycol fatty acid esters, polyoxyethylene hydrogenated castor oil, polyoxyethylene alkyl ether, polysorbates, cetyl alcohol, glycerol fatty acid esters (e.g., triacetin, glycerol monostearate, etc.), polyoxymethylene stearate, sodium lauryl sulfate, sorbitan fatty acid esters, sucrose fatty acid esters, benzalkonium chloride, polyethoxylated castor oil, and/or docusate sodium, etc., and/or combinations thereof. In some embodiments the core may further comprise a surfactant.

Solution retarding agents such as paraffin, absorption accelerators such as quaternary ammonium compounds, wetting agents such as, for example, cetyl alcohol and/or glycerol monostearate, absorbents such as kaolin and/or bentonite clay, and/or lubricants such as talc, calcium stearate, magnesium stearate, solid polyethylene glycols, sodium lauryl sulfate, and/or mixtures thereof. In the case of capsules, tablets and/or pills, the dosage form may comprise buffering agents.

Solid compositions may be employed as fillers in soft and hard-filled gelatin capsules, for example using such excipients as lactose and/or milk sugar as well as high molecular weight polyethylene glycols, etc. Solid dosage forms such as tablets, dragees, capsules, pills, and/or granules can be prepared with coatings and/or shells such as enteric coatings and/or other coatings well known in the pharmaceutical formulating art. They may optionally contain opacifying agents and/or can be of a composition that they release the active ingredient(s) only, and/or preferentially, in a certain part of the intestinal tract, optionally, in a delayed manner. Examples of embedding compositions that may be used include polymeric substances and/or waxes.

Solid compositions may be prepared in a micro-encapsulated form with one or more excipients as noted above. For example, tablets, dragees, capsules, pills, and/or granules may be prepared with coatings and/or shells such as enteric coatings, release controlling coatings and/or other coatings well known in the pharmaceutical formulating art. In such solid dosage forms the active compound may be admixed with at least one inert diluent such as sucrose, lactose and/or starch. Such dosage forms may comprise, as is normal practice, additional substances other than inert diluents, e.g., tableting lubricants and/or other tableting aids such a magnesium stearate and/or microcrystalline cellulose. In the case of capsules, tablets and/or pills, the dosage forms may comprise buffering agents. They may optionally contain opacifying agents and/or may be of a composition that they release the active ingredient(s) only, or preferentially, in a certain part of the intestinal tract, optionally, in a delayed manner. Examples of embedding compositions that can be used include polymeric substances and/or waxes.

Compositions for rectal and/or vaginal administration may be suppositories which may be prepared by mixing the compounds of this invention with suitable non-irritating excipients and/or carriers such as cocoa butter, polyethylene glycol and/or a suppository wax which are solid at ambient temperature but liquid at body temperature and therefore melt in the rectum and/or vaginal cavity and release the active compound.

Dosage forms for topical and/or transdermal administration of a compound of this invention may include ointments, pastes, creams, lotions, gels, powders, solutions, sprays, inhalants and/or patches. Generally, the active component is admixed under sterile conditions with a pharmaceutically acceptable carrier and/or any needed preservatives and/or buffers as may be required. Additionally, the present invention contemplates the use of transdermal patches, which often have the added advantage of providing controlled delivery of a compound to the body. Such dosage forms may be prepared, for example, by dissolving and/or dispensing the compound in the proper medium. Absorption enhancers may be used to increase the flux of the compound across the skin. Alternatively or additionally, the rate may be controlled by either providing a rate controlling membrane and/or by dispersing the compound in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions may be administered by devices which limit the effective penetration length of a needle into the skin, such as those described in PCT publication WO 99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes may be used in the classical mantoux method of intradermal administration.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

A pharmaceutical composition of the invention may be prepared, packaged, and/or sold in a formulation suitable for pulmonary administration via the buccal cavity. Such a formulation may comprise dry particles which comprise the active ingredient and which have a diameter in the range from about 0.5 to about 7 nanometers or from about 1 to about 6 nanometers. Such compositions are conveniently in the form of dry powders for administration using a device comprising a dry powder reservoir to which a stream of propellant may be directed to disperse the powder and/or using a self propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65.degree. F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions of the invention formulated for pulmonary delivery may provide the active ingredient in the form of droplets of a solution and/or suspension. Such formulations may be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

The formulations described herein as being useful for pulmonary delivery are useful for intranasal delivery of a pharmaceutical composition of the invention. Another formulation suitable for intranasal administration is a coarse powder comprising the active ingredient and having an average particle from about 0.2 to 500 micrometers. Such a formulation is administered in the manner in which snuff is taken, i.e. by rapid inhalation through the nasal passage from a container of the powder held close to the nares.

Formulations suitable for nasal administration may, for example, comprise from about as little as 0.1% (w/w) and as much as 100% (w/w) of the active ingredient, and may comprise one or more of the additional ingredients described herein. A pharmaceutical composition of the invention may be prepared, packaged, and/or sold in a formulation suitable for buccal administration. Such formulations may, for example, be in the form of tablets and/or lozenges made using conventional methods, and may, for example, 0.1 to 20% (w/w) active ingredient, the balance comprising an orally dissolvable and/or degradable composition and, optionally, one or more of the additional ingredients described herein. Alternately, formulations suitable for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition of the invention may be prepared, packaged, and/or sold in a formulation suitable for ophthalmic administration. Such formulations may, for example, be in the form of eye drops including, for example, a 0.1/1.0% (w/w) solution and/or suspension of the active ingredient in an aqueous or oily liquid carrier. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are contemplated as being within the scope of this invention.

The pharmaceutical compositions of the present invention may be administered by a variety of routes, including oral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, bucal, enteral, sublingual, and/or as an oral spray, nasal spray, and/or aerosol. In general the most appropriate route of administration will depend upon a variety of factors including the nature of the agent (e.g., its stability in the environment of the gastrointestinal tract), the condition of the patient (e.g., whether the patient is able to tolerate oral administration), etc. At present the oral and/or nasal spray and/or aerosol route is most commonly used to deliver therapeutic agents directly to the lungs and/or respiratory system. However, the invention encompasses the delivery of the inventive pharmaceutical composition by any appropriate route taking into consideration likely advances in the sciences of drug delivery.

General considerations in the formulation and/or manufacture of pharmaceutical agents may be found, for example, in *Remington: The Science and Practice of Pharmacy* $21^{st}$ ed., Lippincott Williams & Wilkins, 2005.

Administration

Typically, dosages of an agent of the invention which may be administered to an animal (e.g. a human) range in amount from 1 mg to about 100 g per kilogram of body weight of the subject. While the precise dosage administered will vary depending upon any number of factors, including but not limited to, the type of animal and/or type of disease state being treated, the age of the animal and/or the route of administration. In some embodiments, the dosage of the compound will vary from about 1 mg to about 10 g per kilogram of body weight of the animal. In some embodiments, the dosage will vary from about 10 mg to about 1 g per kilogram of body weight of the subject.

The compound may be administered to a subject as frequently as several times daily, and/or it may be administered less frequently, such as once a day, once a week, once every two weeks, once a month, and/or even less frequently, such as once every several months and/or even once a year or less. The frequency of the dose will be readily apparent to the skilled artisan and will depend upon any number of factors, such as, but not limited to, the type and/or severity of the disease being treated, the type and/or age of the subject, etc.

It will be understood, however, that the total daily usage of the compounds and/or pharmaceutical compositions of the present invention will be decided by the attending physician and/or veterinarian within the scope of sound medical judgment. The specific effective dose level for any particular patient and/or subject will depend upon a variety of factors including the disorder being treated and the severity of the disorder; the activity of the specific compound employed; the specific composition employed; the age, body weight, general health, sex and diet of the patient and/or subject; the time of administration, route of administration, and rate of excretion of the specific compound employed; the duration of the treatment; drugs used in combination and/or coincidental with the specific compound employed, and/or like factors well known in the medical arts.

The pharmaceutical compositions of the present invention may be administered either alone or in combination with one or more other therapeutic agents. By "in combination with," it is not intended to imply that the agents must be administered at the same time and/or formulated for delivery together, although these methods of delivery are within the scope of the invention. In general, each agent will be administered at a dose and/or on a time schedule determined for that agent. Additionally, the invention encompasses the delivery of the inventive pharmaceutical compositions in combination with agents that may improve their bioavailability, reduce and/or modify their metabolism, inhibit their excretion, and/or modify their distribution within the body. Although the pharmaceutical compositions of the present invention may be used for treatment of any subject (e.g., any animal) in need thereof, they are most preferably used in the treatment of humans.

The particular combination of therapies (therapeutics and/or procedures) to employ in a combination regimen will take into account compatibility of the desired therapeutics and/or procedures and/or the desired therapeutic effect to be achieved. It will be appreciated that the therapies employed may achieve a desired effect for the same disorder (for example, an inventive compound may be administered concurrently with another agent used to treat the same disorder), and/or they may achieve different effects (e.g., control of any adverse effects).

The pharmaceutical compositions of the present invention may be administered alone and/or in combination with other one or more agents that are used to treat the symptoms of a disease, condition, or disorder associated with PRPK, TPRKB, OSGEP, LAGE3 and its homologs, PRPK-TPRKB complex and/or KEOPS complex. In some embodiments, such agents may include thalidomide, lenalidomide, and/or pomalidomide. In some embodiment, such an agent may include bortezomib or dexamethasone. In some embodiments, such an agent may include any approved oncology drug.

In will further be appreciated that therapeutically active agents utilized in combination may be administered together in a single composition or administered separately in different compositions.

In some embodiments, inventive modulators of PRPK, TPRKB, OSGEP, LAGE3 and its homologs, PRPK-TPRKB complex and/or KEOPS complex may be administered in combination with one or more other modulators of a disease, condition, or disorder associated with PRPK, TPRKB, OSGEP, LAGE3 and its homologs, PRPK-TPRKB complex and/or KEOPS complex.

In general, it is expected that agents used in combination with be administered at levels that do not exceed the levels at which they are used individually. In some embodiments, the levels used in combination will be lower than those administered individually.

EXEMPLIFICATION

The representative Examples that follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that the contents of those cited references are incorporated herein by reference to help illustrate the state of the art.

The following Examples contain important additional information, exemplification and guidance that can be adapted to the practice of this invention in its various embodiments and the equivalents thereof. It will be appreciated, however, that these examples do not limit the invention. Variations of the invention, now known and/or further developed, are considered to fall within the scope of the present invention as described herein and as hereinafter claimed.

General Synthesis Information.

All reactions were carried out in oven or flame-dried glassware under an argon atmosphere employing standard techniques in handling air-sensitive materials. All commercially obtained reagents and solvents were used as supplied. Anhydrous THF, DMSO, pyridine and DCM were purchased with molecular sieves from ACROS chemicals. Reactions were magnetically stirred and monitored by thin layer chromatography (TLC) and by liquid chromatography-mass spectrometry (LC-MS) methods. TLC was done using 0.25-mm E Merck silica gel 60 $F_{254}$ pre-coated plates and vanillin stain, molybdate stain or UV for visualization. Flash chromatography was performed with silica gel 60 (particle size 0.032-0.063 mm) supplied by Sorbent Technologies. Agilent 1100 series LC-MSD single-quadrupole system with diode array detector and electrospray ion source was used for analytical runs as well as for the preparative reverse phase HPLC purifications. Agilent C-18 preparative column (21.2×100 mm, 5 μm) was used for all preparative HPLC purifications at a flow rate of 15 ml/min using mixtures of acetonitrile and water with 0.1% formic acid. Yields refer to chromatographically and spectroscopically pure compounds. $^1$H-NMR spectrum was recorded using an internal deuterium lock at ambient temperature on a Varian 400 MHz spectrometer. An internal reference of $\delta_H$ 7.26 was used for $CDCl_3$. NMR data are presented as follows: chemical shift (in ppm on the δ scale relative to $\delta_{TMS}$=0), integration, multiplicity (s=singlet, d=doublet, t=triplet, q=quartet, m=multiplet, dd=doublet of doublets, td=triplet of doublets, br=broad) and coupling constant (J/Hz). Resonances that are either partially or fully obscured are denoted obscured (obsc). Mass-spectra were obtained using Agilent 1100 series LC-MS.

General Cell Culture.

Cell lines Jurkat, NCI-H929, HS-Sultan, HEK-293FT and JeKo-1 were obtained from ATCC and maintained by vendor-specified media requirements at 37° C. in 5% $CO_2$ incubators. Cryopreserved PBMCs were obtained from Astarte Biologics and thawed and maintained by vendor-specified media requirements.

Example 1

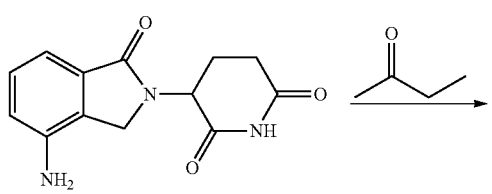

-continued

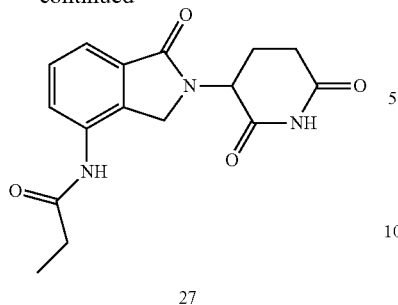

27

N-(2-(2,6-dioxopiperidin-3-yl)-1-oxoisoindolin-4-yl)propionamide (27)

A solution of lenalidomide (0.020 g, 0.077 mmol) in pyridine (0.8 mL) was cooled to 0° C. (ice bath). Propionyl chloride (0.009 mL, 0.100 mmol) was added dropwise and the reaction was allowed to warm to room temperature over 16 h. Volatiles were removed in vacuo and the crude residue was purified by flash chromatography on silica gel (0→5% MeOH in DCM as eluant) to afford desired product 27 (0.012 g, 50%) as an off-white powder. $^1$H NMR (400 MHz, DMSO) δ 11.04 (s, 1H), 9.79 (s, 1H), 7.80 (dd, J=6.6, 2.3 Hz, 1H), 7.64-7.29 (m, 2H), 5.14 (dd, J=13.2, 4.9 Hz, 2H), 4.35 (q, J=7.5 Hz, 2H), 3.00-2.79 (m, 1H), 2.60 (m, 1H), 2.35 (m, 1H), 2.05-1.92 (m, 1H), 1.08 (t, J=7.5 Hz, 3H). MS (ESI) m/z calcd for $C_{16}H_{18}N_3O_4$ [M+H]$^+$ 316.3, found: 316.8.

Example 2

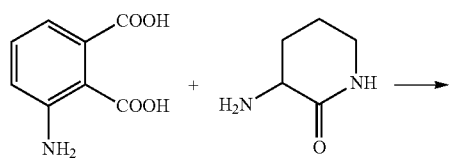

28

4-amino-2-(2-oxopiperidin-3-yl)isoindoline-1,3-dione (28)

To a solution of 3-aminophthalic acid (0.100 g, 0.552 mmol) in DMF (1.1 mL) was added 3-aminopiperidine-2-one (0.063 g, 0.552 mmol) and the reaction was stirred at 90° C. over 18 h. Volatiles were removed in vacuo and the dark-brown crude residue was purified by preparative reverse phase HPLC to give the desired product 28 (0.050 g, 35%) as an off-white powder. $^1$H NMR (400 MHz, DMSO) δ 7.83 (s, 1H), 7.43 (dd, J=8.3, 7.1 Hz, 1H), 7.07-6.87 (m, 2H), 6.47 (br s, 2H), 4.49 (dd, J=11.9, 6.3 Hz, 1H), 3.27-3.10 (m, 2H), 2.19 (dt, J=12.0, 7.7 Hz, 1H), 2.05-1.72 (m, 3H). MS (ESI) m/z calcd for $C_{13}H_{14}N_3O_3$ [M+H]$^+$ 260.3, found: 260.9.

Example 3

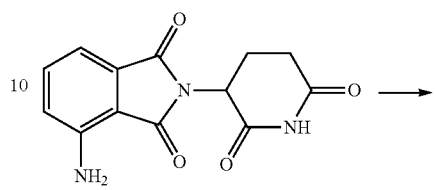

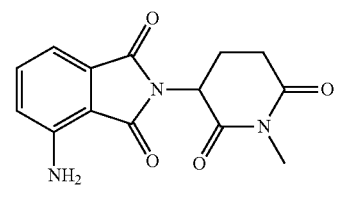

29

4-Amino-2-(1-methyl-2,6-dioxopiperidin-3-yl)isoindoline-1,3-dione (29)

To a solution of NaO$^t$Bu (0.074 g, 0.769 mmol) in DMSO (0.8 mL) was added a solution of pomalidomide (0.100 g, 0.366 mmol) in DMSO (0.5 mL plus 0.5 mL rinse) dropwise. The reaction was stirred for 10 min at room temperature followed by the addition of methyl iodide (0.025 mL, 0.403 mmol). After 18 h, glacial acetic acid (0.1 mL) was added to the reaction volatiles were removed in vacuo, and the crude dark-brown residue was purified by preparative reverse phase HPLC to afford 29 (0.02 g, 19%) as light yellow powder. $^1$H NMR (400 MHz, DMSO) δ 7.46 (dd, J=8.4, 7.0 Hz, 1H), 7.00 (dd, J=7.6, 5.6 Hz, 2H), 6.53 (br s, 2H), 5.11 (dd, J=13.2, 5.7 Hz, 1H), 2.97-2.83 (m, 1H), 2.76 (s, 1H), 2.57-2.51 (m, 1H), 2.06-1.91 (m, 1H). MS (ESI) m/z calcd for $C_{14}H_{14}N_3O_4$[M+H]$^+$ 288.3, found: 288.5.

Example 4

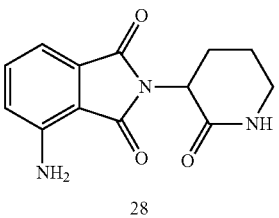

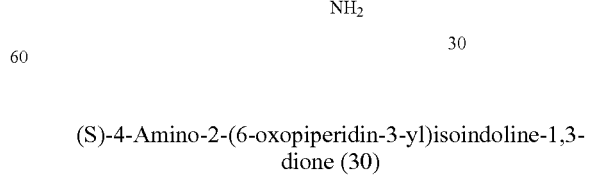

30

(S)-4-Amino-2-(6-oxopiperidin-3-yl)isoindoline-1,3-dione (30)

To a mixture of 3-amino phthalic acid hydrochloride (0.144 g, 0.664 mmol) and (S)-5-aminopiperidin-2-one hydrochloride (0.100 g, 0.664 mmol) in dry DMF (2.2 mL) was added triethylamine (0.933 mL, 6.64 mmol) and the reaction mixture was heated at 80° C. over 18 h. The crude mixture was quenched by the addition of a saturated aqueous NaHCO$_3$ solution (30 mL) and extracted using DCM (3×20 mL). Combined organic phases were dried over MgSO$_4$, filtered and concentrated. The crude residue was purified by preparative reverse phase HPLC to give the desired product 30 (0.08 g, 47%) as an off-white powder. $^1$H NMR (400 MHz, DMSO) δ 7.56 (s, 1H), 7.42 (dd, J=7.7, 7.7 Hz, 1H), 6.94 (m, 2H), 6.48 (br s, 2H), 4.32 (m, 1H), 3.60 (app t, J=11.3 Hz, 1H), 3.23-3.02 (m, 1H), 2.62-2.42 (obsc m, 1H), 2.42-2.21 (m, 2H), 1.86 (m, 1H). MS (ESI) m/z calcd for C$_{13}$H$_{14}$N$_3$O$_3$ [M+H]$^+$ 260.3, found: 260.7.

Example 5

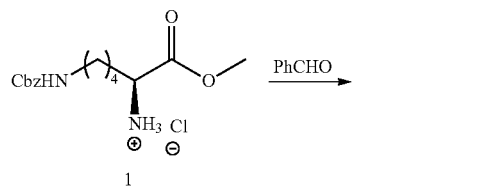

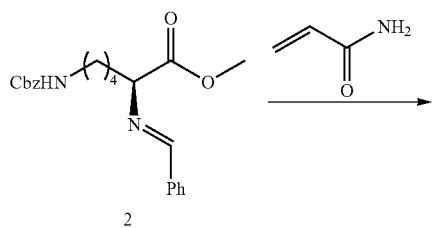

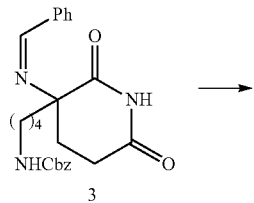

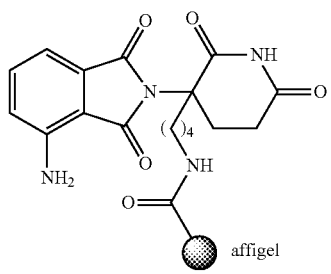

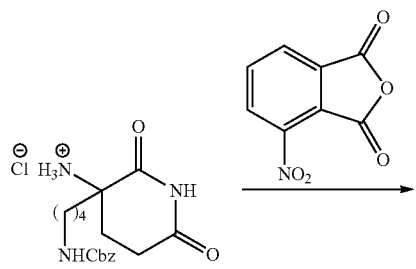

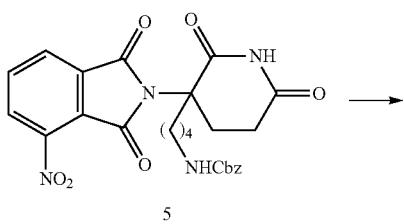

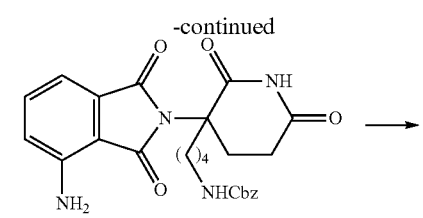

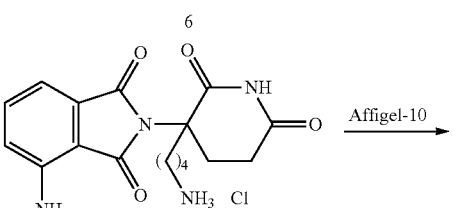

Synthesis of (S)-methyl 2-(benzylideneamino)-6-((((benzyloxy)carbonyl)amino)hexanoate (2)

To N$_\epsilon$-Z-L-lysine methyl ester hydrochloride (1 g, 3.022 mmol) and MgSO$_4$ (0.253 g, 2.1 mmol) in a round-bottom flask equipped with a stir bar was added DCM (4.3 mL). To the suspension were added triethylamine (0.5 mL, 3.63 mmol) followed by benzaldehyde (0.3 mL, 3.022 mmol) over 10 min. The reaction was stirred at room temperature for 20 h and filtered. The solids were subsequently washed with DCM. The organic phase was dried over MgSO$_4$, filtered, and concentrated to afford 2 as a colorless oil (1 g, 87%) which was used in the next step without further purification. R$_f$=0.68 (9:1 DCM:MeOH).

Synthesis of benzyl (4-(3-(benzylideneamino)-2,6-dioxopiperidin-3-yl)butyl)carbamate (3)

To a solution of 2 (4 g, 10.4 mmol) and acrylamide (1.11 g, 15.7 mmol) in THF (40 mL) was added portionwise potassium tert-butoxide (1.23 g, 11.0 mmol) over a period of 15 min at 0° C. After 3.5 h, the mixture was quenched with aqueous NH$_4$Cl and extracted into EtOAc. The organic layer was dried over MgSO$_4$, filtered, and concentrated to afford 3 (3.6 g, 82%) without further purification. R$_f$=0.33 (95:5 DCM:MeOH).

Synthesis of benzyl (4-(3-amino-2,6-dioxopiperidin-3-yl)butyl)carbamate hydrochloride (4)

To a solution of 3 (3.6 g, 8.54 mmol) in THF (21 mL) was added portionwise aqueous 4 M HCl at 0° C. The mixture was allowed to reach room temperature and stirred over 5 h. A white precipitated that formed during the reaction was filtered and washed with THF. Two recrystallizations afford 4 (2.88 g, 91.2%) as a white solid. $^1$H NMR (400 MHz, DMSO) ä 11.30 (s, 1H), 8.62 (br s, 3H), 7.46-7.15 (m, 5H), 4.97 (m, 2H), 3.59 (m, 2H), 2.98 (m, 2H), 2.76 (m, 1H), 2.58 (m, 1H), 2.24-1.97 (m, 2H), 1.85 (m, 2H), 1.74 (m, 1H), 1.21 (m, 1H).

Synthesis of benzyl (4-(3-(4-nitro-1,3-dioxoisoindolin-2-yl)-2,6-dioxopiperidin-3-yl)butyl)carbamate (5)

To a mixture of 4 (0.326 g, 0.881 mmol), 3-nitrophthalic anhydride (0.211 g, 1.093 mmol) and sodium acetate (0.097 g, 1.181 mmol) was added acetic acid (4.0 mL) and the resulting mixture was stirred overnight at 130° C. After 20 h, the mixture was carefully neutralized with sodium bicarbonate and extracted into DCM. The organic layer was dried over MgSO$_4$, filtered, and concentrated. Purification by flash chromatography (95:5 DCM:MeOH) afforded 5 (0.241 g, 54%) as a white solid.

Synthesis of benzyl (4-(3-(4-amino-1,3-dioxoisoindolin-2-yl)-2,6-dioxopiperidin-3-yl)butyl)carbamate (6)

To a suspension of 5 (0.24 g, 0.472 mmol) in ethanol (15 mL) was added Raney Nickel (W.R. Grace and Co. Raney® 4200, slurry, in H$_2$O) under argon. The mixture was subsequently saturated with hydrogen using a hydrogen balloon. After 1.5 h, the mixture was flushed with argon, filtered using EtOH and concentrated. Purification by flash chromatography (95:5 DCM:MeOH) afforded 6 (0.112 mg, 49%) as a bright yellow solid. R$_f$=0.38 (95:5 DCM:MeOH). $^1$H NMR (400 MHz, DMSO) δ 10.97 (s, 1H), 9.09 (s, 1H), 9.04 (s, 1H), 7.71-7.52 (m, 2H), 7.49-7.18 (m, 5H), 7.10 (m, 1H), 5.07-4.85 (m, 2H), 2.96 (m, 2H), 2.55 (m, 2H), 2.44 (m, 1H), 2.22 (m, 2H), 2.02 (m, 1H), 1.40 (m, 2H), 1.22 (m, 2H). MS (ESI) m/z calcd for C$_{25}$H$_{27}$N$_4$O$_6$ [M+H]$^+$ 479.5, found 479.9.

Synthesis of 4-amino-2-(3-(4-aminobutyl)-2,6-dioxopiperidin-3-yl)isoindoline-1,3-dione hydrochloride (7)

To a solution of 6 (0.111 g, 0.232 mmol) in 2% HCl in ethanol (60 mL) was added palladium on activated charcoal (0.025 g) under an atmosphere of argon. The mixture was subsequently saturated with hydrogen using a hydrogen balloon. After 4 h, the mixture was flushed with argon, filtered using ethanol and methanol. Preparative HPLC afforded 7 (0.055 g, 69%) as a bright yellow solid. $^1$H NMR (400 MHz, DMSO) δ 8.31 (s, 1H), 7.52-7.34 (m, 1H), 6.94 (m, 2H), 6.53 (br s, 2H), 2.74 (t, J=7.4 Hz, 2H), 2.65 (m, 1H), 2.63-2.56 (m, 1H), 2.54 (m, 1H), 2.44 (m, 1H), 2.31 (m, 1H), 2.21 (m, 1H), 2.02 (m, 1H), 1.52 (m, 1H), 1.48-1.38 (m, 1H), 1.26 (m, 2H). MS (ESI) m/z calcd for C$_{17}$H$_{21}$N$_4$O$_4$ [M+H]$^+$ 345.4, found 345.7.

Synthesis of 8 (Pomalidomide-Based Affinity Reagent)

About 2 mL of a suspension of affigel-10 (15 µmol/mL of gel, 50% slurry) in isopropanol was transferred to a conical tube and centrigured to a settled volume of 1.04 mL. The isopropanol was removed and the affigel-10 was washed with DMSO (3×5 mL). A DMSO (2.2 mL) solution of 7 (0.002 g, 0.00525 mmol) and triethylamine (0.007 mL, 0.0525 mmol) was subsequently added and the resulting mixture was sealed and tumbled on a rotator at room temperature. After 16 h, the conical tube was spun down and the DMSO supernatant was tested for the presence of 7 by LC-MS. 7 was not observed and therefore to the mixture was added triethylamine (0.015 mL, 0.105 mmol) and ethanolamine (0.006 mL, 0.10503 mmol) and the resulting mixture was tumbled on a rotator at room temperature. After 20 h, SS-0007896 was spun down, the solvent was removed, and the resin was washed with DMSO (3×5 mL) and isopropanol (3×5 mL) and stored in isopropanol at −20° C.

Example 6

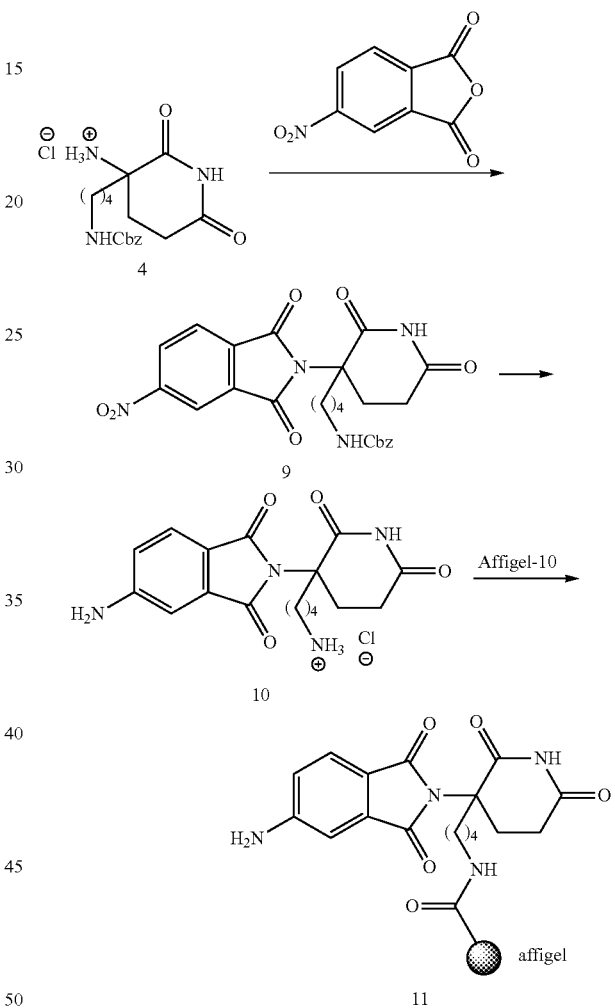

Synthesis of benzyl (4-(3-(5-nitro-1,3-dioxoisoindolin-2-yl)-2,6-dioxopiperidin-3-yl)butyl)carbamate (9)

To a suspension of 4 (0.4 g, 1.08 mmol), 4-nitrophthalic anhydride (0.259 g, 1.34 mmol), and sodium acetate (0.125 g, 1.45 mmol) was added acetic acid (4 mL) and the resulting mixture was stirred at 130° C. After 6 h, the mixture was quenched with sodium bicarbonate and extracted with DCM. The organic layer was dried over MgSO$_4$ and concentrated. Purification by flash chromatography (95:5 DCM:MeOH) afforded 9 (0.45 g, 87%). R$_f$=0.36 (95:5 DCM:MeOH). $^1$H NMR (400 MHz, CDCl$_3$) δ 8.62 (par obsc s, 1H), 8.60-8.51 (par obsc m, 1H), 8.16-7.86 (m, 2H), 7.44-7.27 (m, 5H), 5.07 (m, 2H), 3.23 (m, 3H), 2.93-2.49 (m, 3H), 2.46-2.23 (m, 1H), 2.14 (m, 1H), 1.79-1.47 (m, 3H), 1.45-1.17 (m, 2H), 1.00-0.75 (m, 1H). MS (ESI) m/z calcd for $C_{25}H_{25}N_4O_8$ [M+H]$^+$ 509.5, found 509.3.

Synthesis of 5-amino-2-(3-(4-aminobutyl)-2,6-dioxopiperidin-3-yl)isoindoline-1,3-dione hydrochloride (10)

To a suspension of 9 in ethanol (5 mL) was added Raney Nickel (W.R. Grace and Co. Raney® 4200, slurry, in H$_2$O) under argon. The mixture was subsequently saturated with hydrogen using a hydrogen balloon. After 12 h, the mixture was flushed with argon, filtered using MeOH and concentrated. Purification by preparative HPLC and subsequent evaporation from a 1M HCl solution afforded 10 (0.0063 mg, 15%). $^1$H NMR (400 MHz, DMSOi) δ 8.22 (s, 2H), 7.31 (dd, J=8.2, 2.1 Hz, 1H), 6.79 (d, J=2.1 Hz, 1H), 6.74 (dd, J=8.2, 2.1 Hz, 1H), 2.78 (t, J=7.5 Hz, 2H), 2.65-2.40 (par obsc m, 2H), 2.40-2.25 (m, 1H), 2.17-1.89 (m, 2H), 1.60-1.41 (m, 2H), 1.24 (d, J=44.1 Hz, 3H). MS (ESI) m/z calcd for $C_{17}H_{21}N_4O_4$ [M-Cl]$^+$ 345.4, found 345.6.

Synthesis of 11 (CMPD 31-Based Affinity Reagent)

About 5 mL of a suspension of affigel-10 (15 μmol/mL of gel, 50% slurry) in isopropanol was transferred to a conical tube and centrigured to a settled volume of 2.3 mL. The isopropanol was removed and the affigel-10 was washed with DMSO (3 times). A DMSO (5 mL) solution of 10 (0.0044 g, 0.0115 mmol) and triethylamine (0.016 mL, 0.115 mmol) was subsequently added and the resulting mixture was sealed and tumbled on a rotator at room temperature. After 16 h, the conical tube was spun down and the DMSO supernatant was tested for the presence of 10 by LC-MS. 10 was not observed and therefore to the mixture was added triethylamine (0.032 mL, 0.23 mmol) and ethanolamine (0.014 mL, 0.23 mmol) and the resulting mixture was tumbled on a rotator at room temperature. After 16 h, SS-0008803 was spun down, the solvent was removed, and the resin was washed with DMSO (3×5 mL) and isopropanol (3×5 mL) and stored in isopropanol at −20° C.

Example 7

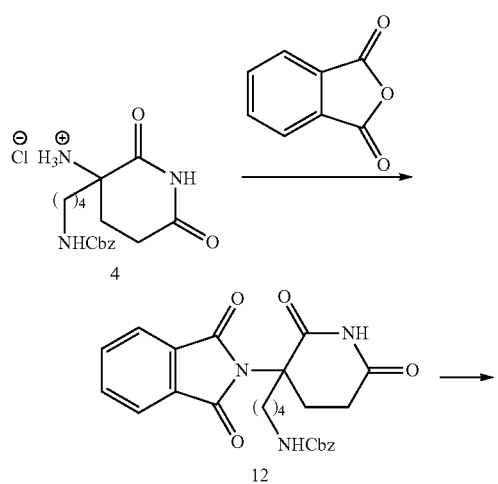

Synthesis of benzyl (4-(3-(1,3-dioxoisoindolin-2-yl)-2,6-dioxopiperidin-3-yl)butyl)carbamate (12)

To a suspension of 4 (0.12 g, 0.324 mmol), phthalic anhydride (0.060 g, 0.401 mmol), and sodium acetate (0.037 g, 0.434 mmol) was added acetic acid (1.5 mL) and the resulting mixture was stirred at 130° C. After 7 h, the mixture was quenched with sodium bicarbonate and extracted with DCM. The organic layer was dried over MgSO$_4$ and concentrated. Purification by preparative HPLC afforded 12. R$_f$=0.32 (95:5 DCM:MeOH). $^1$H NMR (400 MHz, CDCl$_3$) δ 8.05-7.64 (m, 5H), 7.44-7.27 (m, 4H), 5.16-5.00 (m, 2H), 4.90 (m, 1H), 3.34-3.09 (m, 3H), 2.92-2.77 (m, 1H), 2.77-2.45 (m, 3H), 2.36-2.18 (m, 1H), 2.17-1.99 (m, 1H), 1.38 (d, J=6.8 Hz, 2H). MS (ESI) m/z calcd for $C_{25}H_{26}N_3O_6$ [M+H]$^+$ 464.5, found 464.3.

Synthesis of 2-(3-(4-aminobutyl)-2,6-dioxopiperidin-3-yl)isoindoline-1,3-dione hydrochloride (13)

To a solution of 13 (0.024 g, 0.052 mmol) in 2% HCl in ethanol (60 mL) was added palladium on activated charcoal (0.005 g) under an atmosphere of argon. The mixture was subsequently saturated with hydrogen using a hydrogen balloon. After 2 h, the mixture was flushed with argon, filtered using ethanol and water. Preparative HPLC afforded 13 (0.018 g, 94%). $^1$H NMR (400 MHz, D$_2$O) δ 8.38 (s, 2H), 7.92-7.64 (m, 4H), 3.10-2.87 (m, 2H), 2.85-2.46 (m, 4H), 2.40-2.07 (m, 2H), 1.68 (dt, J=15.2, 7.7 Hz, 2H), 1.57-1.26 (m, 2H). MS (ESI) m/z calcd for $C_{17}H_{20}N_3O_4$ [M-Cl]$^+$ 330.4, found 330.6.

Synthesis of 14 (Thalidomide-Based Affinity Reagent)

About 8 mL of a suspension of affigel-10 (15 μmol/mL of gel, 50% slurry) in isopropanol was transferred to a conical tube and centrigured to a settled volume of 4.2 mL (3 equiv). The isopropanol was removed and the affigel-10 was washed with DMSO (3×5 mL). A DMSO (9.0 mL) solution of 13 (0.0078 g, 0.021 mmol) and triethylamine (0.0293 mL, 0.21 mmol) was subsequently added and the resulting mixture was sealed and tumbled on a rotator at room temperature. After 14 h, the conical tube was spun down and the DMSO supernatant

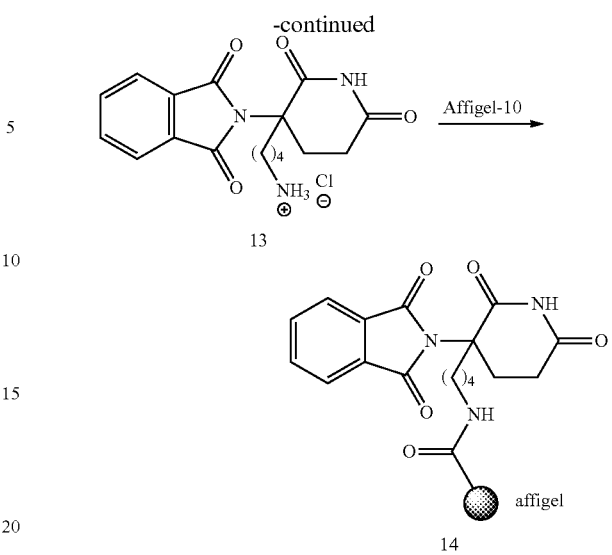

was tested for the presence of 14 by LC-MS. 14 was not observed and therefore to the mixture was added triethylamine (0.058 mL, 0.42 mmol) and ethanolamine (0.025 mL, 0.42 mmol) and the resulting mixture was tumbled on a rotator at room temperature. After 9 h, SS-0008820 was spun down, the solvent was removed, and the resin was washed with DMSO (3×5 mL) and isopropanol (3×5 mL) and stored in isopropanol at −20° C.

Example 8

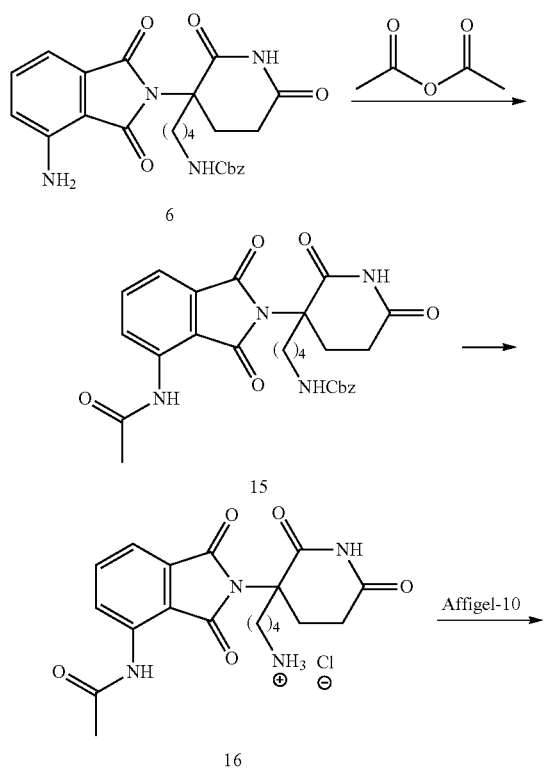

Synthesis of benzyl (4-(3-(4-acetamido-1,3-dioxoisoindolin-2-yl)-2,6-dioxopiperidin-3-yl)butyl)carbamate (15)

To a solution of acetic anhydride (0.098 mL, 1.04 mmol) in pyridine (1 mL) was added 6 (0.05 g, 0.104 mmol) and the mixture was stirred at 70° C. After 12 h, the mixture was quenched with 1% aqueous HCl and extracted with DCM. The organic layer was dried over MgSO$_4$ and concentrated. Preparatory thin layer chromatography (1:1 EtOAc:hexanes) afforded 15 (0.02 g, 37%) as an impure product that was used in the subsequent reaction. R$_f$=0.16 (1:1 EtOAc:hexanes).

Synthesis of N-(2-(3-(4-aminobutyl)-2,6-dioxopiperidin-3-yl)-1,3-dioxoisoindolin-4-yl)acetamide hydrochloride (16)

To a solution of 15 (0.02 g, 0.038 mmol) in 2% HCl in ethanol (2.0 mL) was added palladium on activated charcoal (0.004 g) under an atmosphere of argon. The mixture was subsequently saturated with hydrogen using a hydrogen balloon. After 2 h, the mixture was flushed with argon, filtered and concentrated. Preparative HPLC afforded 16 (0.002 g, 12%). $^1$H NMR (400 MHz, D$_2$O) δ 8.37 (s, 2H), 8.16 (d, J=8.5 Hz, 1H), 7.76 (dd, J=12.9, 5.5 Hz, 1H), 7.60 (d, J=7.4 Hz, 1H), 2.95 (t, J=7.6 Hz, 2H), 2.73 (m, 3H), 2.61-2.47 (m, 1H), 2.41-2.10 (m, 4H), 1.80-1.59 (m, 2H), 1.43 (d, J=39.6 Hz, 3H). MS (ESI) m/z calcd for C$_{19}$H$_{23}$N$_4$O$_5$ [M-Cl]$^+$387.4, found 387.7.

Synthesis of 17 (Acylated Affinity Reagent)

About 2 mL of a suspension of affigel-10 (15 μmol/mL of gel, 50% slurry) in isopropanol was transferred to a conical tube and centrigured to a settled volume of 0.95 mL (3 equiv). The isopropanol was removed and the affigel-10 was washed with DMSO (3×5 mL). A DMSO (2.0 mL) solution of 16 (0.002 g, 0.00473 mmol) and triethylamine (0.007 mL, 0.0473 mmol) was subsequently added and the resulting mixture was sealed and tumbled on a rotator at room temperature. After 20 h, the conical tube was spun down and the DMSO supernatant was tested for the presence of 16 by LC-MS. 16 was not observed and therefore to the mixture was added triethylamine (0.013 mL, 0.0946 mmol) and ethanolamine (0.006 mL, 0.0946 mmol) and the resulting mixture was tumbled on a rotator at room temperature. After 12 h, SS-0008821 was spun down, the solvent was removed, and the resin was washed with DMSO (3×5 mL) and isopropanol (3×5 mL) and stored in isopropanol at −20° C.

Example 9

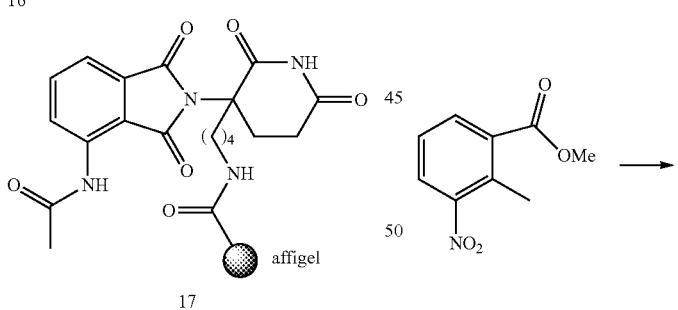

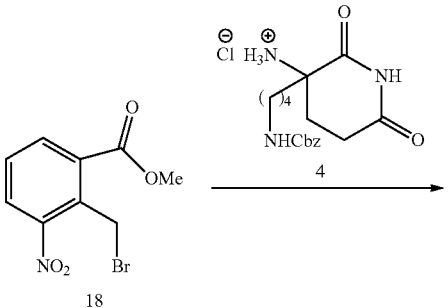

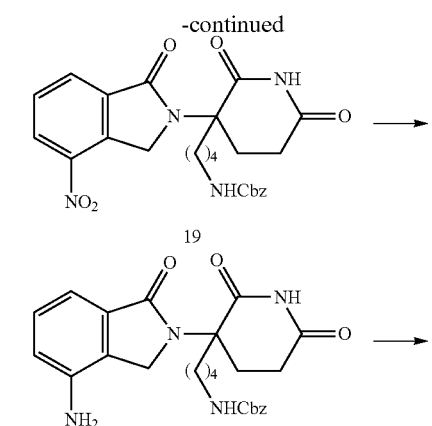

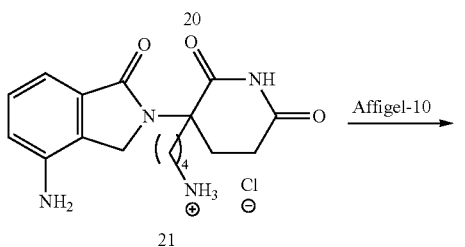

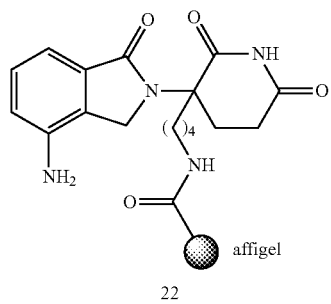

Synthesis of methyl 2-(bromomethyl)-3-nitrobenzoate (18)

To a solution of methyl 2-methyl-3-nitrobenzoate (5 g, 25.6 mmol) in dry DCM (20 mL) were added NBS (4.56 g, 25.6 mmol) and AIBN (0.421 g, 2.56 mmol) and the mixture was stirred at 60° C. After 20 h, additional AIBN (0.42 g) was added and the mixture continued to be stirred at 60° C. After 72 h, the mixture was filtered and concentrated. Purification by flash chromatography (100% hexanes to 10% EtOAC/hexanes) afforded 18 (5.2 g, 74%) as a light yellow solid. $R_f$=0.3 (9:1 hexanes:ethyl acetate). $^1$H NMR (400 MHz, CDCl$_3$) δ 8.11 (dd, J=7.9, 1.4 Hz, 1H), 8.03-7.91 (m, 1H), 7.54 (dd, J=8.0 Hz, 8.0 Hz, 1H), 5.24-5.03 (s, 2H), 4.08-3.88 (s, 3H). MS (ESI) m/z calcd for C$_9$H$_9$BrNO$_4$ [M+H]$^+$ 275.1, found 275.5.

Synthesis of benzyl (4-(3-(4-nitro-1-oxoisoindolin-2-yl)-2,6-dioxopiperidin-3-yl)butyl)carbamate (19)

To a stirred mixture of 18 (0.25 g, 0.912 mmol) and 4 (0.337 g, 0.912 mmol) in DMF (3.0 mL) was added triethylamine (0.320 mL, 2.28 mmol) and resulting mixture was stirred at 114° C. to 130° C. After 18 h, the mixture was cooled and concentrated. Purification by flash chromatography (95:5 DCM:MeOH) afforded 19 (0.27 g, 60%) as a light brown fluffy solid. $^1$H NMR (400 MHz, DMSO) δ 10.99 (s, 1H), 8.45 (d, J=8.2 Hz, 1H), 8.08 (d, J=7.6 Hz, 1H), 7.94 (s, 1H), 7.80 (dd, J=7.8 Hz, 7.8 Hz, 1H), 7.44-7.19 (m, 5H), 5.17-4.84 (m, 4H), 3.05-2.96 (m, 2H), 2.69-2.52 (m, 3H), 2.20-1.94 (m, 3H), 1.35 (m, 4H). MS (ESI) m/z calcd for C$_{25}$H$_{27}$N$_4$O$_7$ [M+H]$^+$ 495.5, found 495.9.

Synthesis of benzyl (4-(3-(4-amino-1-oxoisoindolin-2-yl)-2,6-dioxopiperidin-3-yl)butyl)carbamate (20)

To a solution of 19 (0.26 g, 0.526 mmol) in EtOH:DMF (2:1, 6 mL) was added Raney Nickel (W.R. Grace and Co. Raney® 4200, slurry, in H$_2$O) under argon. The mixture was subsequently saturated with hydrogen using a hydrogen balloon. After 16 h, the mixture was filtered to afford a mixture of 20 and 21, as judged by LC-MS. The mixture was used in a subsequent reaction without further purification.

Synthesis of 3-(4-amino-1-oxoisoindolin-2-yl)-3-(4-aminobutyl)piperidine-2,6-dione hydrochloride (21)

To a solution of impure 20 (0.1 g, 0.215 mmol) in EtOH/DMF (2:1, 3.5 mL) was added palladium on activated charcoal (20% by weight) under argon. The mixture was subsequently saturated with hydrogen using a hydrogen balloon. After 5 h, the mixture was flushed with argon, filtered and concentrated. Preparatory HPLC afforded 21 (0.012 mg, 16%). $^1$H NMR (400 MHz, DMSO) δ 8.43 (s, 1H), 7.14 (dd, J=7.6 Hz, 7.5 Hz, 1H), 6.87-6.65 (m, 2H), 5.56 (s, 2H), 4.35 ((ABq, J$_{AB}$=17.6 Hz, Δν$_{AB}$=15.4 Hz, 2H), 2.82-2.71 (m, 2H), 2.67-2.56 (m, 2H), 2.56-2.40 (m, 2H), 2.09-1.93 (m, 2H), 1.64-1.53 (m, 2H), 1.52-1.28 (m, 2H). MS (ESI) m/z calcd for C$_{17}$H$_{23}$N$_4$O$_3$ [M+H]$^+$ 331.4, found 331.7.

Synthesis of 22 (Lenalidomide-Based Affinity Reagent)

About 9 mL of a suspension of affigel-10 (15 μmol/mL of gel, 50% slurry) in isopropanol was transferred to a conical tube and centrigured to a settled volume of 6.65 mL (3 equiv). The isopropanol was removed and the affigel-10 was washed with DMSO (3×5 mL). A DMSO (10.0 mL) solution of 21 (0.011 g, 0.033 mmol) and triethylamine (0.047 mL, 0.333 mmol) was subsequently added and the resulting mixture was sealed and tumbled on a rotator at room temperature. After 20 h, the conical tube was spun down and the DMSO supernatant was tested for the presence of 21 by LC-MS. 21 was not observed and therefore to the mixture was added triethylamine (0.093 mL, 0.666 mmol) and ethanolamine (0.040 mL, 0.666 mmol) and the resulting mixture was tumbled on a rotator at room temperature. After 16 h, SS-0017471 was spun down, the solvent was removed, and the resin was washed with DMSO (3×5 mL) and isopropanol (3×5 mL) and stored in isopropanol at −20° C.

Example 10

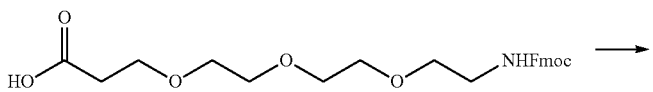

-continued
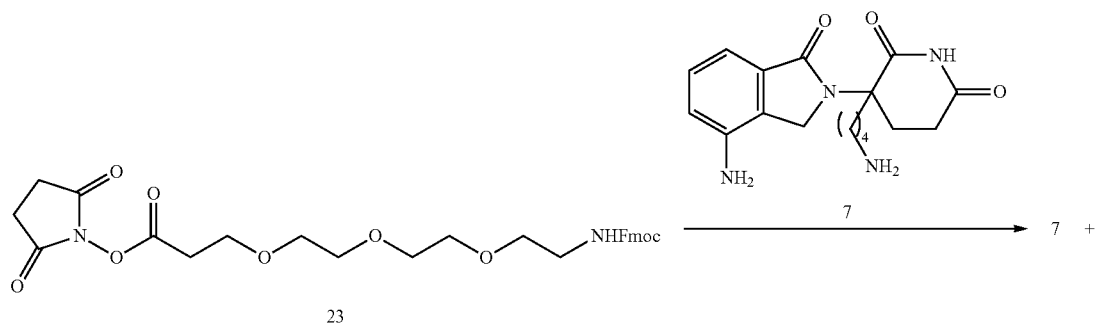
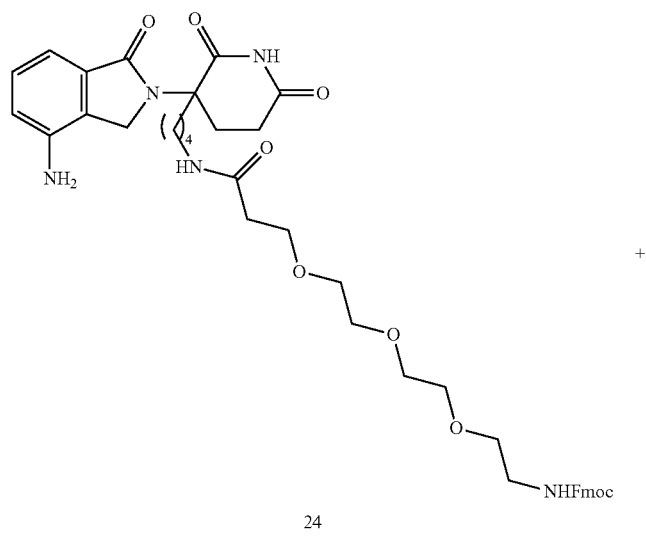
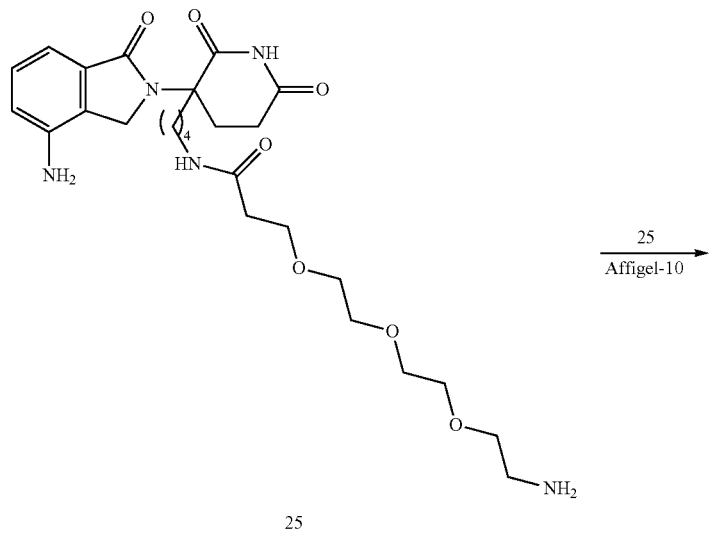

-continued

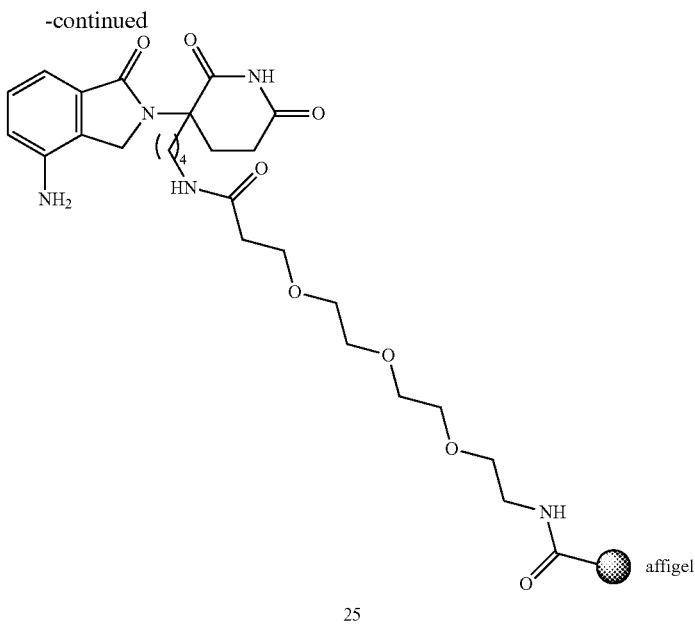

25

Synthesis of 2,5-dioxopyrrolidin-1-yl 1-(9H-fluoren-9-yl)-3-oxo-2,7,10,13-tetraoxa-4-azahexadecan-16-oate (23)

To a solution of Fmoc-12-amino-4,7,10-trioxadodecanoic acid (0.2 g, 0.451 mmol) in dry THF (11 mL) were added N-hydroxysuccinimide (0.060 g, 0.519 mmol) and N,N'-Dicyclohexylcarbodiimide (0.107 g, 0.5191 mmol) under argon at 0° C. The reaction mixture was then allowed to reach room temperature. After 20 h, the mixture was concentrated and purified by flash chromatography (95:5 DCM:MeOH) to afford 23 (0.116 g, 48%) with some impurities. 23 was not purified further and was used in the subsequent reaction step. $R_f$=0.47 (95:5 DCM:MeOH).

Synthesis of N-(4-(3-(4-amino-1,3-dioxoisoindolin-2-yl)-2,6-dioxopiperidin-3-yl)butyl)-3-(2-(2-(2-aminoethoxy)ethoxy)ethoxy)propanamide (25)

To a solution of 23 (0.012 g, 0.022 mmol) in DMSO (2 mL) were added 7 (0.011 g, 0.0289 mmol) and triethylamine (0.01 mL, 0.071 mmol) under an atmosphere of argon, and the mixture was stirred at room temperature. After 16 h, the crude mixture was directly purified by preparative HPLC to afford 25 (0.005 g, 42%), 24 (0.0014 g, 8.2%) and unreacted 7 (0.0037 g, 48%). $^1$H NMR (400 MHz, DMSO) δ 8.39 (s, 2H), 7.86 (s, 1H), 7.49-7.37 (m, 1H), 7.04-6.82 (m, 2H), 6.53 (s, 2H), 3.59-3.36 (m, 11H), 3.03-2.93 (m, 2H), 2.84-2.76 (m, 2H), 2.33-2.16 (m, 5H), 2.05-1.96 (m, 2H), 1.44-1.31 (m, 3H), 1.25-1.16 (m, 3H). MS (ESI) m/z calcd for $C_{26}H_{38}N_5O_8$ [M+H]$^+$ 548.6, found 548.5.

Synthesis of 26 (Loading of Compound onto Affigel)

About 1 mL of a suspension of affigel-10 (15 μmol/mL of gel, 50% slurry) in isopropanol was transferred to a conical tube and centrigured to a settled volume of 0.73 mL (3 equiv). The isopropanol was removed and the affigel-10 was washed with DMSO (3×5 mL). A DMSO (10.0 mL) solution of 25 (0.002 g, 0.0036523 mmol) and triethylamine (0.005 mL, 0.037 mmol) was subsequently added and the resulting mixture was sealed and tumbled on a rotator at room temperature. After 16 h, the conical tube was spun down and the DMSO supernatant was tested for the presence of 25 by LC-MS. 25 was not observed and therefore to the mixture was added triethylamine (0.0102 mL, 0.073 mmol) and ethanolamine (0.004 mL, 0.073 mmol) and the resulting mixture was tumbled on a rotator at room temperature. After 20 h, SS-0017436 was spun down, the solvent was removed, and the resin was washed with DMSO (3×5 mL) and isopropanol (3×5 mL) and stored in isopropanol at −20° C.

Example 11

Figure 8:
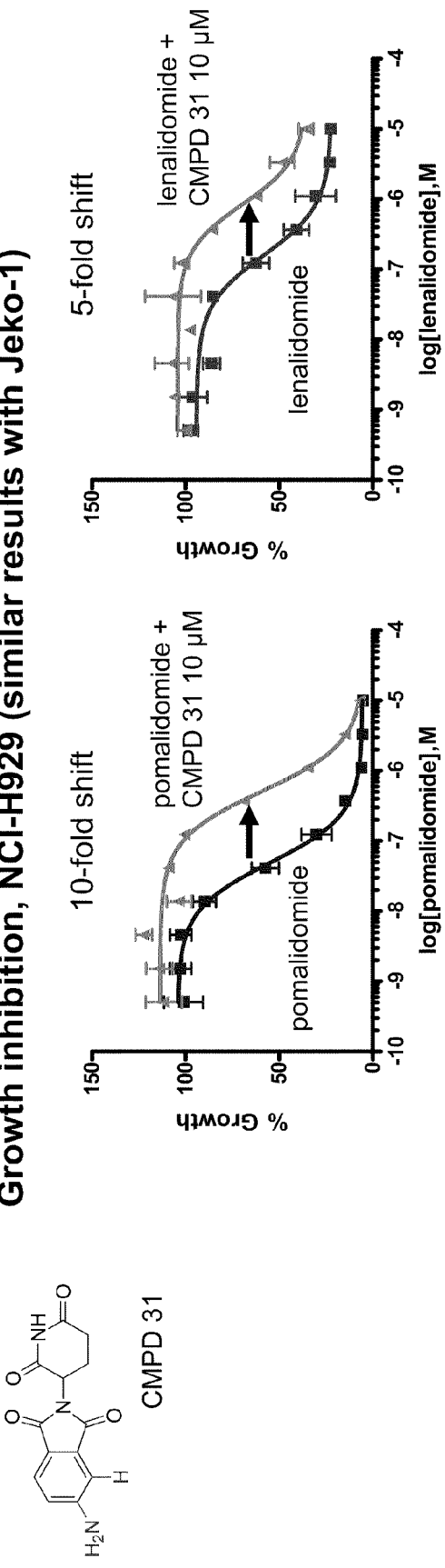
FIG. 8. Results showing that CMPD 31 suppresses the activity of lenalidomide and pomalidomide in induction of IL-2 production and inhibition of B cell growth.
Figure 8:
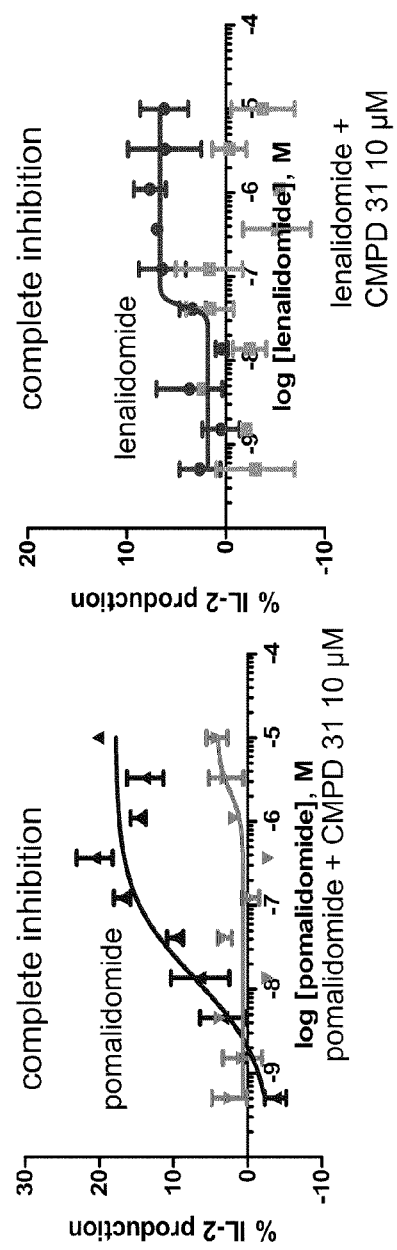

IL-2 Production Assay (see FIGS. 1 and 8)

This protocol describes the technique to detect the amount of IL-2 produced by Jurkat and PBMCs in 96-well format. This assay was used to calculate IL-2 production $EC_{50}$ values of lenalidomide, pomalidomide, all derivatives and inhibition with CMPD 31.

Cell Plating and Compound Addition

Logarithmically growing Jurkat cells from ATCC (clone E6-1) or frozen and thawed human PBMCs from Astarte (Peripheral Blood Mononuclear Cells, normal Donor 41) were resuspended at 1×10$^6$ cells/mL in RPMI-1640 medium containing 10% FBS and 1% antibiotic/antimycotic solution. Cells were plated into each well of a 96-well anti-CD3 plate (Becton Dickinson catalogue number #354725) at 1×10$^5$ cells/100 μl per well. Controls were added to columns 1 and 12 where 0.1% DMSO in eight replicate wells represented the negative or 0% IL-2 production control and 0.1 μg/ml anti-CD28 antibody (Becton Dickinson catalog #555725) in eight replicate wells represented the positive or 100% IL-2 production control.

Compounds were serially diluted 3-fold in 100% DMSO into duplicate 10-point dose curves using a Biomek FX liquid handler in columns 2 through 11 of a 96-well U-bottom plate. Starting concentration of compounds was 10 mM. Daughter plates containing 2 μL of the compound dose curves were stamped and stored at −80 C.

Compound daughter plates were resuspended in 200 μL of RPMI-1640 medium as a 10× stock and then 20 μL of the 10× stock was added to each anti-CD3 antibody assay plate well with a final volume of 200 μl by the addition of 80 μl of complete media. For the CMPD 31 IL-2 inhibition assays, a 10× stock (100 μM) of CMPD 31 in RPMI-1640 medium was prepared and diluted into each assay well at all concentrations of lenalidomide and pomalidomide at a final concentration of 10 μM. Assay plates were incubated for 18 hours at 37° C. in 5% $CO_2$. The amount of IL-2 produced was determined by an ELISA assay and was performed in one of two ways as per manufacturer instructions; by a standard ELISA (Enzyme-Linked Immunosorbent Assay) protocol method (Becton Dickinson) or an AlphaLISA protocol (Perkin Elmer).

IL-2 Detection

Briefly, for the standard ELISA, 100 μl of supernatant from the compound-treated assay plate was added to each IL-2 detection ELISA plate well with 50 μl of diluent and the plate was incubated for 2 hours at room temperature. Each plate was washed five times with 100 μl of wash buffer by flicking the plate and patting it dry. 100 μl of prepared working detector solution was added to each well. The ELISA plate was incubated for 1 hour at room temperature followed by seven washes, as above, and then followed by addition of 100 μl of TMB one-step substrate Reagent to each well. The ELISA plate was then incubated for 30 minutes at room temperature and then 50 μl of stop solution was added to each well. Colorimetric detection was performed at 450 nm within 10 minutes of adding stop solution on a Victor$^3$ plate reader.

Briefly, for the AlphaLISA protocol, 5 μl of supernatant from the compound-treated assay plate was added to a 96-well half area detection plate and 20 μl of a 2.5×MIX was subsequently added to the wells. AlphaLISA anti-IL-2 acceptor beads were added to the wells at a final concentration of 10 μl/mL and biotinylated anti-IL-2 antibody was added to a final concentration of 1 nM. The detection plate was incubated for 60 minutes at 23° C. and 25 μl of 2×SA-donor beads at 40 Ag/mL final concentration was added. The detection plate was incubated for 30 minutes at 23° C. in the dark. Detection was carried out using the Biotek Syn4-alpha plate reader with excitation at 680 nm and emission at 570 nm.

Data was normalized to within-plate controls; 0.1% DMSO was used to represent 0% IL-2 production and 0.1 μg/ml anti-CD28 antibody was used to represent 100% IL-2 production. Dose curve analysis for $EC_{50}$ values was performed using basic nonlinear regression with a sigmoidal dose response (variable slope) in ActivityBase version 7.0 software (IDBS) or GraphPad Prism 5 software.

Example 12

Growth Inhibition Assays (see FIGS. 1 and 8)

This protocol describes the technique to perform growth inhibition assays in 96-well format. This assay was used to calculate growth inhibition $IC_{50}$ values of lenalidomide, pomalidomide, all derivatives and inhibition with CMPD31.

Cell Culture and Cell Plating

Cell lines Jurkat, NCI-H929, and JeKo-1 were obtained from ATCC and were maintained by vendor-specified media requirements. Cells were plated in 96-well plates at 3,750 cells per well (Jeko-1, HS-Sultan) or 5,000 cell per well (NCI-H929) in 90 μL of assay growth medium (RPMI-1640, 10% FBS, 1% pen-strep). Cells in plates were allowed to incubate at room temperature for one hour and then transferred to an incubator set at 37° C. and 5% $CO_2$ humidified air overnight.

Compound Plate Creation

Compounds were serially diluted 3-fold in 100% DMSO into duplicate 10-point dose curves using a Biomek FX liquid handler in columns 2 through 11 of a 96-well U-bottom plate. Starting concentrations of compounds was 10 mM. Daughter plates containing 2 μL of the compound dose curves were stamped and stored at −80 C. Control plates were made by stamping 2 μL of 100% DMSO into columns one and 12 rows A, B, E and F and 2 μL of 10 mM Doxorubicin in rows C, D, G and H. DMSO and Doxorubicin were used as plating controls, 100% and 0% growth respectively.

Compound Addition, Assay Detection and Analysis

Compound and control daughter plates were diluted 100-fold in 200 μl of assay growth medium and then finally diluted 10-fold more into the 96-well cell plates; a final dilution of 1000-fold in 0.1% DMSO for all wells. For the CMPD 31 growth inhibition assays, a 10× stock (100 μM) of CMPD 31 in RPMI-1640 medium was prepared and diluted into each assay well at all concentrations of lenalidomide and pomalidomide at a final concentration of 10 μM. Compound-treated plates were incubated for 120 hours at 37° C. in 5% $CO_2$ and then 10 μL of Cell Titer Blue (Promega Corporation) was added to each well. Plates were incubated for 2 hours at 37° C. in 5% $CO_2$ and then plates were read on a Perkin Elmer Victor$^3$ V plate reader with excitation at 560 nm and emission at 590 nm. Data was normalized to within-plate controls; 0.1% DMSO was used to represent 100% growth and 10 μM Doxorubicin was used to represent 0% growth. Dose curve analysis for $IC_{50}$ values was performed using basic nonlinear regression with a sigmoidal dose response (variable slope) in ActivityBase version 7.0 software (IDBS).

Example 13

Target Discovery by Standard Small Molecule Affinity Chromatography (see FIGS. 2-5 and 7)

Cell lysates were prepared from 2×10$^8$ Jeko-1, Jurkat, or HS-Sultan cells or 5×10$^7$ HeLa S3 cells per pulldown sample by lysis in 2 mL Buffer B (50 mM HEPES pH 7.5, 5% glycerol, 1.5 mM $MgCl_2$, 150 mM NaCl, 1 mM $Na_3VO_4$, 25 mM NaF, 0.4% Nonidet P-40, 1 mM DTT, and 1 Complete Mini EDTA-free protease inhibitor tablet per 10-25 mL Buffer B). Lysates were incubated on ice for 30 mM, followed by 2× freeze-thaw using liquid $N_2$ and 37° C. water bath in polypropylene tubes. Samples were centrifuged at 1800 rpm for 5 mM at 4° C. Supernatants were ultracentrifuged at 55,000 rpm for 1 hr at 4° C. Supernatants were collected and pre-cleared with 10 μL control affigel reagent (affigel-ethanolamine or affigel-PEG linker) by incubation on a rotator for 30 mM at 4° C. Pre-cleared lysates were transferred to Mobicol 1 mL columns with 90 μm pore size frit on ice and centrifuged at 0.1 rcf for 10 sec to separate affigel beads from lysates. Incubations with pre-cleared lysates and excess pomalidomide were performed at a 20-fold excess competitor concentration (500 μM final concentration) on a rotator for 30 mM at 4° C. Subsequently, 10 μL control or pomalidomide-based affigel reagents were added to each sample and pulldowns were performed for 1 hr at 4° C. Lysates and affigel reagents were transferred to Mobicol 1 mL columns with 90 μm pore size frit and affigel beads were washed 3× with 800 μL Buffer B and 2× with 800 μL Buffer A (Buffer B not including 0.4% Nonidet P-40). Columns were centrifuged for 30 sec at 0.1 rcf to remove any remaining wash buffer and then closed with lower plug. Columns were placed in 1.5 mL Low-binding Eppendorf tubes and heated at 50° C. for 30 mM in 40 uL 2×SDS sample buffer with 10 mM DTT to elute bound proteins from affigel reagents. Columns were then opened and eluents were collected in the low-binding Eppendorf tubes by 15 sec centrifugation at 1600 rpm. Samples were applied and resolved on 4-12% SDS-PAGE gels followed by silver staining (SilverQuest Kit, Invitrogen, Carlsbad, Calif.). Bands which were competed by excess actimid competitor but not by DMSO were excised and identified by LC/MS/MS analysis at the Beth Israel Deaconess Medical Center Mass Spectrometry Core Facility (Boston, Mass.).

Example 14

Figure 3:
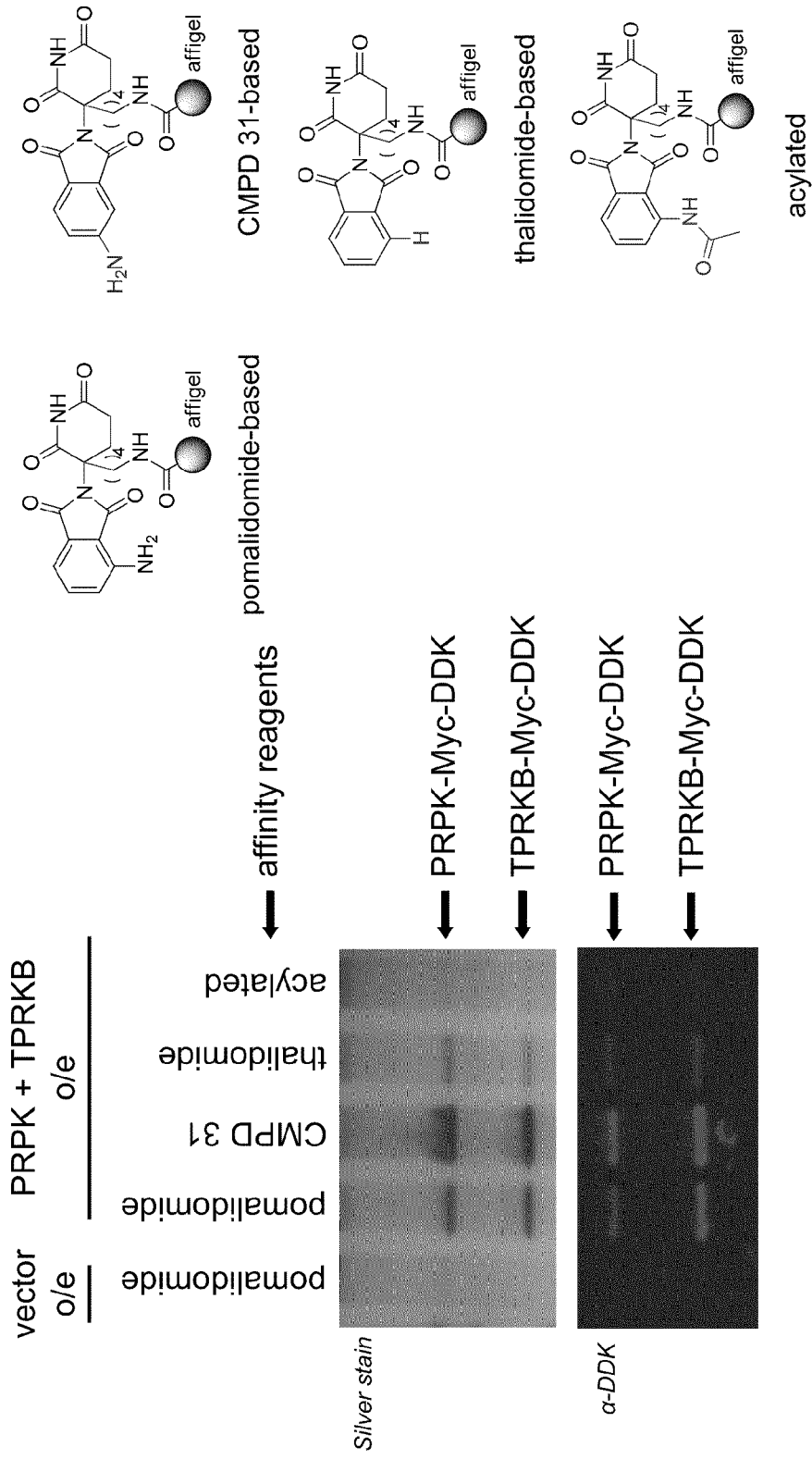
FIG. 3. PRPK and TPRKB captured with three affinity reagents derived from compounds of formula I. An acylated version did not capture PRPK or TPRKB. C-terminal tagged proteins were captured like endogenous proteins.
Figure 4:
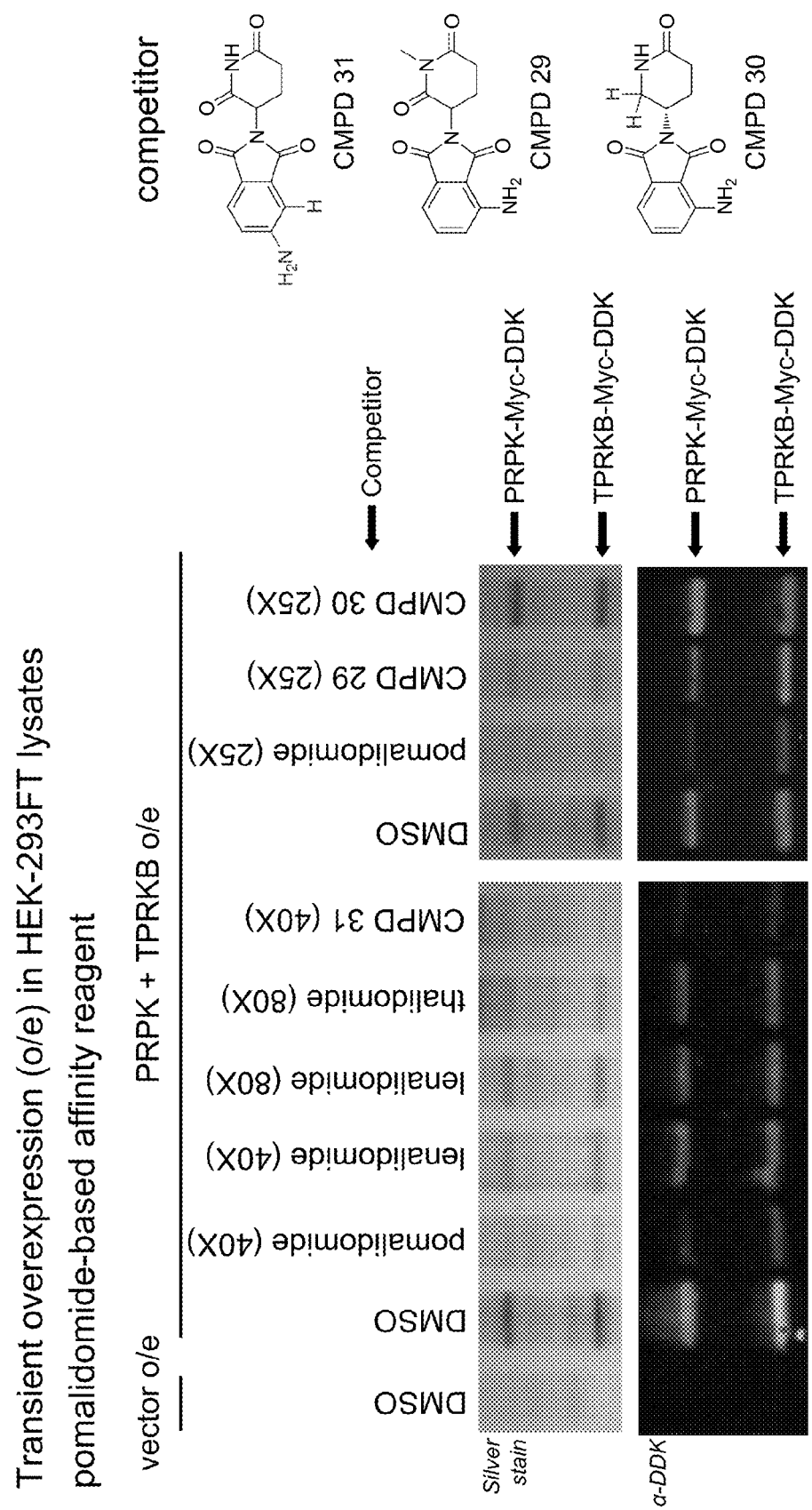
FIG. 4. Results showing that pomalidomide, lenalidomide, thalidomide, CMPD 31, and CMPD 29 compete for PRPK/TPRKB target binding to the pomalidomide-based affinity reagent, yet CMPD 30 does not.
Figure 5:
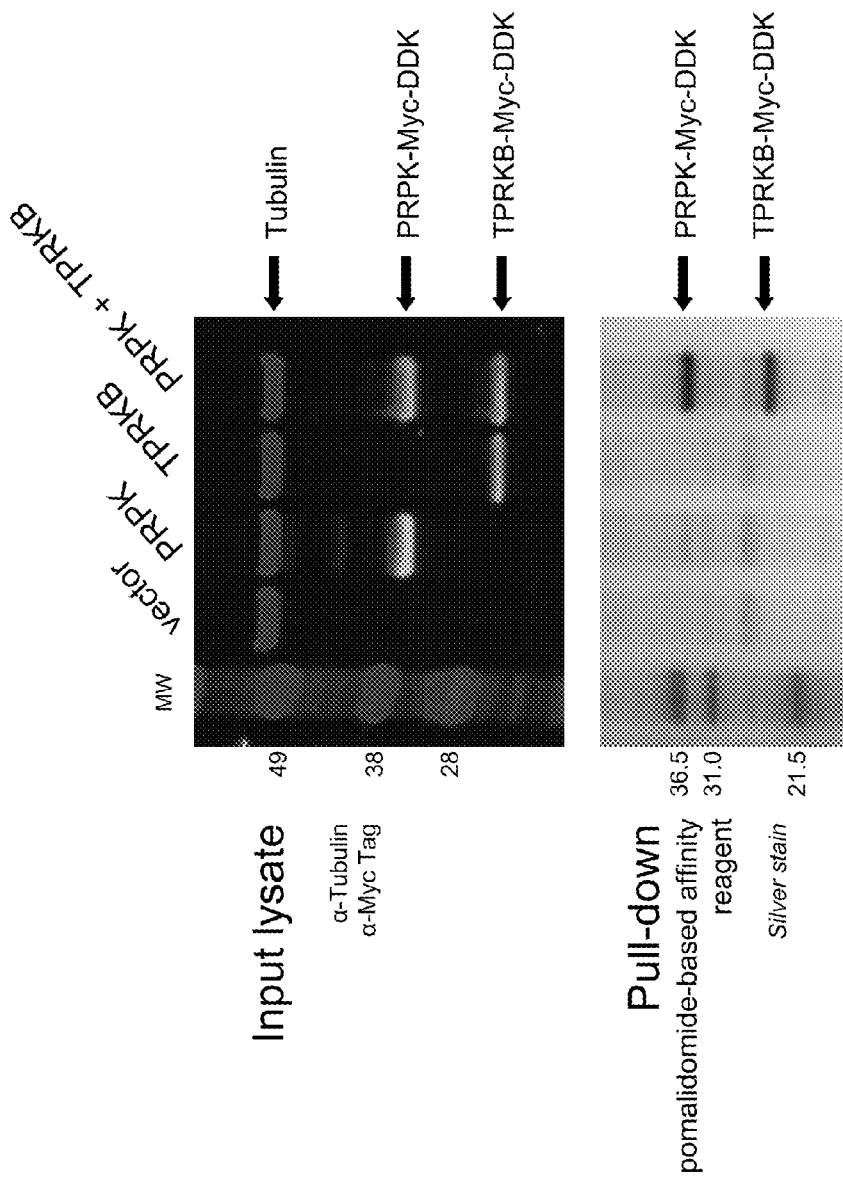
FIG. 5. Results showing that the pomalidomide-based affinity reagent captures PRPK and TPRKB, but not PRPK or TPRKB alone, supporting the PRPK/TPRKB complex as the target.

Affigel Binding to Overexpressed PRPK and TPRKB (see FIGS. 3-5)

C-term Myc-DDK tagged PRPK and C-term Myc-DDK tagged TPRKB proteins were transiently overexpressed from cDNAs (obtained from Origene, Rockville, Md.) in HEK-293FT cells using FuGENE-6 transfection reagent according to the manufacturer's protocol (Roche, Indianapolis, Ind.). One day prior to transfection, $2.5 \times 10^6$ HEK-293FT cells were plated per p100 dish. Cells were lysed 48 hr post-transfection in 1-2 mL Buffer B per p100 dish per sample. Pulldowns were performed as described above for standard small molecule affinity chromatography with active (pomalidomide-based) or inactive (CMPD 31-based, thalidomide-based, or acylated) affinity reagents. The amount of PRPK and TPRKB captured by each affinity reagent was determined by silver stain and anti-DDK (anti-DDK monoclonal antibody, Origene) Western blot. Competition experiments were also performed using a variety of compounds and derivatives (pomalidomide, lenalidomide, thalidomide, CMPD 31, CMPD 30, CMPD 29).

Example 15

Figure 6:
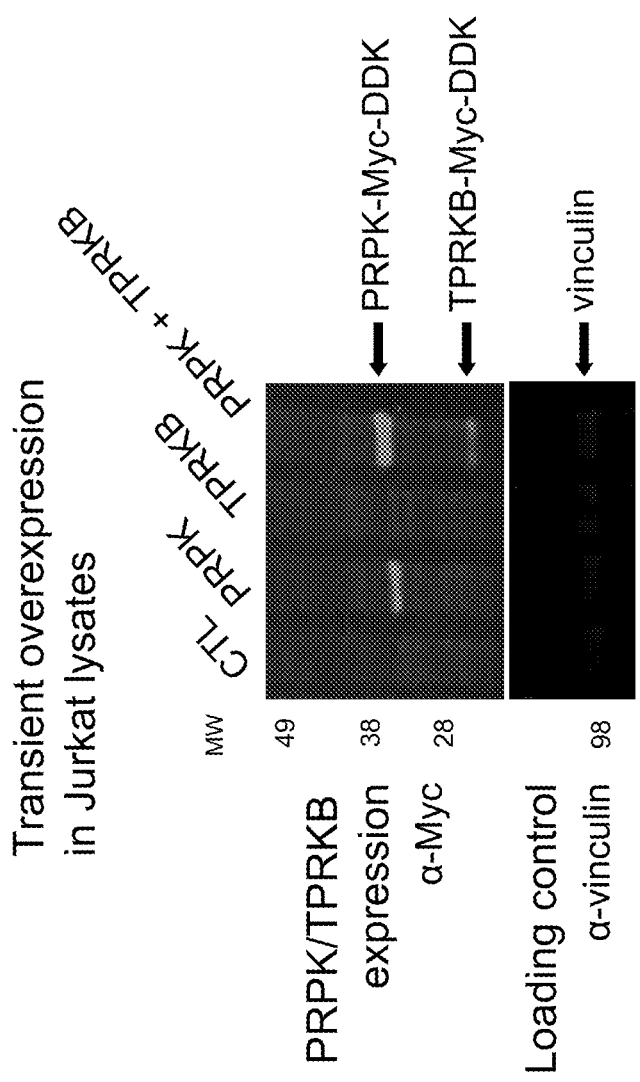
FIG. 6. Results showing that PRPK and TPRKB interact in Jurkat cells, supporting PRPK/TPRKB complex formation in a cellular context. The PRPK/TPRKB complex stabilizes TPRKB in Jurkat cells.

Overexpression of PRPK and TPRKB in Jurkat Cells (see FIG. 6)

C-term Myc-DDK tagged PRPK and C-term Myc-DDK tagged TPRKB proteins were transiently overexpressed in Jurkat cells using FuGENE-6 transfection reagent (Roche). PRPK and TPRKB cDNAs were used to transfect 5 million Jurkat cells with each cDNA alone or in combination (PRPK+TPRKB co-expression). Expression levels were assayed 48 hr post-transfection following lysis in 200 µL RIPA Buffer (50 mM Tris-HCl pH 7.4, 150 mM NaCl, 1% Nonidet P-40, 0.5% sodium deoxycholate, 0.1% SDS, 5 mM EDTA, 1 mM EGTA plus 1 Complete Mini protease inhibitor and 1 PhosSTOP phosphatase inhibitor tablet per 10 mL RIPA Buffer). Protein levels were assessed using the DC Protein Assay (Bio-Rad, Hercules, Calif.), and 30 µg lysate was resolved on a 4-12% SDS-PAGE gel prior to Western blot with anti-Myc Tag antibody (71D10, Cell Signaling Technology, Danvers, Mass.) or anti-vinculin loading control (hVIN-1, Sigma, St. Louis, Mo.).

Example 16

Figure 7:
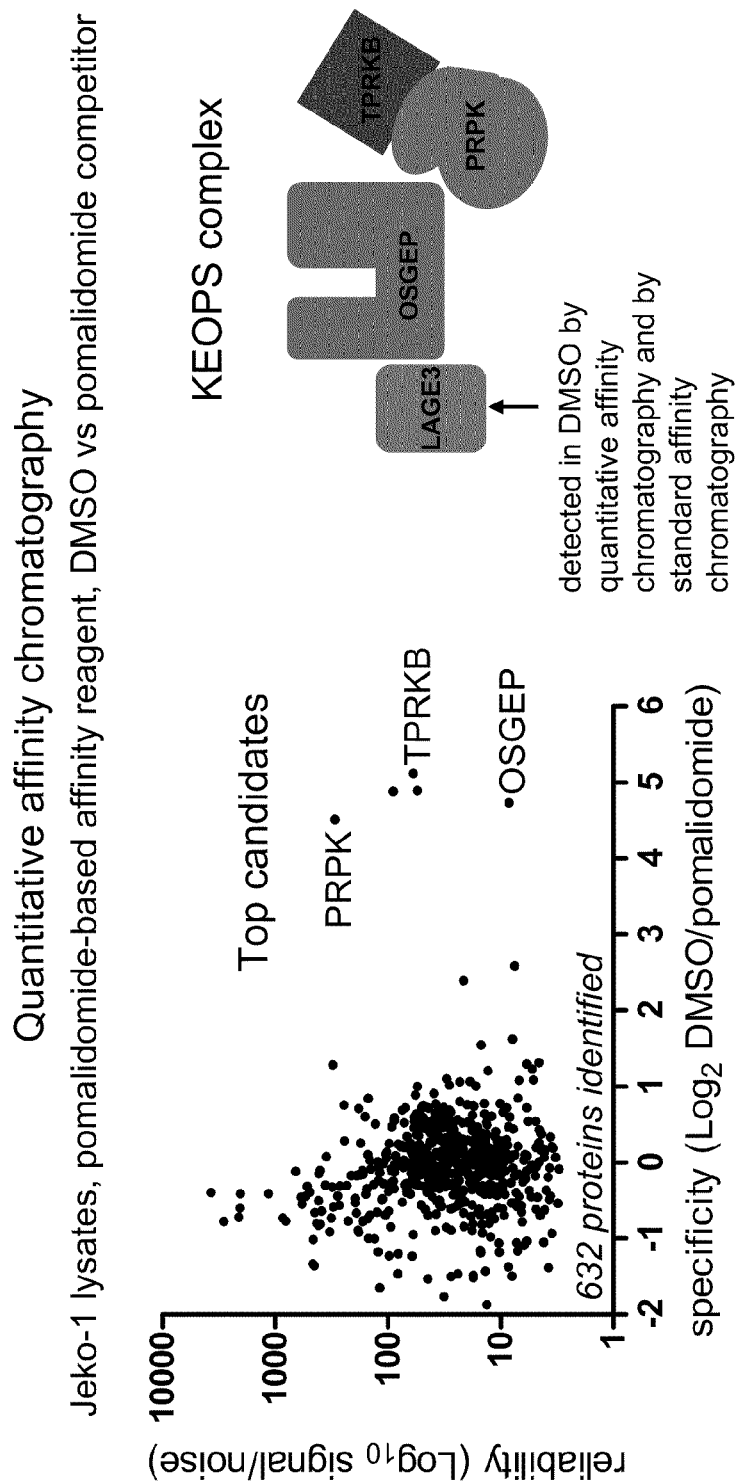
FIG. 7. Results from quantitative affinity chromatography showing human orthologs of yeast KEOPS complex bind.

SILAC-Based Quantitative Affinity Chromatography (see FIG. 7)

Cells were labeled and experiments were performed according to previously published protocols (Ong S and Mann M, 2006, *Nature Protocols*; Ong S et al, 2009, *PNAS*). Briefly, Jeko-1 cells were labeled with a "light" (L-Lysine, Sigma, St. Louis, Mo.) or "heavy" (L-Lysine-$^{13}C_6$,$^{15}N_2$, Cambridge Isotope, Andover, Mass.) amino acid in SILAC RPMI-1640 media (Thermo Fisher Scientific, Waltham, Mass.) supplemented with L-Arginine (Sigma, St. Louis, Mo.), 10% dialyzed FBS (Invitrogen, Carlsbad, Calif.), and 1% penicillin-streptomycin (Invitrogen). Jeko-1 cells of 80-90% confluency from a T225 flask were spun down and washed 2x with PBS and seeded 1:10 into light or heavy SILAC media. Cells were subcultured at least twice and allowed to grow in SILAC media for at least five cell doublings. Cells were seeded in 1 L cell culture bags (Lampire, Pipersville, Pa.) in the final expansion step to obtain sufficient quantities of cells for pulldown experiments. For affinity chromatography, cell lysates were prepared from $1 \times 10^9$ light or heavy Jeko-1 cells per pulldown sample by lysis in 4 mL Buffer B. Pulldowns were performed as above for standard small molecule affinity chromatography with the following modifications: Lysates were pre-cleared with 25 uL control affigel-PEG linker per sample for 45 mM Competition was performed with 16-fold excess pomalidomide or CMPD 31 added to the light lysate and DMSO added to the heavy lysate. Pulldowns were performed with 25 µL pomalidomide-based affigel reagent. Following the pulldowns, light and heavy samples were washed separately 1x with 800 µL Buffer B, then light and heavy samples were pooled and added to Mobicol columns and washed 3x with 800 µL Buffer B and 3×800 µL Buffer A. Samples were eluted in 30 µL 4×SDS sample buffer with 10 mM DTT. SILAC mass spectrometry and data analysis were performed by Dr. Steve Gygi and members of the Taplin Mass Spectrometry Facility (Harvard Medical School, Boston, Mass.).

Example 17

Figure 9:
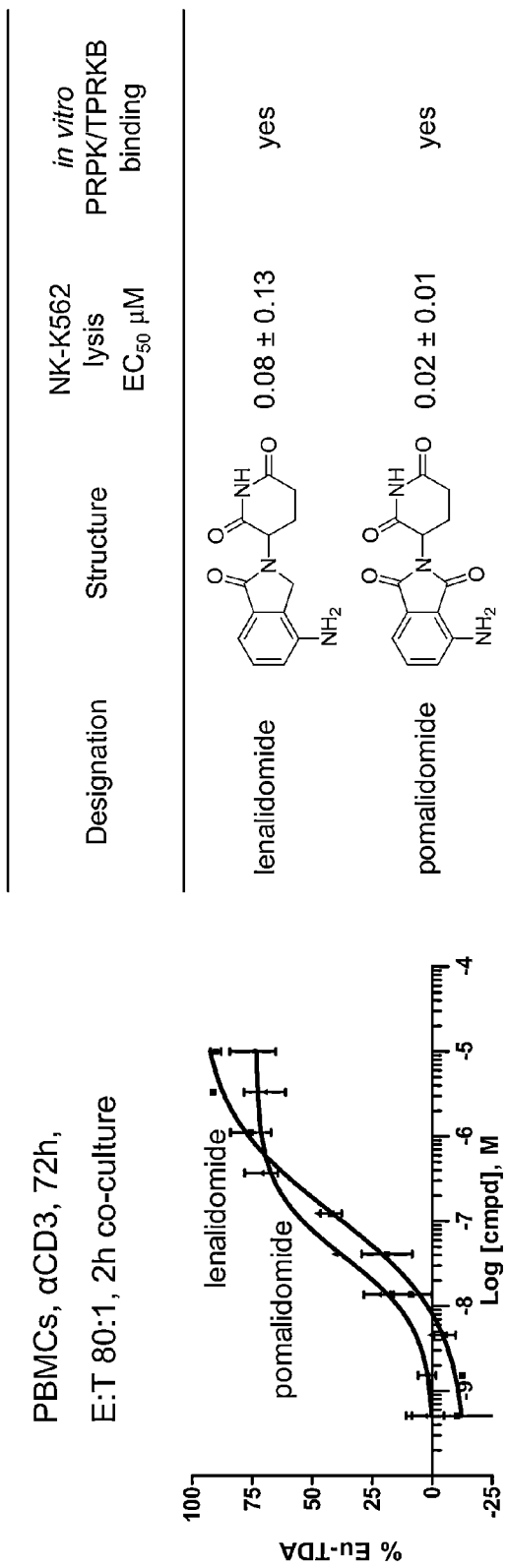
FIG. 9. Natural killer cell activation in PBMCs by lenalidomide and pomalidomide.

Natural Killer Cell Assay (see FIG. 9)

Treatment of PBMCs with Immunomodulatory Drugs.

On the day of initial treatment, cryopreserved peripheral blood mononuclear cells from a healthy donor (PBMCs; Astarte Biologics) were thawed in RPMI-1640 containing 10% fetal bovine serum, 1% penicillin-streptomycin and 25 mM HEPES buffer (complete medium) at 37° C. PBMCs were centrifuged two times at 1000 rpm to remove residual DMSO and debris and counted on a haemocytometer. Cells were used at a final cell density of $1 \times 10^6$ cells per mL in complete medium. PBMCs were stimulated with soluble anti-CD3 antibody (BD Pharmingen, clone UCHT1) at a final concentration of 1 µg/mL and added to 96-well round bottom plates with or without lenolidomide or pomalidomide at various concentrations for 72 hours at 37° C., 5% $CO_2$ (final DMSO concentration ≤0.2%). Positive control PBMCs were stimulated with IL-2 at a final concentration of 120 IU/mL (R&D systems) in the absence of anti-CD3 antibody.

DELFIA Assay for Assessment of NK Lytic Activity.

Following the 72 hour treatment, NK cells were assayed for lytic activity using the DELFIA cell cytoxicity assay from Perkin-Elmer according to manufacturer's instructions. In brief, K562 cells were grown in complete medium. In log phase, cells were washed once with PBS containing 20 mM HEPES. K562 cells were resuspended in DMEM containing 10% fetal bovine serum and 1% penicillin-streptomycin, counted on a hemacytometer and diluted to $1 \times 10^6$ cells per mL. BATDA ligand (5 µL) was added to 5 mL of K562 cells in a 50 mL conical tube. Following 10 minutes of incubation at 37° C., cells were washed three times in PBS containing 20 mM HEPES and 2.5 mM probenecid to prevent BATDA ligand efflux. K562 cells were resuspended in complete medium containing 2.5 mM probenecid and diluted to a final density of $5 \times 10^4$ cells per mL. Prior to mixing PBMC effector cells and K562 target cells, the plates containing PBMCs were spun down and resuspended in a final volume of 50 µL of fresh complete medium. PBMCs were then transferred to a separate 96-well round bottom plate to which 50 µL of K562 cells (2500 cells per well) were added (effector to target ratio of approximately 8:1). The assay plate was centrifuged for 5 minutes at 1000 rpm to enhance NK-K562 conjugation and allowed to incubate at 37° C. After 2 hours of incubation, 20 µL of the supernatant was removed and transferred to a Perkin-Elmer microtitration plate. Europium solution (200 µL) was added to the supernatants and the plate was placed on a Wallac Victor microplate reader. Following a 15 minute orbital shake at high speed, the plate was read using time-resolved fluorescence (Excitation at 340 nm, Emission at 615 nm; delay 400 µsec; counting window 400 µsec, cycle 1000 µsec). Raw counts were normalized as a percent of untreated DMSO control (basal NK activity, 0%) and IL-2 (maximal NK activity, 100%). Dose curve analysis for $EC_{50}$ values was performed using basic nonlinear regression with a sigmoidal dose response (variable slope) in GraphPad Prism 5 software.

Example 18

Immune Synapse Assay

Cell Staining and Treatment.

Logarithmically growing Jurkat cells from ATCC (clone E6-1) and RAMOS cells from ATCC are resuspended at $1 \times 10^6$ cells/mL in RPMI-1640 medium containing 1% antibiotic/antimycotic solution without serum. Additionally, an aliquot of cells is resuspended at $1 \times 10^6$ cells/mL in RPMI-1640 medium containing 10% FBS and 1% antibiotic/antimycotic solution to be used as an unstained control. RAMOS cells are stained with the dye DIO from Vybrant® Multicolor Cell-Labeling Kit (Invitrogen) by adding 5 µL of dye per mL of cells. Jurkat cells are stained with the dye DIL from Vybrant® Multicolor Cell-Labeling Kit (Invitrogen). Cells are stained for 10 minutes at 37° C. in 5% $CO_2$. Following staining, an equal volume of RPMI-1640 medium containing 10% FBS and 1% antibiotic/antimycotic solution and the cells are centrifuged down for 5 min at 1000 rpm. Cells are washed one time by aspirating off media and resuspending the pellet at $1 \times 10^6$ cells/mL. Media is aspirated and cells are resuspended at $1 \times 10^6$ cells/mL and a small aliquot is used to recount the cells and centrifuge them down once more for 5 min at 1000 rpm. The pellet is resuspended at $1 \times 10^6$ cells/mL based on the new cell count and incubated at 37° C. in 5% $CO_2$ until use. Then 400 µL of each cell type is removed and placed in a microcentrifuge tube and incubated at 37° C. in 5% $CO_2$ until fixation to use as a stained control.

For each sample 400 µL of stained RAMOS cells are added to a microcentrifuge tube. Samples are treated with compounds of interest for several hours at 37° C. in 5% $CO_2$. Following treatment 400 µL of stained Jurkat cells are added to the microcentrifuge tube and centrifuged at 500 rpm for 5 minutes at room temperature. Following centrifugation 400 µL of supernatant are removed from the microcentrifuge tube and incubated at 37° C. in 5% $CO_2$ for 30 minutes Immediately after conjugation the samples are fixed for 15 minutes at room temperature by the addition of 400 µL of 4% paraformaldehyde solution in PBS (Boston Bioproducts).

For a positive control, cells are treated with 2 µg/ml SEE for 1 hour then conjugated with Jurkat cells for 30 minutes. For a negative control RAMOS cells are incubated alone for 1 hour then conjugated with Jurkat cells for 30 minutes. Additional controls include unstained RAMOS and Jurkat cells and stained RAMOS and Jurkat cells for optimization of the FACS instrument.

FACS Analysis. This data acquisition protocol is optimized for use with the BD FacsCalibur flow cytometer. The flow cytometer must be properly compensated for fluorescence carry-over in the PMT detectors using the individually stained control tubes. DIO is detected in the FL-1 channel and DIL is detected in the FL-2 channel. At least 10,000 events are acquired for each sample where the flow rate does not exceed 500 events per second.

EQUIVALENTS AND SCOPE

The foregoing has been a description of certain non-limiting preferred embodiments of the invention. Those skilled in the art will recognize, or be able to ascertain using no more than routine experimentation, many equivalents to the specific embodiments of the invention described herein. Those of ordinary skill in the art will appreciate that various changes and modifications to this description may be made without departing from the spirit or scope of the present invention, as defined in the following claims.

In the claims articles such as "a,", "an" and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the claims or from relevant portions of the description is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise. For example, it is to be understood that any of the compositions of the invention can be used for inhibiting the formation, progression, and/or recurrence of adhesions at any of the locations, and/or due to any of the causes discussed herein or known in the art. It is also to be understood that any of the compositions made according to the methods for preparing compositions disclosed herein can be used for inhibiting the formation, progression, and/or recurrence of adhesions at any of the locations, and/or due to any of the causes discussed herein or known in the art. In addition, the invention encompasses compositions made according to any of the methods for preparing compositions disclosed herein.

Where elements are presented as lists, e.g., in Markush group format, it is to be understood that each subgroup of the elements is also disclosed, and any element(s) can be removed from the group. It is also noted that the term "comprising" is intended to be open and permits the inclusion of additional elements or steps. It should be understood that, in general, where the invention, or aspects of the invention, is/are referred to as comprising particular elements, features, steps, etc., certain embodiments of the invention or aspects of the invention consist, or consist essentially of, such elements, features, steps, etc. For purposes of simplicity those embodiments have not been specifically set forth in haec verba herein. Thus for each embodiment of the invention that comprises one or more elements, features, steps, etc., the invention also provides embodiments that consist or consist essentially of those elements, features, steps, etc.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in different embodiments of the invention, to the tenth of the unit of the lower limit of the range, unless the context clearly dictates otherwise. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Any embodiment, element, feature, application, or aspect of the compositions and/or methods of the invention (e.g., any derivative, any molecular weight range, any cross-linking agent, any type of bond hydrogel precursors, any class of biologically active agent or specific agent, any material composition, any route or location of administration, any purpose for which a composition is administered, etc.), can be excluded from any one or more claims. For purposes of brevity, all of the embodiments in which one or more elements, features, purposes, or aspects is excluded are not set forth explicitly herein.

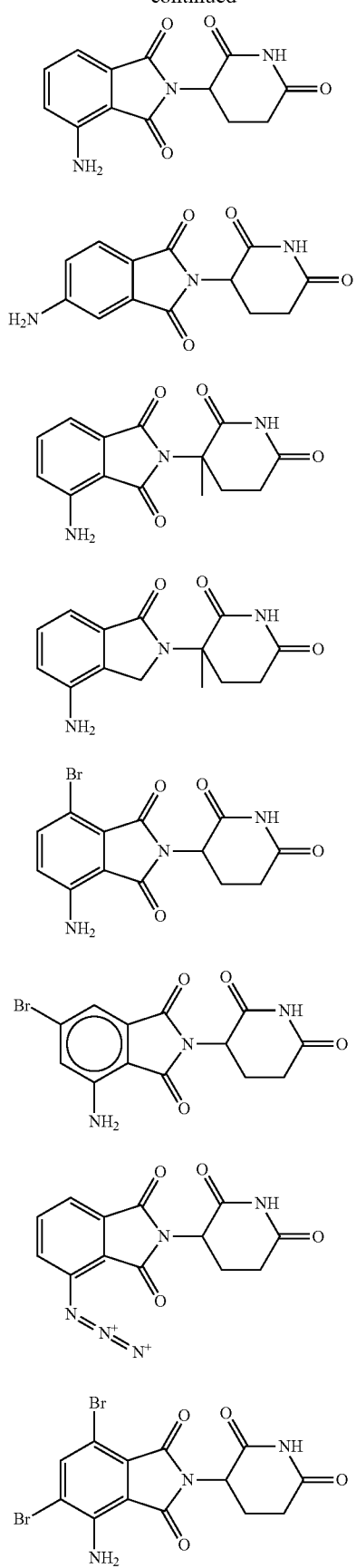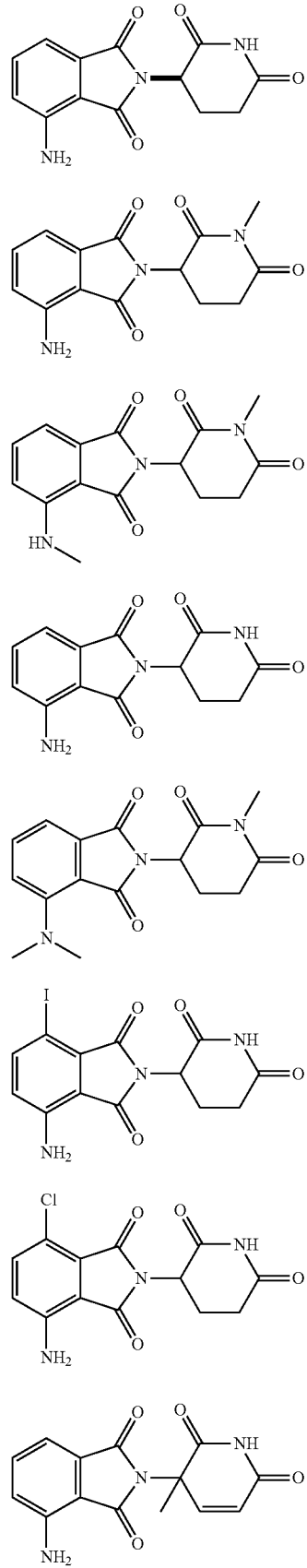

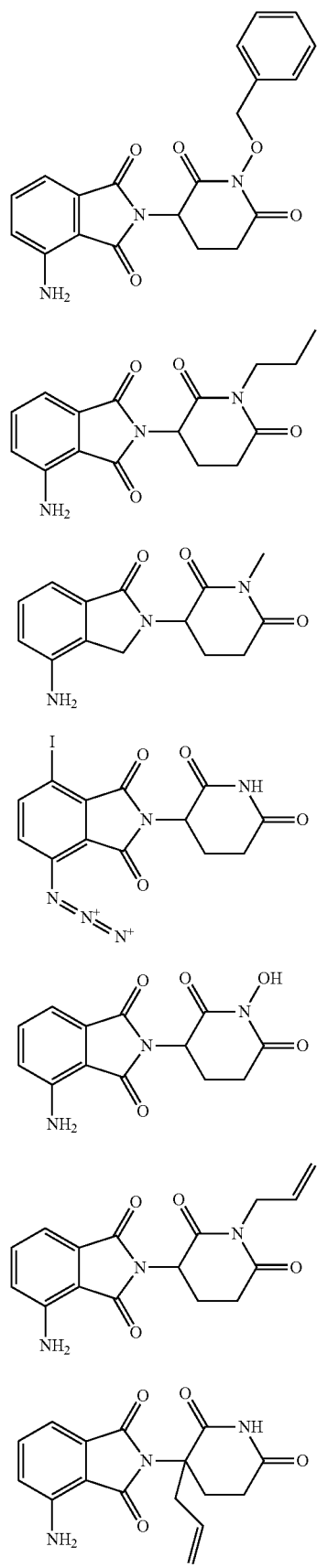
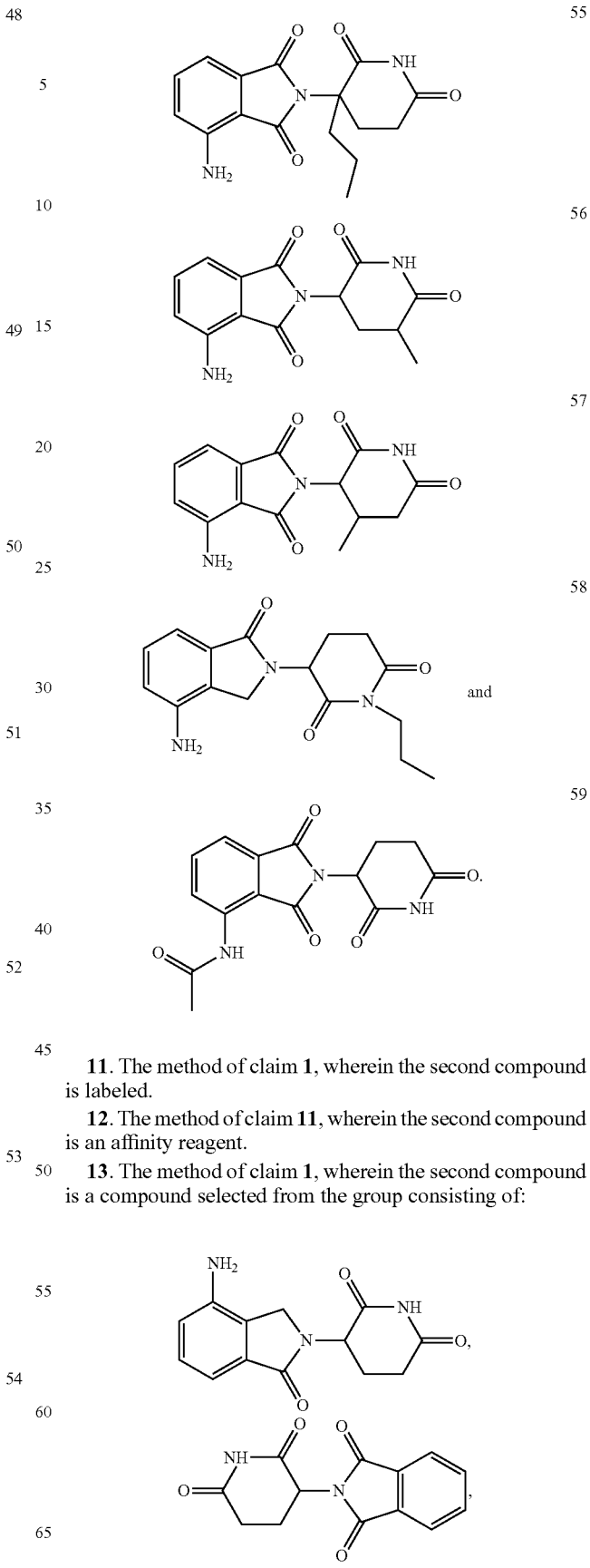
11. The method of claim 1, wherein the second compound is labeled.
12. The method of claim 11, wherein the second compound is an affinity reagent.
13. The method of claim 1, wherein the second compound is a compound selected from the group consisting of:
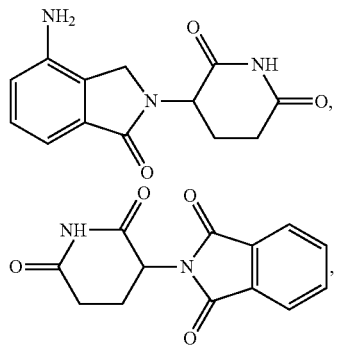

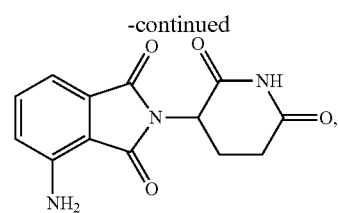

We claim:
1. A method of identifying an agent that modulates a PRPK/TPRKB complex comprising:
   (a) providing a PRPK/TPRKB complex comprising PRPK and TPRKB;
   (b) providing a first compound and a second compound;
   (c) contacting the first compound and the second compound with the PRPK/TPRKB complex; and
   (d) measuring an amount of interaction between the first compound, that is competed by the second compound, and the PRPK/TPRKB complex;
   wherein the second compound is a compound of formula I

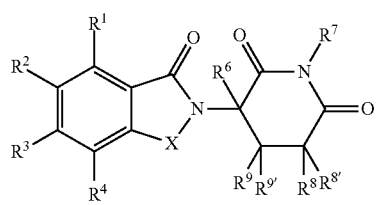

wherein:
X is —C(=O)— or —CH$_2$—;
R$^1$, R$^2$, R$^3$, and R$^4$ are independently hydrogen, halo, C$_{1-6}$ alkyl, C$_{1-6}$ alkoxy, or —N(R$^5$)$_2$;
each R$^5$ is independently hydrogen or C$_{1-6}$ alkyl, or two R$^5$ groups are taken together with the nitrogen to which they are attached to form a heterocycle;
R$^6$ is hydrogen, halo, benzyl, or C$_{1-8}$ alkyl;
R$^7$ is hydrogen, benzyl, or C$_{1-8}$ alkyl; and
R$^8$, R$^{8'}$, R$^9$, and R$^{9'}$ are independently hydrogen, halo, C$_{1-6}$ alkyl, or C$_{1-6}$ alkoxy.

2. The method of claim 1, further comprising:
   (e) providing a second PRPK/TPRKB complex;
   (f) providing the first compound and a third compound;
   (g) contacting the first compound and the third compound with the second PRPK/TPRKB complex;
   (h) measuring an amount of interaction between the first compound and the second PRPK/TPRKB complex that is not competed by the third compound;
   (i) comparing the amount of interaction determined in (d), with that of determined in (h); and
   (j) identifying the first compound competed by the second compound but not by the third compound as an agent that modulates a PRPK/TPRKB complex.

3. The method of claim 1, wherein the PRPK/TPRKB complex is a KEOPS complex that comprises PRPK, TPRKB, OSGEP, and LAGE3 or homologs thereof.

4. The method of claim 2, wherein the PRPK/TPRKB complex is a KEOPS complex that comprises PRPK, TPRKB, OSGEP, and LAGE3 or homologs thereof.

5. The method of claim 2, wherein molar ratio of (a) the first compound to (b) the second compound (b/a) is from 20 to 80.

6. The method of claim 2, wherein the second compound is a compound selected from the group consisting of:

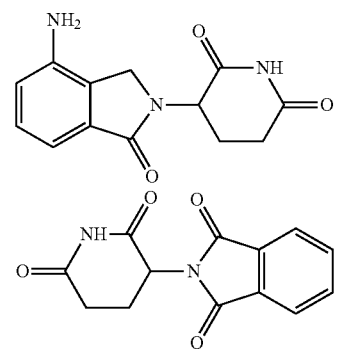

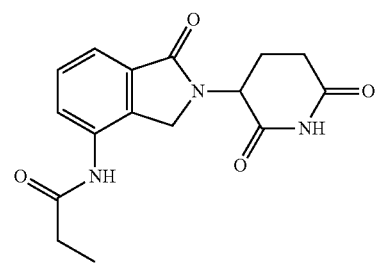

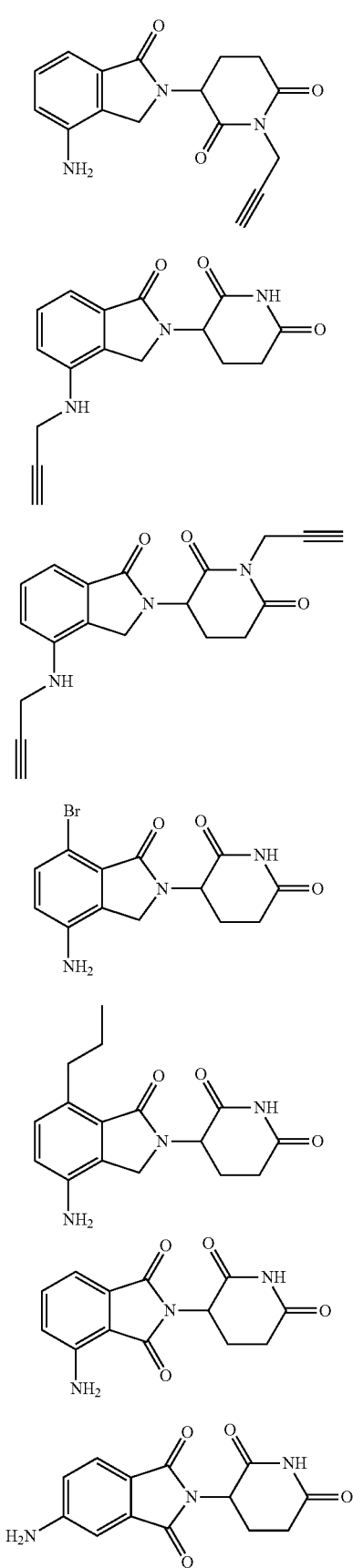
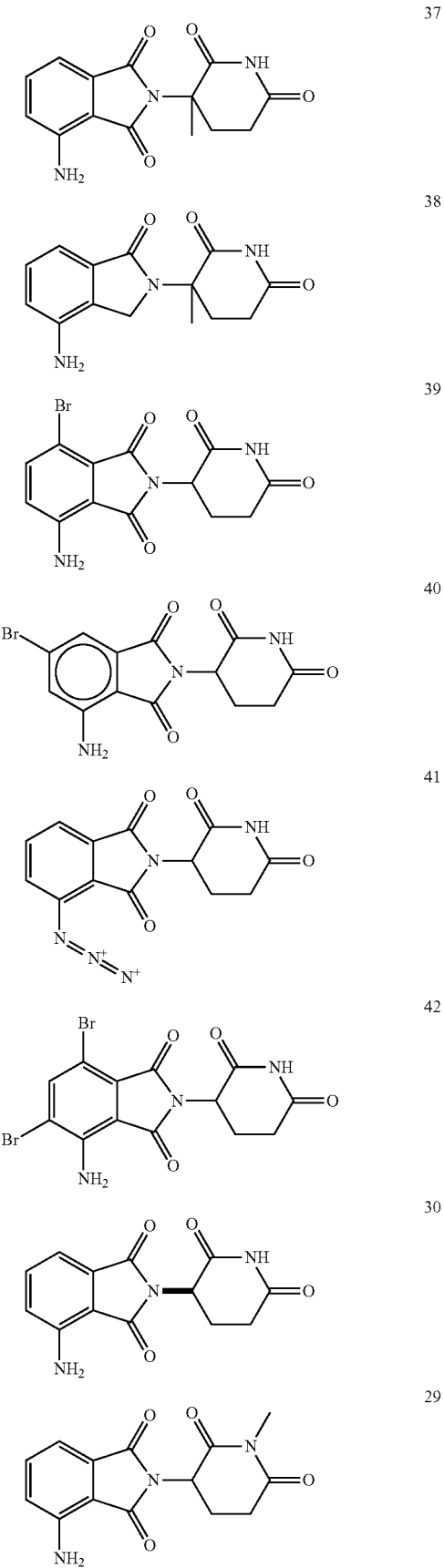

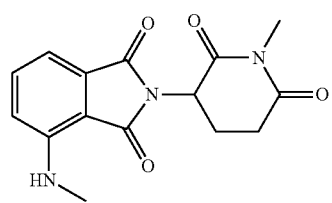
43
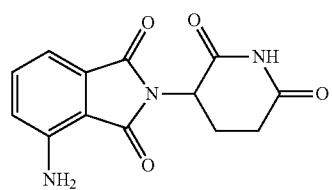
28
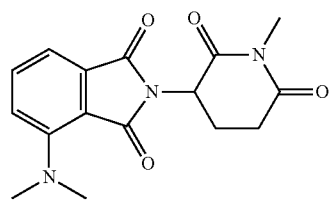
44
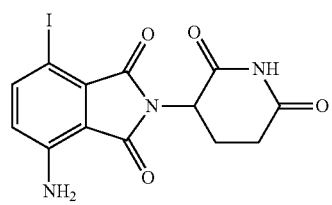
45
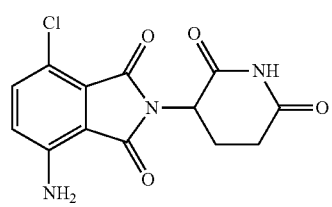
46
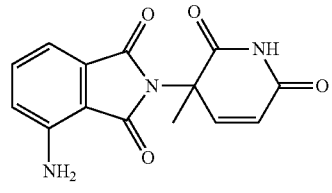
47
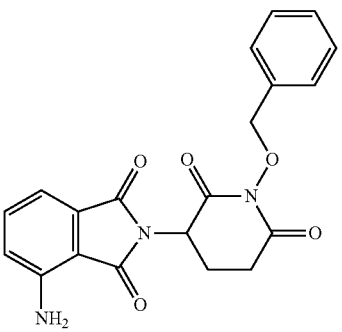
48
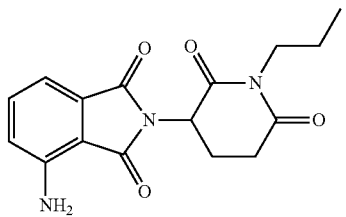
49
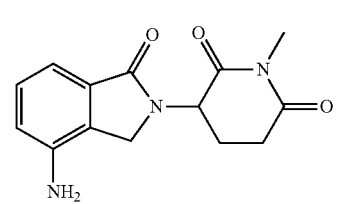
50
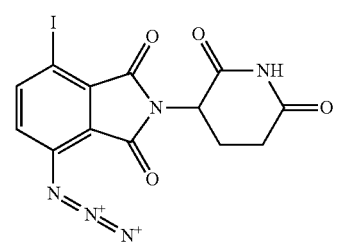
51
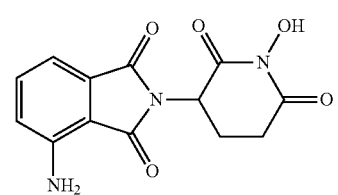
52
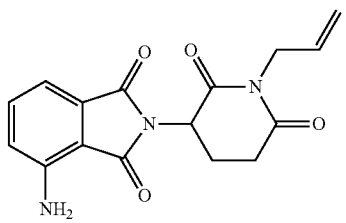
53
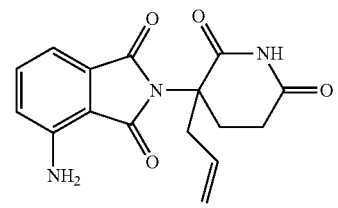
54
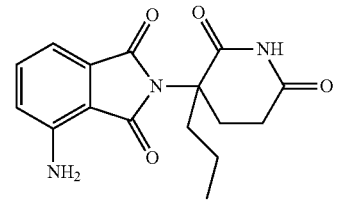
55

85
-continued
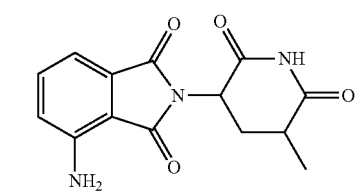
56
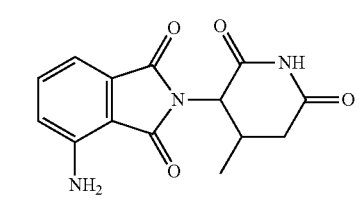
57
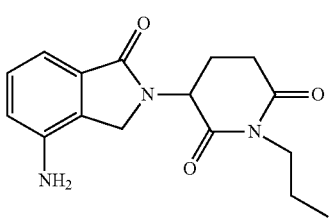
58
and
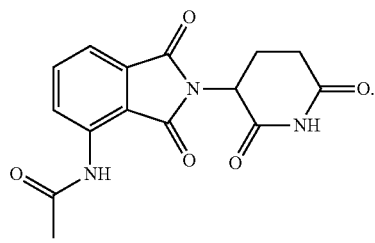
59
7. The method of claim 2, wherein the second compound is labeled.
8. The method of claim 7, wherein the second compound is an affinity reagent.
9. The method of claim 1, wherein molar ratio of (a) the first compound to (b) the second compound (b/a) is from 20 to 80.
10. The method of claim 1, wherein the second compound is a compound selected from the group consisting of:
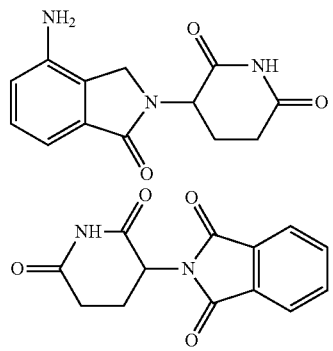
86
-continued
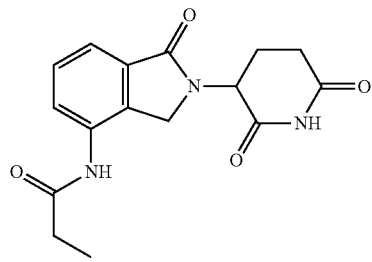
27
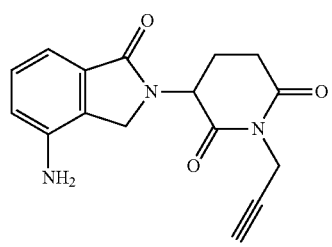
32
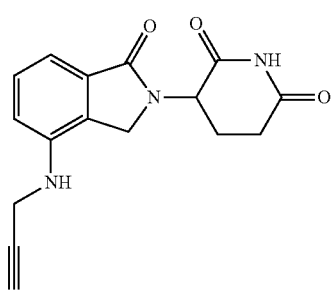
33
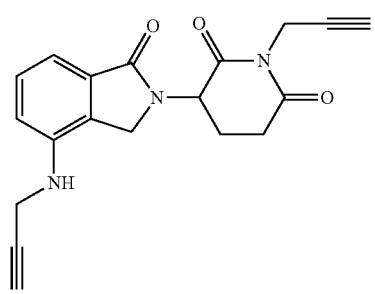
34
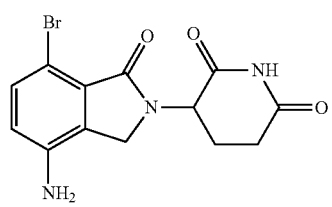
35
36